(12) United States Patent
Christianson et al.

(10) Patent No.: US 11,173,027 B2
(45) Date of Patent: *Nov. 16, 2021

(54) SIDE-DELIVERABLE TRANSCATHETER PROSTHETIC VALVES AND METHODS FOR DELIVERING AND ANCHORING THE SAME

(71) Applicant: VDyne, Inc., Maple Grove, MN (US)

(72) Inventors: Mark Christianson, Plymouth, MN (US); Robert Vidlund, Forest Lake, MN (US); Scott Kramer, Minneapolis, MN (US)

(73) Assignee: VDyne, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/154,227

(22) Filed: Jan. 21, 2021

(65) Prior Publication Data
US 2021/0137677 A1     May 13, 2021

Related U.S. Application Data

(63) Continuation of application No. PCT/US2020/022828, filed on Mar. 13, 2020, which
(Continued)

(51) Int. Cl.
*A61F 2/24*     (2006.01)
(52) U.S. Cl.
CPC .... *A61F 2/2418* (2013.01); *A61F 2220/0008* (2013.01)
(58) Field of Classification Search
CPC .................................. A61F 2/24; A61F 2/2427
(Continued)

(56) References Cited

U.S. PATENT DOCUMENTS

| 5,397,351 A | 3/1995 | Pavcnik et al. |
| 5,509,428 A | 4/1996 | Dunlop |

(Continued)

FOREIGN PATENT DOCUMENTS

| AU | 2006203686 B2 | 11/2008 |
| AU | 2009219415 A1 | 9/2009 |

(Continued)

OTHER PUBLICATIONS

Office Action for U.S. Appl. No. 16/435,687, dated Aug. 7, 2019, 19 pages.
(Continued)

*Primary Examiner* — Suzette J Gherbi

(57) ABSTRACT

A side-deliverable prosthetic valve includes an outer frame, a flow control component mounted within the outer frame, and an anchoring element coupled to a distal side of the outer frame. The prosthetic valve is foldable along a longitudinal axis and compressible along a central axis to a compressed configuration for side delivery via a delivery catheter and is expandable to an expanded configuration when released from the delivery catheter. An end portion of the anchoring element is configured to engage a guide wire. The anchoring element is extended during deployment to allow the anchoring element to capture at least one of native leaflet or chordae and, in response to the guide wire being disengaged from the end portion, transitions to a folded configuration to secure at least one of the native leaflet or the chordae between the anchoring element and the distal side of the outer frame.

24 Claims, 46 Drawing Sheets

Related U.S. Application Data is a continuation-in-part of application No. 16/438,434, filed on Jun. 11, 2019, now Pat. No. 10,631,983, said application No. PCT/US2020/022828 is a continuation-in-part of application No. 16/442,504, filed on Jun. 16, 2019, now Pat. No. 10,758,346, said application No. PCT/US2020/022828 is a continuation-in-part of application No. 16/445,210, filed on Jun. 19, 2019.

(60) Provisional application No. 62/818,108, filed on Mar. 14, 2019, provisional application No. 62/818,109, filed on Mar. 14, 2019, provisional application No. 62/818,688, filed on Mar. 14, 2019, provisional application No. 62/818,742, filed on Mar. 14, 2019.

(58) Field of Classification Search
USPC .................................................. 623/2.1–2.19
See application file for complete search history.

(56) References Cited

U.S. PATENT DOCUMENTS

| | | | |
|---|---|---|---|
| 6,006,134 A | 12/1999 | Hill et al. | |
| 6,197,013 B1 | 3/2001 | Reed et al. | |
| 6,290,719 B1 | 9/2001 | Garberoglio | |
| 6,449,507 B1 | 9/2002 | Hill et al. | |
| 6,532,388 B1 | 3/2003 | Hill et al. | |
| 6,582,467 B1 | 6/2003 | Teitelbaum et al. | |
| 6,628,987 B1 | 9/2003 | Hill et al. | |
| 6,718,208 B2 | 4/2004 | Hill et al. | |
| 6,769,434 B2 | 8/2004 | Liddicoat et al. | |
| 6,890,330 B2 | 5/2005 | Streeter et al. | |
| 6,896,690 B1 | 5/2005 | Lambrecht et al. | |
| 6,904,318 B2 | 6/2005 | Hill et al. | |
| 6,929,653 B2 | 8/2005 | Strecter | |
| 7,074,189 B1 | 7/2006 | Montegrande | |
| 7,125,418 B2 | 10/2006 | Duran et al. | |
| 7,175,660 B2* | 2/2007 | Cartledge | A61B 17/00234 623/2.11 |
| 7,201,761 B2 | 4/2007 | Woolfson et al. | |
| 7,225,019 B2 | 5/2007 | Jahns et al. | |
| 7,269,457 B2 | 9/2007 | Shafer et al. | |
| 7,331,991 B2 | 2/2008 | Kheradvar et al. | |
| 7,374,571 B2 | 5/2008 | Pease et al. | |
| 7,449,027 B2 | 11/2008 | Hunt et al. | |
| 7,621,948 B2* | 11/2009 | Herrmann | A61F 2/243 623/2.1 |
| 7,717,952 B2 | 5/2010 | Case et al. | |
| 7,749,245 B2 | 7/2010 | Cohn et al. | |
| 7,753,949 B2* | 7/2010 | Lamphere | A61F 2/2412 623/1.26 |
| 7,828,840 B2 | 11/2010 | Biggs et al. | |
| 7,846,199 B2 | 12/2010 | Paul, Jr. et al. | |
| 8,303,648 B2 | 11/2012 | Grewe et al. | |
| 8,366,768 B2 | 2/2013 | Zhang | |
| 8,491,650 B2 | 7/2013 | Wiemeyer et al. | |
| 8,568,474 B2 | 10/2013 | Yeung et al. | |
| 8,641,752 B1 | 2/2014 | Holm et al. | |
| 8,696,743 B2 | 4/2014 | Holecek et al. | |
| 8,728,153 B2 | 5/2014 | Bishop et al. | |
| 8,758,395 B2 | 6/2014 | Kleshinski | |
| 8,846,390 B2 | 9/2014 | Dove et al. | |
| 8,876,892 B2 | 11/2014 | Tran et al. | |
| 8,900,295 B2 | 12/2014 | Migliazza et al. | |
| 8,915,958 B2 | 12/2014 | Braido | |
| 8,926,690 B2 | 1/2015 | Kovalsky | |
| 8,926,692 B2 | 1/2015 | Dwork | |
| 8,926,694 B2 | 1/2015 | Costello | |
| 8,940,044 B2 | 1/2015 | Hammer et al. | |
| 8,956,404 B2 | 2/2015 | Bortlein et al. | |
| 8,986,370 B2 | 3/2015 | Annest et al. | |
| 9,011,524 B2 | 4/2015 | Eberhardt | |
| 9,017,399 B2 | 4/2015 | Gross et al. | |
| 9,050,188 B2 | 6/2015 | Schweich, Jr. | |
| 9,072,604 B1 | 7/2015 | Melnick et al. | |
| 9,119,714 B2 | 9/2015 | Shandas et al. | |
| 9,216,076 B2 | 12/2015 | Mitra et al. | |
| 9,232,995 B2 | 1/2016 | Kovalsky et al. | |
| 9,241,792 B2 | 1/2016 | Benichou et al. | |
| 9,248,016 B2 | 2/2016 | Oba et al. | |
| 9,259,215 B2 | 2/2016 | Chou et al. | |
| 9,277,990 B2 | 3/2016 | Klima et al. | |
| 9,289,282 B2 | 3/2016 | Olson et al. | |
| 9,289,296 B2 | 3/2016 | Braido et al. | |
| 9,295,547 B2 | 3/2016 | Costello et al. | |
| 9,301,839 B2 | 4/2016 | Stante et al. | |
| 9,308,086 B2 | 4/2016 | Ho | |
| 9,339,367 B2 | 5/2016 | Carpenter | |
| 9,370,418 B2 | 6/2016 | Pintor et al. | |
| 9,381,083 B2 | 7/2016 | Costello | |
| 9,387,075 B2 | 7/2016 | Bortlein et al. | |
| 9,393,111 B2 | 7/2016 | Ma et al. | |
| 9,414,915 B2 | 8/2016 | Lombardi et al. | |
| 9,433,500 B2 | 9/2016 | Chau et al. | |
| 9,440,054 B2 | 9/2016 | Bishop et al. | |
| 9,456,899 B2 | 10/2016 | Yeung et al. | |
| 9,468,525 B2 | 10/2016 | Kovalsky et al. | |
| 9,474,604 B2 | 10/2016 | Centola et al. | |
| 9,486,306 B2 | 11/2016 | Tegels et al. | |
| 9,510,941 B2 | 12/2016 | Bishop et al. | |
| 9,554,902 B2 | 1/2017 | Braido | |
| 9,579,196 B2 | 2/2017 | Morriss et al. | |
| 9,579,200 B2 | 2/2017 | Lederman et al. | |
| 9,610,159 B2 | 4/2017 | Christianson et al. | |
| 9,615,925 B2 | 4/2017 | Subramanian et al. | |
| 9,629,719 B2 | 4/2017 | Rothstein | |
| 9,636,222 B2 | 5/2017 | Oslund | |
| 9,649,191 B2 | 5/2017 | Savage et al. | |
| 9,662,202 B2 | 5/2017 | Quill et al. | |
| 9,662,203 B2 | 5/2017 | Sheahan et al. | |
| 9,662,209 B2 | 5/2017 | Gross et al. | |
| 9,675,454 B2 | 6/2017 | Vidlund et al. | |
| 9,675,485 B2 | 6/2017 | Essinger et al. | |
| 9,687,343 B2 | 6/2017 | Bortlein et al. | |
| 9,707,076 B2 | 7/2017 | Stack et al. | |
| 9,713,530 B2 | 7/2017 | Cabiri et al. | |
| 9,750,607 B2 | 9/2017 | Ganesan et al. | |
| 9,763,778 B2 | 9/2017 | Eidenschink | |
| 9,763,779 B2 | 9/2017 | Bortlein et al. | |
| 9,788,946 B2 | 10/2017 | Bobo, Jr. et al. | |
| 9,839,511 B2 | 12/2017 | Ma et al. | |
| 9,849,011 B2 | 12/2017 | Zimmerman et al. | |
| 9,855,384 B2 | 1/2018 | Cohen et al. | |
| 9,861,464 B2 | 1/2018 | Azimpour et al. | |
| 9,895,219 B2 | 2/2018 | Costello et al. | |
| 9,901,330 B2 | 2/2018 | Akpinar | |
| 9,918,838 B2 | 3/2018 | Ring | |
| 9,943,409 B2 | 4/2018 | Kim et al. | |
| 9,949,825 B2 | 4/2018 | Braido et al. | |
| 9,968,444 B2 | 5/2018 | Millwee et al. | |
| 9,968,445 B2 | 5/2018 | Kheradvar | |
| 9,980,815 B2 | 5/2018 | Nitzan et al. | |
| 9,987,121 B2 | 6/2018 | Blanzy | |
| 10,010,411 B2 | 7/2018 | Peter | |
| 10,010,412 B2 | 7/2018 | Taft et al. | |
| 10,022,054 B2 | 7/2018 | Najafi et al. | |
| 10,022,222 B2 | 7/2018 | Groothuis et al. | |
| 10,022,223 B2 | 7/2018 | Bruchman | |
| 10,028,821 B2 | 7/2018 | Centola et al. | |
| 10,028,831 B2 | 7/2018 | Morin et al. | |
| 10,034,667 B2 | 7/2018 | Morris et al. | |
| 10,034,747 B2 | 7/2018 | Harewood | |
| 10,039,638 B2 | 8/2018 | Bruchman | |
| 10,058,315 B2 | 8/2018 | Rafiee et al. | |
| 10,058,411 B2 | 8/2018 | Fifer et al. | |
| 10,058,421 B2 | 8/2018 | Eberhardt et al. | |
| 10,058,426 B2 | 8/2018 | Barbarino | |
| 10,064,405 B2 | 9/2018 | Dale et al. | |
| 10,080,653 B2 | 9/2018 | Conklin et al. | |
| 10,085,835 B2 | 10/2018 | Thambar et al. | |
| 10,105,224 B2 | 10/2018 | Buchbinder | |
| 10,117,741 B2 | 11/2018 | Schweich, Jr. | |
| 10,123,874 B2 | 11/2018 | Khairkhahan et al. | |

(56) References Cited

U.S. PATENT DOCUMENTS

| | | |
|---|---|---|
| 10,130,331 B2 | 11/2018 | Stigall et al. |
| 10,130,467 B2 | 11/2018 | Braido et al. |
| 10,149,685 B2 | 12/2018 | Kizuka |
| 10,154,905 B2 | 12/2018 | Duffy |
| 10,179,043 B2 | 1/2019 | Cohen-Tzemach et al. |
| 10,182,908 B2 | 1/2019 | Tubishevitz et al. |
| 10,182,911 B2 | 1/2019 | Hillukka |
| 10,206,775 B2 | 2/2019 | Kovalsky et al. |
| 10,219,895 B2 | 3/2019 | Wagner et al. |
| 10,219,896 B2 | 3/2019 | Sandstrom et al. |
| 10,220,192 B2 | 3/2019 | Drasler et al. |
| 10,226,178 B2 | 3/2019 | Cohen et al. |
| 10,226,335 B2 | 3/2019 | Cartledge et al. |
| 10,245,142 B2 | 4/2019 | Bonhoeffer |
| 10,258,467 B2 | 4/2019 | Hou et al. |
| 10,265,173 B2 | 4/2019 | Griffin et al. |
| 10,321,987 B2 | 6/2019 | Wang et al. |
| 10,321,995 B1 * | 6/2019 | Christianson ......... A61F 2/2409 |
| 10,327,895 B2 | 6/2019 | Lozonschi et al. |
| 10,327,899 B2 | 6/2019 | Sandstrom et al. |
| 10,329,066 B2 | 6/2019 | Kruetzfeldt et al. |
| 10,350,047 B2 | 7/2019 | Rajpara et al. |
| 10,357,361 B2 | 7/2019 | Rafi et al. |
| 10,368,989 B2 | 8/2019 | Duffy et al. |
| 10,398,550 B2 | 9/2019 | Chalekian et al. |
| 10,426,611 B2 | 10/2019 | Hariton et al. |
| 10,433,957 B2 | 10/2019 | Khouengboua et al. |
| 10,433,960 B1 | 10/2019 | Sutherland et al. |
| 10,463,489 B2 | 11/2019 | Christianson et al. |
| 10,485,976 B2 | 11/2019 | Streeter et al. |
| 10,595,994 B1 * | 3/2020 | Christianson ......... A61F 2/2436 |
| 10,631,983 B1 * | 4/2020 | Christianson ........... A61F 2/243 |
| 10,653,522 B1 | 5/2020 | Vidlund et al. |
| 10,758,346 B1 * | 9/2020 | Christianson ......... A61F 2/2418 |
| 11,071,627 B2 | 7/2021 | Saikrishnan et al. |
| 11,076,956 B2 | 8/2021 | Christianson et al. |
| 2003/0040772 A1 | 2/2003 | Hyodoh et al. |
| 2003/0153901 A1 | 8/2003 | Herweck et al. |
| 2003/0166990 A1 | 9/2003 | Trauthen et al. |
| 2003/0171801 A1 | 9/2003 | Bates |
| 2004/0088047 A1 | 5/2004 | Spence et al. |
| 2004/0116996 A1 | 6/2004 | Freitag |
| 2004/0199209 A1 | 10/2004 | Hill et al. |
| 2005/0010246 A1 | 1/2005 | Streeter et al. |
| 2005/0107811 A1 | 5/2005 | Starksen et al. |
| 2005/0137686 A1 | 6/2005 | Salahieh et al. |
| 2006/0015167 A1 | 1/2006 | Armstrong |
| 2006/0190075 A1 | 8/2006 | Jordan et al. |
| 2006/0195180 A1 | 8/2006 | Kheradvar et al. |
| 2006/0271098 A1 | 11/2006 | Peacock, III |
| 2006/0276887 A1 | 12/2006 | Brady et al. |
| 2007/0016286 A1 * | 1/2007 | Herrmann ............... A61F 2/243 623/2.11 |
| 2007/0027535 A1 | 2/2007 | Purdy, Jr. et al. |
| 2007/0032850 A1 | 2/2007 | Ruiz et al. |
| 2007/0038295 A1 | 2/2007 | Case et al. |
| 2007/0100427 A1 | 5/2007 | Perouse |
| 2007/0162102 A1 | 7/2007 | Ryan et al. |
| 2007/0208417 A1 | 9/2007 | Agnew |
| 2007/0213805 A1 | 9/2007 | Schaeffer et al. |
| 2007/0233176 A1 | 10/2007 | Gilson et al. |
| 2007/0233228 A1 | 10/2007 | Eberhardt |
| 2007/0288087 A1 | 12/2007 | Fearnot et al. |
| 2008/0004686 A1 | 1/2008 | Hunt et al. |
| 2008/0020013 A1 | 1/2008 | Reyes et al. |
| 2008/0071287 A1 | 3/2008 | Goto |
| 2008/0132999 A1 | 6/2008 | Mericle et al. |
| 2008/0140181 A1 | 6/2008 | Reynolds et al. |
| 2008/0200977 A1 | 8/2008 | Paul et al. |
| 2008/0200980 A1 | 8/2008 | Robin et al. |
| 2008/0208332 A1 | 8/2008 | Lamphere et al. |
| 2008/0221672 A1 | 9/2008 | Lamphere et al. |
| 2008/0262592 A1 | 10/2008 | Jordan et al. |
| 2008/0262609 A1 | 10/2008 | Gross et al. |
| 2008/0275550 A1 | 11/2008 | Kheradvar et al. |
| 2009/0005863 A1 | 1/2009 | Goetz et al. |
| 2009/0094189 A1 | 4/2009 | Stephens |
| 2009/0192586 A1 | 7/2009 | Tabor et al. |
| 2009/0254174 A1 | 10/2009 | Case et al. |
| 2009/0264991 A1 | 10/2009 | Paul, Jr. et al. |
| 2009/0287290 A1 | 11/2009 | Macaulay et al. |
| 2010/0049294 A1 | 2/2010 | Zukowski et al. |
| 2010/0049313 A1 | 2/2010 | Alon et al. |
| 2010/0121434 A1 | 5/2010 | Paul et al. |
| 2010/0160773 A1 | 6/2010 | Cohen et al. |
| 2010/0161043 A1 | 6/2010 | Maisano et al. |
| 2010/0168844 A1 | 7/2010 | Toomes et al. |
| 2010/0174363 A1 | 7/2010 | Castro |
| 2010/0179583 A1 | 7/2010 | Carpenter |
| 2010/0179584 A1 | 7/2010 | Carpenter |
| 2010/0179647 A1 | 7/2010 | Carpenter |
| 2010/0280591 A1 | 11/2010 | Shin et al. |
| 2010/0305685 A1 | 12/2010 | Millwee et al. |
| 2011/0029071 A1 | 2/2011 | Zlotnick et al. |
| 2011/0071613 A1 | 3/2011 | Wood et al. |
| 2011/0098804 A1 | 4/2011 | Yeung et al. |
| 2011/0125145 A1 | 5/2011 | Mody et al. |
| 2011/0160836 A1 | 6/2011 | Behan |
| 2011/0172764 A1 | 7/2011 | Badhwar |
| 2011/0224785 A1 | 9/2011 | Hacohen et al. |
| 2011/0245911 A1 | 10/2011 | Quill et al. |
| 2011/0245917 A1 | 10/2011 | Savage |
| 2011/0251675 A1 | 10/2011 | Dwork |
| 2011/0257721 A1 | 10/2011 | Tabor |
| 2011/0264191 A1 | 10/2011 | Rothstein |
| 2012/0022605 A1 | 1/2012 | Jahns et al. |
| 2012/0022633 A1 | 1/2012 | Olson et al. |
| 2012/0022639 A1 | 1/2012 | Hacohen et al. |
| 2012/0022640 A1 | 1/2012 | Gross et al. |
| 2012/0022644 A1 | 1/2012 | Reich et al. |
| 2012/0035701 A1 | 2/2012 | To |
| 2012/0065723 A1 | 3/2012 | Drasler et al. |
| 2012/0123531 A1 | 5/2012 | Tsukashima et al. |
| 2012/0137521 A1 | 6/2012 | Millwee et al. |
| 2012/0165928 A1 | 6/2012 | Nitzan et al. |
| 2012/0172981 A1 | 7/2012 | DuMontelle |
| 2012/0203336 A1 | 8/2012 | Annest |
| 2012/0209375 A1 | 8/2012 | Madrid et al. |
| 2012/0232574 A1 | 9/2012 | Kim et al. |
| 2012/0277853 A1 | 11/2012 | Rothstein |
| 2012/0310327 A1 | 12/2012 | McHugo |
| 2013/0055941 A1 | 3/2013 | Holecek et al. |
| 2013/0131714 A1 | 5/2013 | Wang et al. |
| 2013/0131792 A1 | 5/2013 | Miller et al. |
| 2013/0166017 A1 | 6/2013 | Cartledge et al. |
| 2013/0184742 A1 | 7/2013 | Ganesan et al. |
| 2013/0190857 A1 | 7/2013 | Mitra et al. |
| 2013/0190861 A1 | 7/2013 | Chau et al. |
| 2013/0197621 A1 | 8/2013 | Ryan et al. |
| 2013/0226289 A1 | 8/2013 | Shaolian |
| 2013/0238010 A1 | 9/2013 | Johnson et al. |
| 2013/0238089 A1 | 9/2013 | Lichtenstein et al. |
| 2013/0253570 A1 | 9/2013 | Bates |
| 2013/0274618 A1 | 10/2013 | Hou et al. |
| 2013/0274855 A1 | 10/2013 | Stante et al. |
| 2013/0282110 A1 | 10/2013 | Schweich, Jr. |
| 2013/0297010 A1 | 11/2013 | Bishop et al. |
| 2013/0331929 A1 | 12/2013 | Mitra et al. |
| 2014/0000112 A1 | 1/2014 | Braido |
| 2014/0005540 A1 | 1/2014 | Merhi |
| 2014/0005768 A1 | 1/2014 | Thomas |
| 2014/0012372 A1 | 1/2014 | Chau et al. |
| 2014/0018915 A1 | 1/2014 | Baidillah et al. |
| 2014/0039511 A1 | 2/2014 | Morris et al. |
| 2014/0039611 A1 | 2/2014 | Lane et al. |
| 2014/0081383 A1 | 3/2014 | Eberhardt et al. |
| 2014/0088680 A1 | 3/2014 | Costello et al. |
| 2014/0107758 A1 | 4/2014 | Glazier |
| 2014/0110279 A1 | 4/2014 | Kruetzfeldt et al. |
| 2014/0114403 A1 | 4/2014 | Dale et al. |
| 2014/0121763 A1 | 5/2014 | Duffy et al. |
| 2014/0135895 A1 | 5/2014 | Andress |
| 2014/0142695 A1 | 5/2014 | Gross et al. |
| 2014/0172070 A1 | 6/2014 | Seguin |

(56) References Cited

U.S. PATENT DOCUMENTS

| | | |
|---|---|---|
| 2014/0180069 A1 | 6/2014 | Millett |
| 2014/0180070 A1 | 6/2014 | Millett et al. |
| 2014/0194704 A1 | 7/2014 | Millett et al. |
| 2014/0214069 A1 | 7/2014 | Franklin |
| 2014/0214159 A1 | 7/2014 | Vidlund et al. |
| 2014/0222136 A1 | 8/2014 | Geist et al. |
| 2014/0222137 A1 | 8/2014 | Miller et al. |
| 2014/0222142 A1 | 8/2014 | Kovalsky et al. |
| 2014/0249566 A1 | 9/2014 | Quinn et al. |
| 2014/0257466 A1 | 9/2014 | Board et al. |
| 2014/0257467 A1 | 9/2014 | Lane et al. |
| 2014/0276616 A1 | 9/2014 | Smith et al. |
| 2014/0276971 A1 | 9/2014 | Kovach |
| 2014/0277342 A1 | 9/2014 | Roeder et al. |
| 2014/0277388 A1 | 9/2014 | Skemp |
| 2014/0277408 A1 | 9/2014 | Folan |
| 2014/0296962 A1 | 10/2014 | Cartledge et al. |
| 2014/0296969 A1 | 10/2014 | Tegels et al. |
| 2014/0303718 A1 | 10/2014 | Tegels et al. |
| 2014/0303724 A1 | 10/2014 | Bluestein et al. |
| 2014/0309732 A1 | 10/2014 | Solem |
| 2014/0324161 A1 | 10/2014 | Tegels et al. |
| 2014/0350662 A1 | 11/2014 | Vaturi |
| 2014/0371789 A1 | 12/2014 | Hariton et al. |
| 2014/0379076 A1 | 12/2014 | Vidlund et al. |
| 2015/0005808 A1 | 1/2015 | Chouinard et al. |
| 2015/0005874 A1 | 1/2015 | Vidlund et al. |
| 2015/0039081 A1 | 2/2015 | Costello |
| 2015/0045880 A1 | 2/2015 | Hacohen |
| 2015/0051687 A1 | 2/2015 | Dickerhoff |
| 2015/0094802 A1 | 4/2015 | Buchbinder |
| 2015/0112188 A1 | 4/2015 | Stigall et al. |
| 2015/0119982 A1 | 4/2015 | Quill et al. |
| 2015/0127093 A1 | 5/2015 | Hosmer et al. |
| 2015/0142103 A1 | 5/2015 | Vidlund |
| 2015/0157457 A1 | 6/2015 | Hacohen |
| 2015/0173898 A1 | 6/2015 | Drasler et al. |
| 2015/0196390 A1 | 7/2015 | Ma et al. |
| 2015/0196391 A1 | 7/2015 | Dwork |
| 2015/0202044 A1 | 7/2015 | Chau et al. |
| 2015/0216661 A1 | 8/2015 | Hacohen et al. |
| 2015/0230919 A1 | 8/2015 | Chau et al. |
| 2015/0245934 A1 | 9/2015 | Lombardi et al. |
| 2015/0257878 A1 | 9/2015 | Lane et al. |
| 2015/0257880 A1 | 9/2015 | Bortlein et al. |
| 2015/0257882 A1 | 9/2015 | Bortlein et al. |
| 2015/0265400 A1 | 9/2015 | Eidenschink et al. |
| 2015/0272731 A1 | 10/2015 | Racchini et al. |
| 2015/0282922 A1 | 10/2015 | Hingston et al. |
| 2015/0282931 A1 | 10/2015 | Brunnett et al. |
| 2015/0289971 A1 | 10/2015 | Costello et al. |
| 2015/0289975 A1 | 10/2015 | Costello |
| 2015/0297241 A1 | 10/2015 | Yodfat et al. |
| 2015/0305867 A1 | 10/2015 | Liu et al. |
| 2015/0313701 A1 | 11/2015 | Krahbichler |
| 2015/0335424 A1 | 11/2015 | McLean et al. |
| 2015/0342717 A1 | 12/2015 | O'Donnell |
| 2015/0351904 A1 | 12/2015 | Cooper et al. |
| 2015/0351906 A1 | 12/2015 | Hammer et al. |
| 2015/0351910 A1 | 12/2015 | Gilmore et al. |
| 2015/0359629 A1 | 12/2015 | Ganesan et al. |
| 2016/0008130 A1 | 1/2016 | Hasin |
| 2016/0008131 A1 | 1/2016 | Christianson et al. |
| 2016/0022417 A1 | 1/2016 | Karapetian et al. |
| 2016/0030165 A1 | 2/2016 | Mitra et al. |
| 2016/0030167 A1 | 2/2016 | Delaloye et al. |
| 2016/0038283 A1 | 2/2016 | Divekar et al. |
| 2016/0045165 A1 | 2/2016 | Braido et al. |
| 2016/0045306 A1 | 2/2016 | Agrawal et al. |
| 2016/0045309 A1 | 2/2016 | Valdez et al. |
| 2016/0067031 A1 | 3/2016 | Kassab et al. |
| 2016/0081799 A1 | 3/2016 | Leo et al. |
| 2016/0095703 A1 | 4/2016 | Thomas |
| 2016/0095704 A1 | 4/2016 | Whitman |
| 2016/0113764 A1 | 4/2016 | Sheahan et al. |
| 2016/0113766 A1 | 4/2016 | Ganesan et al. |
| 2016/0113768 A1 | 4/2016 | Ganesan et al. |
| 2016/0143721 A1 | 5/2016 | Rosenbluth |
| 2016/0143730 A1 | 5/2016 | Kheradvar |
| 2016/0143735 A1 | 5/2016 | Subramanian et al. |
| 2016/0143739 A1 | 5/2016 | Horgan et al. |
| 2016/0158004 A1 | 6/2016 | Kumar et al. |
| 2016/0158007 A1 | 6/2016 | Centola et al. |
| 2016/0158008 A1 | 6/2016 | Miller et al. |
| 2016/0166382 A1 | 6/2016 | Nguyen |
| 2016/0184488 A1 | 6/2016 | Toyoda et al. |
| 2016/0194425 A1 | 7/2016 | Mitra et al. |
| 2016/0213470 A1 | 7/2016 | Ahlberg et al. |
| 2016/0213473 A1 | 7/2016 | Hacohen et al. |
| 2016/0220367 A1 | 8/2016 | Barrett |
| 2016/0220372 A1 | 8/2016 | Medema et al. |
| 2016/0220734 A1 | 8/2016 | Dyamenahalli |
| 2016/0228250 A1 | 8/2016 | Casley et al. |
| 2016/0235530 A1 | 8/2016 | Thomas et al. |
| 2016/0256269 A1 | 9/2016 | Cahalane et al. |
| 2016/0256270 A1 | 9/2016 | Folan et al. |
| 2016/0270911 A1 | 9/2016 | Ganesan et al. |
| 2016/0303804 A1 | 10/2016 | Grbic et al. |
| 2016/0310274 A1 | 10/2016 | Gross et al. |
| 2016/0317301 A1 | 11/2016 | Quadri et al. |
| 2016/0324639 A1 | 11/2016 | Nguyen et al. |
| 2016/0331534 A1 | 11/2016 | Buchbinder |
| 2016/0354201 A1 | 12/2016 | Keogh |
| 2016/0361169 A1 | 12/2016 | Gross et al. |
| 2016/0361184 A1 | 12/2016 | Tabor et al. |
| 2016/0367360 A1 | 12/2016 | Cartledge et al. |
| 2016/0367364 A1 | 12/2016 | Torrianni et al. |
| 2017/0000603 A1 | 1/2017 | Conklin et al. |
| 2017/0000604 A1 | 1/2017 | Conklin et al. |
| 2017/0020670 A1 | 1/2017 | Murray et al. |
| 2017/0035562 A1 | 2/2017 | Quadri et al. |
| 2017/0035568 A1 | 2/2017 | Lombardi et al. |
| 2017/0056166 A1 | 3/2017 | Ratz et al. |
| 2017/0056171 A1 | 3/2017 | Cooper |
| 2017/0071733 A1 | 3/2017 | Ghione et al. |
| 2017/0071736 A1 | 3/2017 | Zhu et al. |
| 2017/0076014 A1 | 3/2017 | Bressloff |
| 2017/0079786 A1 | 3/2017 | Li et al. |
| 2017/0079795 A1 | 3/2017 | Morrissey |
| 2017/0100246 A1 | 4/2017 | Rust et al. |
| 2017/0112620 A1 | 4/2017 | Curley et al. |
| 2017/0128208 A1 | 5/2017 | Christianson et al. |
| 2017/0143488 A1 | 5/2017 | Lashinski |
| 2017/0143489 A1 | 5/2017 | Lashinski |
| 2017/0165065 A1 | 6/2017 | Rothstein et al. |
| 2017/0172737 A1 | 6/2017 | Kuetting et al. |
| 2017/0181851 A1 | 6/2017 | Annest |
| 2017/0189177 A1 | 7/2017 | Schweich, Jr. |
| 2017/0196690 A1 | 7/2017 | Racchini et al. |
| 2017/0209266 A1 | 7/2017 | Lane et al. |
| 2017/0209268 A1 | 7/2017 | Cunningham et al. |
| 2017/0216026 A1 | 8/2017 | Quill et al. |
| 2017/0216030 A1 | 8/2017 | Jonsson |
| 2017/0224480 A1 | 8/2017 | Garde et al. |
| 2017/0224486 A1 | 8/2017 | Delaloye et al. |
| 2017/0231755 A1 | 8/2017 | Gloss et al. |
| 2017/0231760 A1 | 8/2017 | Lane et al. |
| 2017/0239047 A1 | 8/2017 | Quill et al. |
| 2017/0245993 A1 | 8/2017 | Gross et al. |
| 2017/0245994 A1 | 8/2017 | Khairkhahan et al. |
| 2017/0252163 A1 | 9/2017 | Kheradvar |
| 2017/0258584 A1 | 9/2017 | Chang et al. |
| 2017/0258585 A1 | 9/2017 | Marquez et al. |
| 2017/0273784 A1 | 9/2017 | Racchini et al. |
| 2017/0281337 A1 | 10/2017 | Campbell |
| 2017/0281341 A1 | 10/2017 | Lim et al. |
| 2017/0296340 A1 | 10/2017 | Gross et al. |
| 2017/0325948 A1 | 11/2017 | Wallace et al. |
| 2017/0325976 A1 | 11/2017 | Nguyen et al. |
| 2017/0333184 A1 | 11/2017 | Ryan |
| 2017/0333240 A1 | 11/2017 | Stangenes et al. |
| 2017/0348099 A1 | 12/2017 | Mendelson et al. |
| 2017/0348100 A1 | 12/2017 | Lane et al. |
| 2017/0360557 A1 | 12/2017 | Kheradvar et al. |

(56) References Cited

U.S. PATENT DOCUMENTS

| | | |
|---|---|---|
| 2017/0360558 A1 | 12/2017 | Ma |
| 2017/0360561 A1 | 12/2017 | Bell et al. |
| 2018/0021130 A1 | 1/2018 | Danino |
| 2018/0035971 A1 | 2/2018 | Brenner et al. |
| 2018/0042549 A1 | 2/2018 | Ho et al. |
| 2018/0042723 A1 | 2/2018 | Yellin et al. |
| 2018/0043133 A1 | 2/2018 | Wong |
| 2018/0049875 A1 | 2/2018 | Iflah et al. |
| 2018/0049876 A1 | 2/2018 | Miraki |
| 2018/0055628 A1 | 3/2018 | Patel et al. |
| 2018/0055633 A1 | 3/2018 | Costello et al. |
| 2018/0056045 A1 | 3/2018 | Donoghue et al. |
| 2018/0056046 A1 | 3/2018 | Kiersey et al. |
| 2018/0071088 A1 | 3/2018 | Badhwar et al. |
| 2018/0078367 A1 | 3/2018 | Saar et al. |
| 2018/0078368 A1 | 3/2018 | Vidlund et al. |
| 2018/0078370 A1 | 3/2018 | Kovalsky et al. |
| 2018/0085219 A1 | 3/2018 | Krivoruchko |
| 2018/0098837 A1 | 4/2018 | Shahriari |
| 2018/0099124 A1 | 4/2018 | Mcloughlin et al. |
| 2018/0116793 A1 | 5/2018 | Salahieh et al. |
| 2018/0116843 A1 | 5/2018 | Schreck et al. |
| 2018/0125642 A1 | 5/2018 | White et al. |
| 2018/0125654 A1 | 5/2018 | Duffy |
| 2018/0126127 A1 | 5/2018 | Devereux et al. |
| 2018/0133000 A1 | 5/2018 | Scheinblum et al. |
| 2018/0133006 A1 | 5/2018 | Jones et al. |
| 2018/0133011 A1 | 5/2018 | Perouse |
| 2018/0140417 A1 | 5/2018 | Sciscio et al. |
| 2018/0147041 A1 | 5/2018 | Chouinard et al. |
| 2018/0147055 A1 | 5/2018 | Vidlund et al. |
| 2018/0153689 A1 | 6/2018 | Maimon et al. |
| 2018/0161158 A1 | 6/2018 | Kovalsky et al. |
| 2018/0161161 A1 | 6/2018 | Yellin et al. |
| 2018/0168793 A1 | 6/2018 | Lees et al. |
| 2018/0177580 A9 | 6/2018 | Shemesh et al. |
| 2018/0177594 A1 | 6/2018 | Patel et al. |
| 2018/0185153 A1 | 7/2018 | Bishop et al. |
| 2018/0193138 A1 | 7/2018 | Vidlund |
| 2018/0200049 A1 | 7/2018 | Chambers et al. |
| 2018/0214141 A1 | 8/2018 | Mendez |
| 2018/0221016 A1 | 8/2018 | Conklin et al. |
| 2018/0243071 A1 | 8/2018 | Eigler et al. |
| 2018/0243532 A1 | 8/2018 | Willard et al. |
| 2018/0256322 A1 | 9/2018 | Zhang et al. |
| 2018/0256327 A1 | 9/2018 | Perszyk |
| 2018/0263767 A1 | 9/2018 | Chau et al. |
| 2018/0263773 A1 | 9/2018 | Poppe et al. |
| 2018/0280174 A1 | 10/2018 | Dwork |
| 2018/0289474 A1 | 10/2018 | Rajagopal et al. |
| 2018/0289475 A1 | 10/2018 | Chung et al. |
| 2018/0289485 A1 | 10/2018 | Rajagopal et al. |
| 2018/0296335 A1 | 10/2018 | Miyashiro |
| 2018/0296337 A1 | 10/2018 | Duhay et al. |
| 2018/0303488 A1 | 10/2018 | Hill |
| 2018/0311037 A1 | 11/2018 | Morriss et al. |
| 2018/0311474 A1 | 11/2018 | Tyler, II et al. |
| 2018/0318073 A1 | 11/2018 | Tseng et al. |
| 2018/0318078 A1 | 11/2018 | Willard |
| 2018/0325665 A1 | 11/2018 | Gurovich et al. |
| 2018/0325671 A1 | 11/2018 | Abunassar et al. |
| 2018/0338832 A1 | 11/2018 | Ganesan et al. |
| 2018/0344456 A1 | 12/2018 | Barash et al. |
| 2018/0353293 A1 | 12/2018 | Colavito et al. |
| 2018/0353295 A1 | 12/2018 | Cooper |
| 2018/0360439 A1 | 12/2018 | Niland et al. |
| 2018/0360599 A1 | 12/2018 | Drasler et al. |
| 2019/0000619 A1 | 1/2019 | Quijano et al. |
| 2019/0008640 A1 | 1/2019 | Cooper |
| 2019/0015188 A1 | 1/2019 | Eigler et al. |
| 2019/0021834 A1 | 1/2019 | Nir et al. |
| 2019/0029823 A1 | 1/2019 | Nguyen et al. |
| 2019/0038404 A1 | 2/2019 | Iamberger et al. |
| 2019/0038405 A1 | 2/2019 | Iamberger et al. |
| 2019/0053894 A1 | 2/2019 | Levi et al. |
| 2019/0053895 A1 | 2/2019 | Levi |
| 2019/0053897 A1 | 2/2019 | Levi et al. |
| 2019/0053898 A1 | 2/2019 | Maimon et al. |
| 2019/0053899 A1 | 2/2019 | Levi |
| 2019/0060051 A1 | 2/2019 | Scheeff et al. |
| 2019/0060057 A1 | 2/2019 | Cohen et al. |
| 2019/0060059 A1 | 2/2019 | Delgado et al. |
| 2019/0060069 A1 | 2/2019 | Maimon et al. |
| 2019/0060071 A1 | 2/2019 | Lane et al. |
| 2019/0070003 A1 | 3/2019 | Siegel et al. |
| 2019/0076233 A1 | 3/2019 | Fish |
| 2019/0076249 A1 | 3/2019 | Khairkhahan et al. |
| 2019/0083085 A1 | 3/2019 | Gilmore et al. |
| 2019/0091005 A1 | 3/2019 | Fifer et al. |
| 2019/0091015 A1 | 3/2019 | Dienno, V et al. |
| 2019/0091018 A1 | 3/2019 | Hariton et al. |
| 2019/0091022 A1 | 3/2019 | Yellin et al. |
| 2019/0099265 A1 | 4/2019 | Braido et al. |
| 2019/0099270 A1 | 4/2019 | Morrissey et al. |
| 2019/0105153 A1 | 4/2019 | Barash et al. |
| 2019/0117223 A1 | 4/2019 | Abunassar et al. |
| 2019/0117387 A1 | 4/2019 | Li et al. |
| 2019/0117391 A1 | 4/2019 | Humair |
| 2019/0117400 A1 | 4/2019 | Medema et al. |
| 2019/0117401 A1 | 4/2019 | Cortez, Jr. et al. |
| 2019/0125287 A1 | 5/2019 | Itou et al. |
| 2019/0125536 A1 | 5/2019 | Prabhu et al. |
| 2019/0133528 A1 | 5/2019 | Kassab et al. |
| 2019/0133756 A1 | 5/2019 | Zhang et al. |
| 2019/0133757 A1 | 5/2019 | Zhang et al. |
| 2019/0133765 A1 | 5/2019 | Yellin et al. |
| 2019/0142566 A1 | 5/2019 | Lansky et al. |
| 2019/0142582 A1 | 5/2019 | Drasler et al. |
| 2019/0150867 A1 | 5/2019 | Itou et al. |
| 2019/0151509 A1 | 5/2019 | Kheradvar et al. |
| 2019/0167423 A1 | 6/2019 | Hariton et al. |
| 2019/0167429 A1 | 6/2019 | Stearns et al. |
| 2019/0175338 A1 | 6/2019 | White et al. |
| 2019/0175339 A1 | 6/2019 | Vidlund |
| 2019/0175344 A1 | 6/2019 | Khairkhahan |
| 2019/0183639 A1 | 6/2019 | Moore |
| 2019/0183644 A1 | 6/2019 | Hacohen |
| 2019/0183648 A1 | 6/2019 | Trapp et al. |
| 2019/0192287 A1 | 6/2019 | Sandstrom et al. |
| 2019/0192296 A1 | 6/2019 | Schwartz et al. |
| 2019/0209317 A1 | 7/2019 | Zhang et al. |
| 2019/0209320 A1 | 7/2019 | Drasler et al. |
| 2019/0231523 A1 | 8/2019 | Lombardi et al. |
| 2019/0240020 A1 | 8/2019 | Rafiee et al. |
| 2019/0240022 A1 | 8/2019 | Rafiee et al. |
| 2019/0247050 A1 | 8/2019 | Goldsmith |
| 2019/0254815 A1 | 8/2019 | Bruchman |
| 2019/0254816 A1 | 8/2019 | Anderson et al. |
| 2019/0262118 A1 | 8/2019 | Eigler et al. |
| 2019/0262129 A1 | 8/2019 | Cooper |
| 2019/0269413 A1 | 9/2019 | Yodfat et al. |
| 2019/0269504 A1 | 9/2019 | Wang et al. |
| 2019/0269839 A1 | 9/2019 | Wilson et al. |
| 2019/0282360 A1 | 9/2019 | Colavito et al. |
| 2019/0290426 A1 | 9/2019 | Maimon et al. |
| 2019/0290427 A1 | 9/2019 | Mantanus et al. |
| 2019/0307563 A1 | 10/2019 | Sandstrom et al. |
| 2019/0307589 A1 | 10/2019 | Goldberg et al. |
| 2019/0388219 A1 | 12/2019 | Lane et al. |
| 2020/0121452 A1 | 4/2020 | Saikrishnan et al. |
| 2020/0121458 A1* | 4/2020 | Vidlund ......... A61F 2/2436 |
| 2020/0179146 A1* | 6/2020 | Christianson ......... A61F 2/2436 |
| 2020/0188097 A1 | 6/2020 | Perrin et al. |
| 2020/0237506 A1 | 7/2020 | Christianson et al. |
| 2020/0289259 A1* | 9/2020 | Christianson ......... A61F 2/2418 |
| 2020/0289263 A1 | 9/2020 | Christianson et al. |
| 2021/0000592 A1 | 1/2021 | Christianson et al. |
| 2021/0154011 A1 | 5/2021 | Christianson et al. |
| 2021/0186693 A1 | 6/2021 | Vidlund et al. |
| 2021/0220126 A1 | 7/2021 | Perrin |
| 2021/0220127 A1 | 7/2021 | Vidlund et al. |

(56) References Cited

U.S. PATENT DOCUMENTS

| | | | |
|---|---|---|---|
| 2021/0220134 A1 | 7/2021 | Christianson et al. | |
| 2021/0228349 A1 | 7/2021 | Vidlund et al. | |

FOREIGN PATENT DOCUMENTS

| | | |
|---|---|---|
| AU | 2011238752 A1 | 10/2012 |
| AU | 2011240940 A1 | 10/2012 |
| AU | 2012272855 A1 | 1/2014 |
| AU | 2011236036 B2 | 6/2014 |
| AU | 2011248657 B2 | 12/2014 |
| AU | 2016228261 A1 | 4/2017 |
| AU | 2017210659 A1 | 8/2017 |
| AU | 2013245201 B2 | 10/2017 |
| AU | 2014360294 B2 | 10/2017 |
| AU | 2016249819 A1 | 11/2017 |
| AU | 2016371525 A1 | 5/2018 |
| AU | 2016366783 A1 | 6/2018 |
| AU | 2017214672 B2 | 10/2018 |
| AU | 2017285993 A1 | 1/2019 |
| AU | 2014201920 B2 | 2/2019 |
| AU | 2015411406 B2 | 2/2019 |
| AU | 2019202290 A1 | 4/2019 |
| AU | 2017388857 A1 | 8/2019 |
| BR | PI0909379 B1 | 9/2019 |
| CA | 2531528 A1 | 1/2005 |
| CA | 2609800 A1 | 1/2007 |
| CA | 2822636 A1 | 10/2008 |
| CA | 2398948 C | 8/2009 |
| CA | 2813419 A1 | 4/2012 |
| CA | 2856088 A1 | 5/2013 |
| CA | 2866315 A1 | 9/2013 |
| CA | 2922123 A1 | 4/2015 |
| CA | 2504258 C | 6/2015 |
| CA | 2677648 C | 10/2015 |
| CA | 2815331 C | 10/2015 |
| CA | 2986584 A1 | 11/2015 |
| CA | 2975294 A1 | 8/2016 |
| CA | 2995603 A1 | 2/2017 |
| CA | 2753853 C | 4/2017 |
| CA | 2702615 C | 6/2017 |
| CA | 2744395 C | 8/2017 |
| CA | 3020238 A1 | 11/2017 |
| CA | 3033666 A1 | 2/2018 |
| CA | 3031572 A1 | 3/2018 |
| CA | 3022641 A1 | 5/2018 |
| CA | 3044062 A1 | 6/2018 |
| CA | 3048893 A1 | 7/2018 |
| CA | 3049792 A1 | 7/2018 |
| CA | 3046693 A1 | 8/2018 |
| CA | 2778944 C | 8/2019 |
| CN | 2855366 Y | 1/2007 |
| CN | 100584292 C | 1/2010 |
| CN | 101677820 A | 3/2010 |
| CN | 101677851 A | 3/2010 |
| CN | 102858272 A | 1/2013 |
| CN | 102869320 A | 1/2013 |
| CN | 102892384 A | 1/2013 |
| CN | 103118630 A | 5/2013 |
| CN | 103189015 A | 7/2013 |
| CN | 103228231 A | 7/2013 |
| CN | 103298426 A | 9/2013 |
| CN | 103370035 A | 10/2013 |
| CN | 103391756 A | 11/2013 |
| CN | 102245120 B | 8/2014 |
| CN | 104220027 A | 12/2014 |
| CN | 102917668 B | 1/2015 |
| CN | 104394803 A | 3/2015 |
| CN | 104582637 A | 4/2015 |
| CN | 102905647 B | 7/2015 |
| CN | 103648570 B | 9/2015 |
| CN | 104884000 A | 9/2015 |
| CN | 104160076 B | 12/2015 |
| CN | 105380730 A | 3/2016 |
| CN | 105451687 A | 3/2016 |
| CN | 105520792 A | 4/2016 |
| CN | 105530893 A | 4/2016 |
| CN | 102458309 B | 5/2016 |
| CN | 103200900 B | 5/2016 |
| CN | 105555232 A | 5/2016 |
| CN | 105578992 A | 5/2016 |
| CN | 103338709 B | 6/2016 |
| CN | 105658178 A | 6/2016 |
| CN | 105792780 A | 7/2016 |
| CN | 103347467 B | 8/2016 |
| CN | 103648439 B | 8/2016 |
| CN | 103889472 B | 8/2016 |
| CN | 105899150 A | 8/2016 |
| CN | 103153232 B | 9/2016 |
| CN | 106061437 A | 10/2016 |
| CN | 106068109 A | 11/2016 |
| CN | 106073946 A | 11/2016 |
| CN | 106255475 A | 12/2016 |
| CN | 103917194 B | 2/2017 |
| CN | 106456324 A | 2/2017 |
| CN | 106456325 A | 2/2017 |
| CN | 105073068 B | 3/2017 |
| CN | 106470641 A | 3/2017 |
| CN | 105451684 B | 4/2017 |
| CN | 106573129 A | 4/2017 |
| CN | 103945792 B | 5/2017 |
| CN | 106659394 A | 5/2017 |
| CN | 106716098 A | 5/2017 |
| CN | 106794063 A | 5/2017 |
| CN | 106890035 A | 6/2017 |
| CN | 106943207 A | 7/2017 |
| CN | 106999054 A | 8/2017 |
| CN | 106999281 A | 8/2017 |
| CN | 104114127 B | 9/2017 |
| CN | 107115161 A | 9/2017 |
| CN | 107249482 A | 10/2017 |
| CN | 107260366 A | 10/2017 |
| CN | 104918582 B | 11/2017 |
| CN | 107374783 A | 11/2017 |
| CN | 107427364 A | 12/2017 |
| CN | 106255476 B | 1/2018 |
| CN | 107530157 A | 1/2018 |
| CN | 107530167 A | 1/2018 |
| CN | 107530177 A | 1/2018 |
| CN | 107613908 A | 1/2018 |
| CN | 104869948 B | 2/2018 |
| CN | 107714240 A | 2/2018 |
| CN | 107920897 A | 4/2018 |
| CN | 104853696 B | 6/2018 |
| CN | 108135696 A | 6/2018 |
| CN | 108430392 A | 8/2018 |
| CN | 108472142 A | 8/2018 |
| CN | 106726007 B | 11/2018 |
| CN | 109124829 A | 1/2019 |
| CN | 109199641 A | 1/2019 |
| CN | 109561962 A | 4/2019 |
| CN | 109567991 A | 4/2019 |
| CN | 109862835 A | 6/2019 |
| CN | 109906063 A | 6/2019 |
| CN | 109996581 A | 7/2019 |
| CN | 110013358 A | 7/2019 |
| CN | 110290764 A | 9/2019 |
| DE | 102014102648 A1 | 9/2015 |
| DE | 102014102650 A1 | 9/2015 |
| DE | 102014102718 A1 | 9/2015 |
| DE | 102014102722 A1 | 9/2015 |
| DE | 202017104793 U1 | 11/2018 |
| DE | 202016008737 U1 | 4/2019 |
| DK | 2549953 T3 | 2/2017 |
| DK | 2254514 T3 | 12/2018 |
| EA | 027348 B1 | 7/2017 |
| EP | 0902704 A4 | 3/1999 |
| EP | 1301225 A2 | 4/2003 |
| EP | 1684666 A2 | 8/2006 |
| EP | 1996246 A2 | 12/2008 |
| EP | 2211779 A1 | 8/2010 |
| EP | 2254513 A1 | 12/2010 |
| EP | 2263605 A1 | 12/2010 |
| EP | 2273947 A1 | 1/2011 |
| EP | 2296744 A1 | 3/2011 |

(56) References Cited

FOREIGN PATENT DOCUMENTS

| | | |
|---|---|---|
| EP | 2379008 A2 | 10/2011 |
| EP | 2400926 A2 | 1/2012 |
| EP | 2427145 A2 | 3/2012 |
| EP | 1582178 B1 | 9/2012 |
| EP | 2542186 A2 | 1/2013 |
| EP | 2558030 A1 | 2/2013 |
| EP | 2560579 A1 | 2/2013 |
| EP | 2575681 A1 | 4/2013 |
| EP | 2603172 A2 | 6/2013 |
| EP | 2637607 A1 | 9/2013 |
| EP | 2651337 A2 | 10/2013 |
| EP | 2658476 A1 | 11/2013 |
| EP | 2699201 A1 | 2/2014 |
| EP | 2405966 B1 | 4/2014 |
| EP | 2055263 B1 | 6/2014 |
| EP | 2741711 A2 | 6/2014 |
| EP | 2793763 A1 | 10/2014 |
| EP | 2822503 A2 | 1/2015 |
| EP | 2538879 B1 | 4/2015 |
| EP | 2444031 B1 | 7/2015 |
| EP | 1702247 B1 | 8/2015 |
| EP | 2772228 B1 | 11/2015 |
| EP | 2943160 A2 | 11/2015 |
| EP | 2470098 B1 | 12/2015 |
| EP | 1991168 B1 | 1/2016 |
| EP | 2254512 B1 | 1/2016 |
| EP | 2964152 A1 | 1/2016 |
| EP | 2967853 A1 | 1/2016 |
| EP | 2967860 A1 | 1/2016 |
| EP | 2994073 A1 | 3/2016 |
| EP | 3001978 A1 | 4/2016 |
| EP | 3003187 A1 | 4/2016 |
| EP | 3007649 A1 | 4/2016 |
| EP | 3010447 A1 | 4/2016 |
| EP | 3017792 A1 | 5/2016 |
| EP | 3019092 A1 | 5/2016 |
| EP | 2563236 B1 | 6/2016 |
| EP | 3027143 A1 | 6/2016 |
| EP | 3037064 A1 | 6/2016 |
| EP | 2211758 B1 | 7/2016 |
| EP | 3052053 A1 | 8/2016 |
| EP | 3060140 A1 | 8/2016 |
| EP | 3062745 A1 | 9/2016 |
| EP | 3071149 A1 | 9/2016 |
| EP | 2282700 B1 | 11/2016 |
| EP | 2967854 B1 | 11/2016 |
| EP | 1998713 B1 | 12/2016 |
| EP | 3099271 A1 | 12/2016 |
| EP | 3100701 A1 | 12/2016 |
| EP | 3141219 A1 | 3/2017 |
| EP | 3157469 A1 | 4/2017 |
| EP | 2538880 B1 | 5/2017 |
| EP | 2967852 B1 | 6/2017 |
| EP | 3174503 A1 | 6/2017 |
| EP | 3182931 A1 | 6/2017 |
| EP | 2830536 B1 | 8/2017 |
| EP | 2830537 B1 | 9/2017 |
| EP | 2720642 B1 | 10/2017 |
| EP | 3232941 A1 | 10/2017 |
| EP | 3256076 A1 | 12/2017 |
| EP | 3281608 A1 | 2/2018 |
| EP | 2608815 B1 | 3/2018 |
| EP | 3310302 A1 | 4/2018 |
| EP | 3311778 A1 | 4/2018 |
| EP | 3337412 A1 | 6/2018 |
| EP | 3340931 A1 | 7/2018 |
| EP | 3344188 A1 | 7/2018 |
| EP | 3344197 A1 | 7/2018 |
| EP | 3345573 A1 | 7/2018 |
| EP | 2822473 B1 | 8/2018 |
| EP | 3354208 A1 | 8/2018 |
| EP | 3370649 A1 | 9/2018 |
| EP | 3372198 A1 | 9/2018 |
| EP | 3372199 A1 | 9/2018 |
| EP | 3375411 A1 | 9/2018 |
| EP | 2928538 B1 | 11/2018 |
| EP | 3399947 A1 | 11/2018 |
| EP | 3400913 A1 | 11/2018 |
| EP | 3406224 A1 | 11/2018 |
| EP | 2555709 B1 | 12/2018 |
| EP | 3417813 A1 | 12/2018 |
| EP | 3426188 A1 | 1/2019 |
| EP | 3429507 A1 | 1/2019 |
| EP | 3431040 A1 | 1/2019 |
| EP | 3432825 A1 | 1/2019 |
| EP | 3432834 A1 | 1/2019 |
| EP | 3437669 A1 | 2/2019 |
| EP | 3448312 A1 | 3/2019 |
| EP | 3454787 A1 | 3/2019 |
| EP | 2663259 B1 | 5/2019 |
| EP | 3302364 B1 | 5/2019 |
| EP | 3478224 A1 | 5/2019 |
| EP | 3484411 A1 | 5/2019 |
| EP | 3487420 A1 | 5/2019 |
| EP | 2560580 B1 | 6/2019 |
| EP | 3508113 A1 | 7/2019 |
| EP | 3518748 A1 | 8/2019 |
| EP | 3522830 A1 | 8/2019 |
| EP | 3528749 A1 | 8/2019 |
| EP | 3288495 B1 | 9/2019 |
| EP | 3538024 A1 | 9/2019 |
| EP | 3538025 A1 | 9/2019 |
| EP | 3019123 B1 | 10/2019 |
| EP | 3552584 A1 | 10/2019 |
| EP | 3552655 A1 | 10/2019 |
| ES | 2369241 T3 | 11/2011 |
| ES | 2647777 T3 | 12/2017 |
| ES | 2664243 T3 | 4/2018 |
| ES | 2675726 T3 | 7/2018 |
| GB | 2539444 A | 12/2016 |
| JP | 2003530956 A | 10/2003 |
| JP | 2005521513 A | 7/2005 |
| JP | 2008506459 A | 3/2008 |
| JP | 2008512211 A | 4/2008 |
| JP | 2009148579 A | 7/2009 |
| JP | 2009525138 A | 7/2009 |
| JP | 2009527316 A | 7/2009 |
| JP | 2009254864 A | 11/2009 |
| JP | 4426182 B2 | 3/2010 |
| JP | 2010518947 A | 6/2010 |
| JP | 2010537680 A | 12/2010 |
| JP | 2011510797 A | 4/2011 |
| JP | 2013503009 A | 1/2013 |
| JP | 2013505082 A | 2/2013 |
| JP | 2013508027 A | 3/2013 |
| JP | 2013512765 A | 4/2013 |
| JP | 2013523261 A | 6/2013 |
| JP | 2013527010 A | 6/2013 |
| JP | 2013543399 A | 12/2013 |
| JP | 2014501563 A | 1/2014 |
| JP | 2014505537 A | 3/2014 |
| JP | 5527850 B2 | 6/2014 |
| JP | 2014518697 A | 8/2014 |
| JP | 2014522678 A | 9/2014 |
| JP | 2015503948 A | 2/2015 |
| JP | 2015510819 A | 4/2015 |
| JP | 2015517854 A | 6/2015 |
| JP | 5767764 B2 | 8/2015 |
| JP | 5803010 B2 | 11/2015 |
| JP | 2015531283 A | 11/2015 |
| JP | 2015534887 A | 12/2015 |
| JP | 2016503710 A | 2/2016 |
| JP | 2016506794 A | 3/2016 |
| JP | 2016508858 A | 3/2016 |
| JP | 2016517748 A | 6/2016 |
| JP | 2016520391 A | 7/2016 |
| JP | 2016526438 A | 9/2016 |
| JP | 2016530046 A | 9/2016 |
| JP | 2016533787 A | 11/2016 |
| JP | 2016540617 A | 12/2016 |
| JP | 2017000729 A | 1/2017 |
| JP | 2017504410 A | 2/2017 |
| JP | 2017515609 A | 6/2017 |
| JP | 2017516536 A | 6/2017 |

(56) References Cited

FOREIGN PATENT DOCUMENTS

| | | |
|---|---|---|
| JP | 2017516609 A | 6/2017 |
| JP | 2017131738 A | 8/2017 |
| JP | 2017159055 A | 9/2017 |
| JP | 2017529908 A | 10/2017 |
| JP | 2018501001 A | 1/2018 |
| JP | 2018501901 A | 1/2018 |
| JP | 2018506412 A | 3/2018 |
| JP | 6329570 B2 | 5/2018 |
| JP | 2018515306 A | 6/2018 |
| JP | 2018118136 A | 8/2018 |
| JP | 2018532556 A | 11/2018 |
| JP | 2018535074 A | 11/2018 |
| JP | 2019500952 A | 1/2019 |
| JP | 2019501696 A | 1/2019 |
| JP | 2019501712 A | 1/2019 |
| JP | 6466853 B2 | 2/2019 |
| JP | 6480343 B2 | 3/2019 |
| JP | 2019507664 A | 3/2019 |
| JP | 6506813 B2 | 4/2019 |
| JP | 6526043 B2 | 6/2019 |
| JP | 2019103821 A | 6/2019 |
| JP | 2019514490 A | 6/2019 |
| JP | 2019516527 A | 6/2019 |
| JP | 2019517346 A | 6/2019 |
| JP | 6568213 B2 | 8/2019 |
| JP | 2019134972 A | 8/2019 |
| JP | 2019523090 A | 8/2019 |
| JP | 2019155178 A | 9/2019 |
| JP | 2019526303 A | 9/2019 |
| KR | 20010013991 A | 2/2001 |
| KR | 20120101625 A | 9/2012 |
| KR | 101223313 B1 | 1/2013 |
| KR | 101354189 B1 | 1/2014 |
| KR | 20140139060 A | 12/2014 |
| KR | 20150097757 A | 8/2015 |
| KR | 20160024992 A | 3/2016 |
| RU | 177405 U1 | 2/2018 |
| WO | WO-0044308 A2 | 8/2000 |
| WO | WO-03072287 A1 | 9/2003 |
| WO | WO-2004093728 A2 | 11/2004 |
| WO | WO-2006029062 A1 | 3/2006 |
| WO | WO-2006066150 A2 | 6/2006 |
| WO | WO-2007047945 A2 | 4/2007 |
| WO | WO-2007054015 A1 | 5/2007 |
| WO | WO-2007095233 A2 | 8/2007 |
| WO | WO-2007129220 A2 | 11/2007 |
| WO | WO-2008013915 A2 | 1/2008 |
| WO | WO-2008091925 A2 | 7/2008 |
| WO | WO-2008103280 A2 | 8/2008 |
| WO | WO-2009081396 A2 | 7/2009 |
| WO | WO-2009094188 A2 | 7/2009 |
| WO | WO-2009094189 A1 | 7/2009 |
| WO | WO-2009094197 A1 | 7/2009 |
| WO | WO-2009094501 A1 | 7/2009 |
| WO | WO-2009100242 A2 | 8/2009 |
| WO | WO-2010029190 A1 | 3/2010 |
| WO | WO-2010119110 A1 | 10/2010 |
| WO | WO-2011112706 A2 | 9/2011 |
| WO | WO-2011137531 A1 | 11/2011 |
| WO | WO-2012009558 A2 | 1/2012 |
| WO | WO 2012/035279 | 3/2012 |
| WO | WO-2012063228 A1 | 5/2012 |
| WO | WO-2012063242 A1 | 5/2012 |
| WO | WO-2012112469 A2 | 8/2012 |
| WO | WO-2012145545 A1 | 10/2012 |
| WO | WO-2012161786 A1 | 11/2012 |
| WO | WO-2012175483 A1 | 12/2012 |
| WO | WO-2012178115 A2 | 12/2012 |
| WO | WO-2013021375 A2 | 2/2013 |
| WO | WO-2013085719 A1 | 6/2013 |
| WO | WO-2013103612 A1 | 7/2013 |
| WO | WO-2013116785 A1 | 8/2013 |
| WO | WO-2013128436 A1 | 9/2013 |
| WO | WO-2013148019 A1 | 10/2013 |
| WO | WO-2013166356 A2 | 11/2013 |
| WO | WO-2013177684 A1 | 12/2013 |
| WO | WO-2013184945 A1 | 12/2013 |
| WO | WO-2014011330 A1 | 1/2014 |
| WO | WO-2014064695 A2 | 5/2014 |
| WO | WO-2014121042 A1 | 8/2014 |
| WO | WO-2014133667 A1 | 9/2014 |
| WO | WO-2014137805 A1 | 9/2014 |
| WO | WO-2014140230 A1 | 9/2014 |
| WO | WO-2014162306 A2 | 10/2014 |
| WO | WO-2014164151 A1 | 10/2014 |
| WO | WO-2014168655 A1 | 10/2014 |
| WO | WO-2015004173 A1 | 1/2015 |
| WO | WO-2015014960 A1 | 2/2015 |
| WO | WO-2015017075 A1 | 2/2015 |
| WO | WO-2015055605 A1 | 4/2015 |
| WO | WO-2015057735 A1 | 4/2015 |
| WO | WO-2015058039 A1 | 4/2015 |
| WO | WO-2015061021 A1 | 4/2015 |
| WO | WO-2015117025 A1 | 8/2015 |
| WO | WO-2015120122 A2 | 8/2015 |
| WO | WO-2015123607 A1 | 8/2015 |
| WO | WO-2015127264 A1 | 8/2015 |
| WO | WO-2015142834 A1 | 9/2015 |
| WO | WO-2015153755 A2 | 10/2015 |
| WO | WO-2016011267 A1 | 1/2016 |
| WO | WO-2016025733 A1 | 2/2016 |
| WO | WO-2016083351 A1 | 6/2016 |
| WO | WO-2016097337 A1 | 6/2016 |
| WO | WO-2016100799 A1 | 6/2016 |
| WO | WO-2016118851 A1 | 7/2016 |
| WO | WO-2016130913 A1 | 8/2016 |
| WO | WO-2016148777 A1 | 9/2016 |
| WO | WO-2016149083 A1 | 9/2016 |
| WO | WO-2016150806 A1 | 9/2016 |
| WO | WO-2016189391 A2 | 12/2016 |
| WO | WO-2017040684 A1 | 3/2017 |
| WO | WO-2017096157 A1 | 6/2017 |
| WO | WO-2017114928 A1 | 7/2017 |
| WO | WO-2017120404 A1 | 7/2017 |
| WO | WO-2017121193 A1 | 7/2017 |
| WO | WO-2017121194 A1 | 7/2017 |
| WO | WO-2017121195 A1 | 7/2017 |
| WO | WO-2017136596 A1 | 8/2017 |
| WO | WO-2017151292 A1 | 9/2017 |
| WO | WO-2017155892 A1 | 9/2017 |
| WO | WO-2017156352 A1 | 9/2017 |
| WO | WO-2017161204 A1 | 9/2017 |
| WO | WO-2017165842 A1 | 9/2017 |
| WO | WO-2017196511 A1 | 11/2017 |
| WO | WO-2017201082 A1 | 11/2017 |
| WO | WO-2017202042 A1 | 11/2017 |
| WO | WO-2017210356 A1 | 12/2017 |
| WO | WO-2017218375 A1 | 12/2017 |
| WO | WO-2018008019 A2 | 1/2018 |
| WO | WO-2018026445 A1 | 2/2018 |
| WO | WO-2018026904 A1 | 2/2018 |
| WO | WO-2018035105 A1 | 2/2018 |
| WO | WO-2018040244 A1 | 3/2018 |
| WO | WO-2018042439 A1 | 3/2018 |
| WO | WO-2018045156 A2 | 3/2018 |
| WO | WO-2018071115 A1 | 4/2018 |
| WO | WO-2018077143 A1 | 5/2018 |
| WO | WO-2018077146 A1 | 5/2018 |
| WO | WO-2018080328 A1 | 5/2018 |
| WO | WO-2018083493 A1 | 5/2018 |
| WO | WO-2018090576 A1 | 5/2018 |
| WO | WO-2018098032 A1 | 5/2018 |
| WO | WO-2018106460 A1 | 6/2018 |
| WO | WO-2018119304 A1 | 6/2018 |
| WO | WO-2018138658 A1 | 8/2018 |
| WO | WO-2018145055 A1 | 8/2018 |
| WO | WO-2018156767 A1 | 8/2018 |
| WO | WO-2018156922 A1 | 8/2018 |
| WO | WO-2018158747 A1 | 9/2018 |
| WO | WO-2018160790 A1 | 9/2018 |
| WO | WO-2018165358 A1 | 9/2018 |
| WO | WO-2018170149 A1 | 9/2018 |
| WO | WO-2018175220 A1 | 9/2018 |
| WO | WO-2018175619 A1 | 9/2018 |

(56) References Cited

FOREIGN PATENT DOCUMENTS

| | | |
|---|---|---|
| WO | WO-2018178208 A1 | 10/2018 |
| WO | WO-2018178977 A1 | 10/2018 |
| WO | WO-2018183832 A1 | 10/2018 |
| WO | WO-2018184225 A1 | 10/2018 |
| WO | WO-2018184226 A1 | 10/2018 |
| WO | WO-2018187495 A1 | 10/2018 |
| WO | WO-2018187753 A1 | 10/2018 |
| WO | WO-2018191681 A1 | 10/2018 |
| WO | WO-2018200531 A1 | 11/2018 |
| WO | WO-2018200942 A2 | 11/2018 |
| WO | WO-2018201111 A2 | 11/2018 |
| WO | WO-2018201212 A1 | 11/2018 |
| WO | WO-2018204106 A1 | 11/2018 |
| WO | WO-2018209302 A1 | 11/2018 |
| WO | WO-2018213209 A1 | 11/2018 |
| WO | WO-2018217525 A1 | 11/2018 |
| WO | WO-2018222799 A1 | 12/2018 |
| WO | WO-2018226628 A1 | 12/2018 |
| WO | WO-2019003221 A1 | 1/2019 |
| WO | WO-2019006383 A2 | 1/2019 |
| WO | WO-2019010458 A1 | 1/2019 |
| WO | WO-2019014473 A1 | 1/2019 |
| WO | WO-2019018319 A1 | 1/2019 |
| WO | WO-2019023385 A1 | 1/2019 |
| WO | WO-2019026059 A1 | 2/2019 |
| WO | WO-2019032992 A2 | 2/2019 |
| WO | WO-2019037579 A1 | 2/2019 |
| WO | WO-2019040357 A1 | 2/2019 |
| WO | WO-2019042472 A1 | 3/2019 |
| WO | WO-2019046099 A1 | 3/2019 |
| WO | WO-2019046205 A1 | 3/2019 |
| WO | WO-2019051168 A2 | 3/2019 |
| WO | WO-2019051180 A2 | 3/2019 |
| WO | WO-2019051587 A1 | 3/2019 |
| WO | WO-2019055577 A1 | 3/2019 |
| WO | WO-2019058178 A1 | 3/2019 |
| WO | WO-2019067219 A1 | 4/2019 |
| WO | WO-2019081689 A1 | 5/2019 |
| WO | WO-2019081985 A2 | 5/2019 |
| WO | WO-2019086958 A1 | 5/2019 |
| WO | WO-2019089136 A1 | 5/2019 |
| WO | WO-2019089821 A1 | 5/2019 |
| WO | WO-2019093387 A1 | 5/2019 |
| WO | WO-2019095049 A1 | 5/2019 |
| WO | WO-2019096033 A1 | 5/2019 |
| WO | WO-2019099722 A2 | 5/2019 |
| WO | WO-2019116322 A1 | 6/2019 |
| WO | WO-2019119674 A1 | 6/2019 |
| WO | WO-2019126518 A1 | 6/2019 |
| WO | WO-2019131148 A1 | 7/2019 |
| WO | WO-2019136162 A1 | 7/2019 |
| WO | WO-2019140293 A1 | 7/2019 |
| WO | WO-2019143775 A1 | 7/2019 |
| WO | WO-2019144036 A1 | 7/2019 |
| WO | WO-2019147585 A1 | 8/2019 |
| WO | WO-2019165213 A1 | 8/2019 |
| WO | WO-2019173475 A1 | 9/2019 |
| WO | WO 2019/195860 | 10/2019 |
| WO | WO-2019190800 A1 | 10/2019 |
| WO | WO-2019191102 A1 | 10/2019 |

OTHER PUBLICATIONS

International Search Report and Written Opinion for International Application No. PCT/US2019/051615, dated Mar. 2, 2020, 14 pages.
International Search Report and Written Opinion for International Application No. PCT/US2019/051957, dated Apr. 30, 2020, 16 pages.
Office Action for U.S. Appl. No. 16/155,890, dated Feb. 8, 2019, 13 pages.
Office Action for U.S. Appl. No. 16/448,108, dated Jan. 21, 2020, 14 pages.
Office Action for U.S. Appl. No. 16/448,108, dated Sep. 1, 2020, 14 pages.
Office Action for U.S. Appl. No. 16/455,417, dated Sep. 23, 2019, 11 pages.
International Search Report and Written Opinion for International Application No. PCT/US2019/067010, dated Mar. 10, 2020, 17 pages.
Office Action for U.S. Appl. No. 16/455,740, dated Jul. 24, 2020, 7 pages.
International Search Report and Written Opinion for International Application No. PCT/US2020/015231, dated Apr. 23, 2020, 10 pages.
International Search Report and Written Opinion for International Application No. PCT/US2020/021300, dated Oct. 7, 2020, 6 pages.
International Search Report and Written Opinion for International Application No. PCT/US2020/031390, dated Aug. 3, 2020, 10 pages.
International Search Report and Written Opinion for International Application No. PCT/US2020/013240, dated Jun. 3, 2020, 7 pages.
International Search Report and Written Opinion for International Application No. PCT/US2020/022828, dated May 19, 2020, 12 pages.
Office Action for U.S. Appl. No. 16/442,504, dated Jan. 14, 2020, 11 pages.
International Search Report and Written Opinion for International Application No. PCT/US2020/045195, dated Jan. 8, 2021, 18 pages.
International Search Report and Written Opinion for International Application No. PCT/US2020/047162, dated Dec. 30, 2020, 9 pages.
Office Action for U.S. Appl. No. 17/167,983, dated Apr. 13, 2021, 20 pages.
Office Action for U.S. Appl. No. 16/448,108, dated Mar. 8, 2021, 8 pages.
Office Action for U.S. Appl. No. 16/163,577, dated Mar. 8, 2021, 10 pages.
Office Action for U.S. Appl. No. 16/445,210, dated Jan. 28, 2021, 7 pages.
International Search Report and Written Opinion for International Application No. PCT/US2021/013570, dated Apr. 1, 2021, 9 pages.
International Search Report and Written Opinion for International Application No. PCT/US2019/028822, dated Oct. 24, 2019, 14 pages.
Office Action for U.S. Appl. No. 17/154,438, dated May 3, 2021, 16 pages.
Office Action for U.S. Appl. No. 17/193,936, dated May 27, 2021, 6 pages.
Office Action for U.S. Appl. No. 17/221,547, dated Aug. 4, 2021, 11 pages.
Office Action for U.S. Appl. No. 17/236,219, dated Aug. 4, 2021, 17 pages.
Office Action for U.S. Appl. No. 16/449,420, dated Sep. 1, 2021, 16 pages.
Office Action for U.S. Appl. No. 17/167,988, dated Sep. 22, 2021, 19 pages.
Office Action for U.S. Appl. No. 17/222,182, dated Sep. 2, 2021, 23 pages.

\* cited by examiner

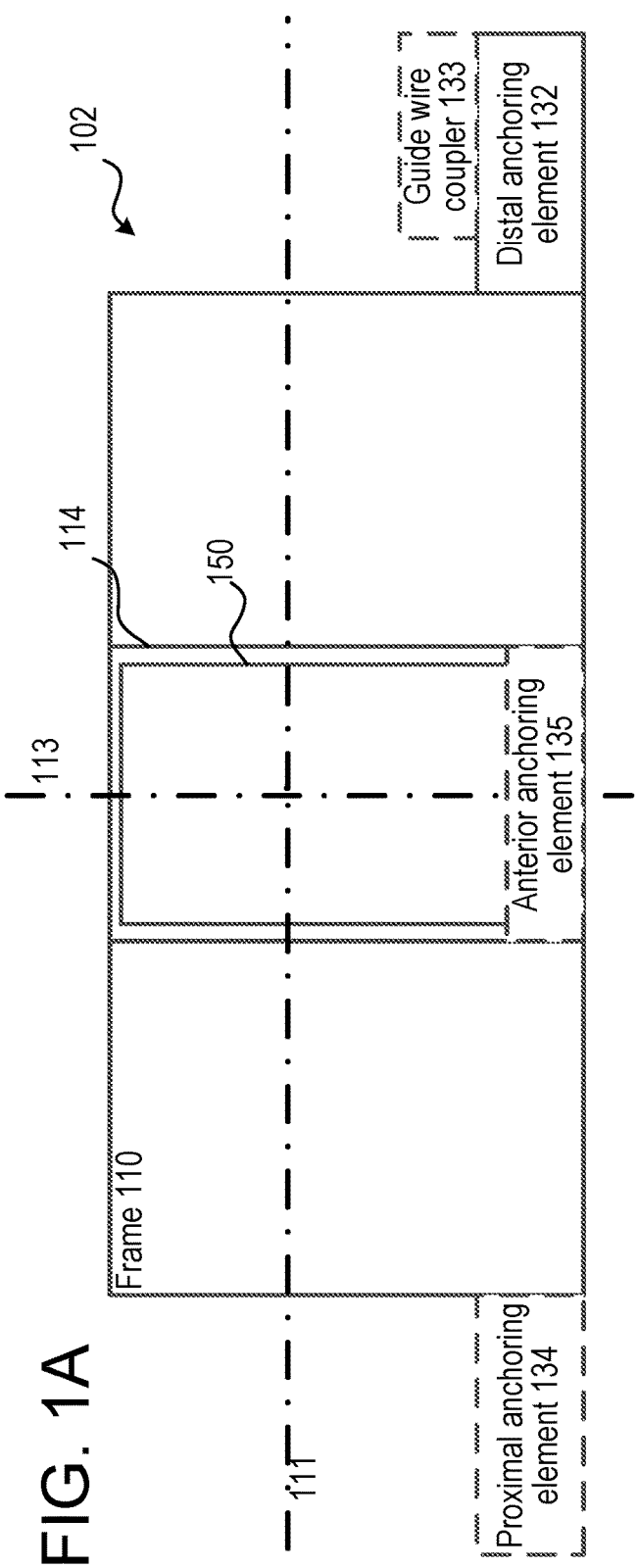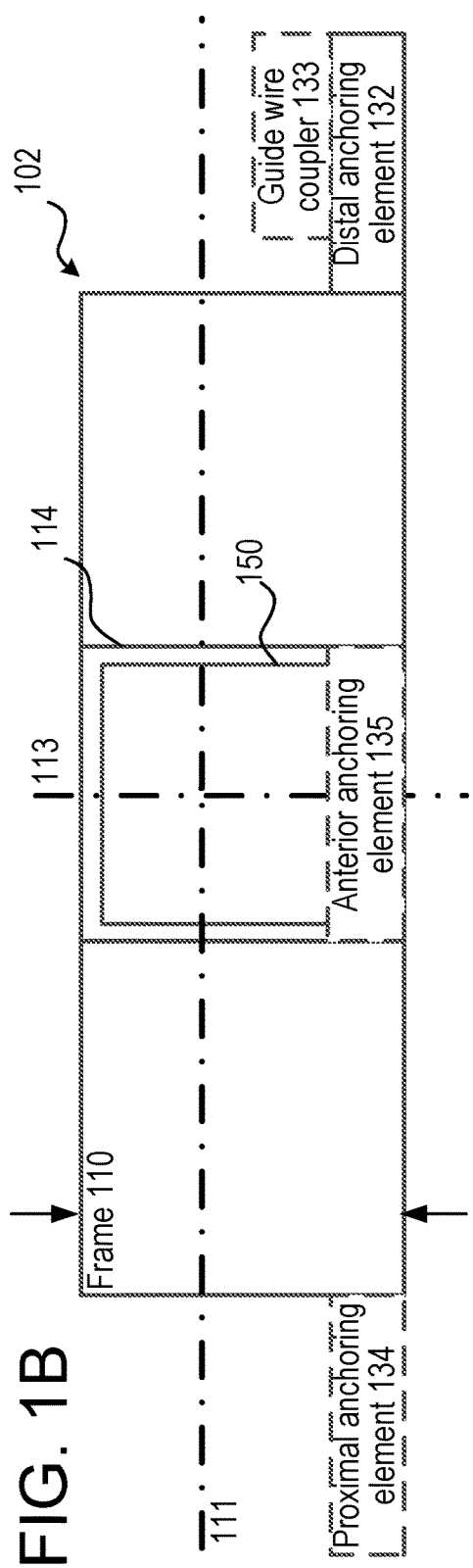

```
┌─────────────────────────────────────────────────────────────────┐
│ Advance a guide wire to an atrium, through a plane defined by an │
│ annulus of a native valve, and behind a native leaflet of the    │
│ native valve                                                     │
│ 11                                                               │
└─────────────────────────────────────────────────────────────────┘
                                │
                                ▼
┌─────────────────────────────────────────────────────────────────┐
│ Advance a prosthetic valve in an orthogonally compressed         │
│ configuration through a lumen of a delivery catheter and along   │
│ the guide wire and into the atrium                               │
│ 12                                                               │
└─────────────────────────────────────────────────────────────────┘
                                │
                                ▼
┌─────────────────────────────────────────────────────────────────┐
│ Release the prosthetic valve from the delivery catheter to allow │
│ at least a portion of the prosthetic valve to transition to an   │
│ expanded configuration with a distal anchoring element of the    │
│ prosthetic valve in an extended configuration                    │
│ 13                                                               │
└─────────────────────────────────────────────────────────────────┘
                                │
                                ▼
┌─────────────────────────────────────────────────────────────────┐
│ Advance the prosthetic valve along the guide wire to place the   │
│ distal anchoring element in a position behind the native leaflet │
│ and to seat the prosthetic valve in the annulus of the native    │
│ valve                                                            │
│ 14                                                               │
└─────────────────────────────────────────────────────────────────┘
                                │
                                ▼
┌─────────────────────────────────────────────────────────────────┐
│ Withdraw the guide wire to release the distal anchoring element  │
│ to a folded position allowing the distal anchoring element to    │
│ capture at least one of native leaflet or chordae and to secure  │
│ the native leaflet or chordae between the distal anchoring       │
│ element and a perimeter wall of the prosthetic valve             │
│ 15                                                               │
└─────────────────────────────────────────────────────────────────┘
```

SIDE-DELIVERABLE TRANSCATHETER PROSTHETIC VALVES AND METHODS FOR DELIVERING AND ANCHORING THE SAME

CROSS-REFERENCE TO RELATED APPLICATIONS

This application is a continuation of International Patent Application Serial No. PCT/US2020/022828, filed Mar. 13, 2020, entitled "Side-Deliverable Transcatheter Prosthetic Valves and Methods for Delivering and Anchoring the Same," the disclosure of which is incorporated herein by reference in its entirety.

International Patent Application Serial No. PCT/US2020//022828 is a continuation-in-part of U.S. patent application Ser. No. 16/438,434, filed Jun. 11, 2019, entitled "Distal Subannular Anchoring Tab for Side-Delivered Transcatheter Mitral Valve Prosthesis" (now U.S. Pat. No. 10,631,983), which claims priority to and the benefit of U.S. Provisional Patent Application Ser. No. 62/818,108, filed Mar. 14, 2019, entitled "Distal Anchoring Tab for Orthogonal Transcatheter Mitral Valve Prosthesis;" U.S. patent application Ser. No. 16/442,504, filed Jun. 16, 2019, entitled "A2 Clip for Side-Delivered Transcatheter Mitral Valve Prosthesis" (now U.S. Pat. No. 10,758,346), which claims priority to and the benefit of U.S. Provisional Patent Application Ser. No. 62/818,109, filed Mar. 14, 2019, entitled "A2 Clip for Orthogonal Transcatheter Mitral Valve Prosthesis;" and U.S. patent application Ser. No. 16/445,210, filed Jun. 19, 2019, entitled "Proximal, Distal, and Anterior Anchoring Tabs for Side-Delivered Transcatheter Mitral Valve Prosthesis," which claims priority to and the benefit of U.S. Provisional Patent Application Ser. No. 62/818,688, filed Mar. 14, 2019, entitled "Proximal, Distal, and Anterior Anchoring Tabs for Orthogonal Transcatheter Mitral Valve Prosthesis," the disclosures of which are incorporated herein by reference in their entireties.

International Patent Application Serial No. PCT/US2021/013570 also claims priority to and the benefit of U.S. Provisional Patent Application Ser. No. 62/818,742, filed Mar. 14, 2019, entitled "A1-P1 Targeting Guide Wire Delivery Systems for Orthogonal Transcatheter Mitral Valve Prosthesis," the disclosure of which is incorporated herein by reference in its entirety.

BACKGROUND

The embodiments described herein relate generally to transcatheter prosthetic valves and more particularly, to side-deliverable transcatheter prosthetic valves having one or more anchoring elements for securing the prosthetic valves in an annulus of a native valve and methods for delivering the same.

Prosthetic heart valves can pose challenges for delivery and deployment within a heart, particularly for delivery by catheters through the patient's vasculature rather than through a surgical approach. Delivery of traditional transcatheter prosthetic valves generally includes compressing the valve in a radial direction and loading the valve into a delivery catheter such that a central annular axis of the valve is parallel to a lengthwise axis of the delivery catheter. The valves are deployed from the end of the delivery catheter and expanded outwardly in a radial direction from the central annular axis. The expanded size (e.g., diameter) of traditional valves, however, can be limited by the internal diameter of the delivery catheter. The competing interest of minimizing delivery catheter size presents challenges to increasing the expanded diameter of traditional valves (e.g., trying to compress too much material and structure into too little space). Moreover, the orientation of the traditional valves during deployment can create additional challenges when trying to align the valves with the native valve annulus.

Some transcatheter prosthetic valves can be configured for side and/or orthogonal delivery, which can have an increased expanded diameter relative to traditional valves. For example, in side and/or orthogonal delivery, the valve and/or valve frame is compressed and loaded into a delivery catheter such that a central annular axis of the valve and/or valve frame is substantially orthogonal to the lengthwise axis of the delivery catheter, which can allow the valve to be compressed laterally and extended longitudinally (e.g., in a direction parallel to the lengthwise axis of the delivery catheter). In some such implementations, it is further desirable to provide an outer portion or valve frame that has a size and/or shape that corresponds to a size and/or shape of the annulus of the native valve (e.g., a mitral and/or a tricuspid valve of a human heart) while providing an inner flow control component that (i) is compatible with the lateral compression and/or longitudinal extension experienced during delivery and (ii) has a substantially cylindrical shape that allows for optimal function of the prosthetic valve leaflets included therein. With traditional and/or orthogonally delivered transcatheter prosthetic valves, it is also desirable to provide one or more ways of anchoring the valve in the native annuls without substantially increasing a compressed size of the valve.

Accordingly, a need exists for side-deliverable transcatheter prosthetic valves having one or more anchoring elements for securing the prosthetic valves in an annulus of a native valve and methods of delivering such prosthetic valves.

SUMMARY

The embodiments described herein are directed to side-deliverable transcatheter prosthetic valves having one or more anchoring elements for securing the prosthetic valves in an annulus of a native valve and methods for delivering the same. In some embodiments, a side-deliverable prosthetic heart valve includes an outer frame having a perimeter wall that circumscribes a central channel extending along a central axis and a flow control component mounted within the central channel. The flow control component includes an inner frame and a set of leaflets coupled to the inner frame. The prosthetic valve is foldable along a longitudinal axis and compressible along the central axis to place the prosthetic valve in a compressed configuration for delivery via a delivery catheter. The longitudinal axis is substantially parallel to a lengthwise axis of the delivery catheter when the prosthetic valve is disposed therein. The prosthetic valve is configured to transition to an expanded configuration when the prosthetic valve is released from the delivery catheter. The prosthetic valve further includes a distal anchoring element having a first end portion coupled to a distal side of the perimeter wall of the outer frame and a second end portion opposite the first end portion. The second end portion is configured to selectively engage a guide wire to allow the distal anchoring element to be advanced along the guide wire during deployment of the prosthetic valve. The distal anchoring element is in an extended configuration during deployment to allow the distal anchoring element to capture at least one of native leaflet or chordae. In response to the guide wire being disengaged from the second end portion, the distal anchoring element transitions to a folded configuration in which at least one of the native leaflet or the chordae is secured between the distal anchoring element and the distal side of the perimeter wall.

BRIEF DESCRIPTION OF THE DRAWINGS

FIGS. 1A and 1B are front view schematic illustrations of a side-delivered transcatheter prosthetic heart valve (also referred to herein as "prosthetic valve") according to an embodiment, and shown in an expanded configuration and a compressed configuration, respectively.

FIG. 45 is an illustration of a side view of a human heart having a trans-septal (trans-femoral/IVC or SVC) delivery catheter crossing from the right atrium to the left atrium for access to the mitral valve, according to an embodiment.

FIG. 66 is a flowchart illustrating a method of deploying a side deliverable transcatheter prosthetic heart valve in an annulus of a native valve, according to an embodiment.

DETAILED DESCRIPTION

Figure 1C:
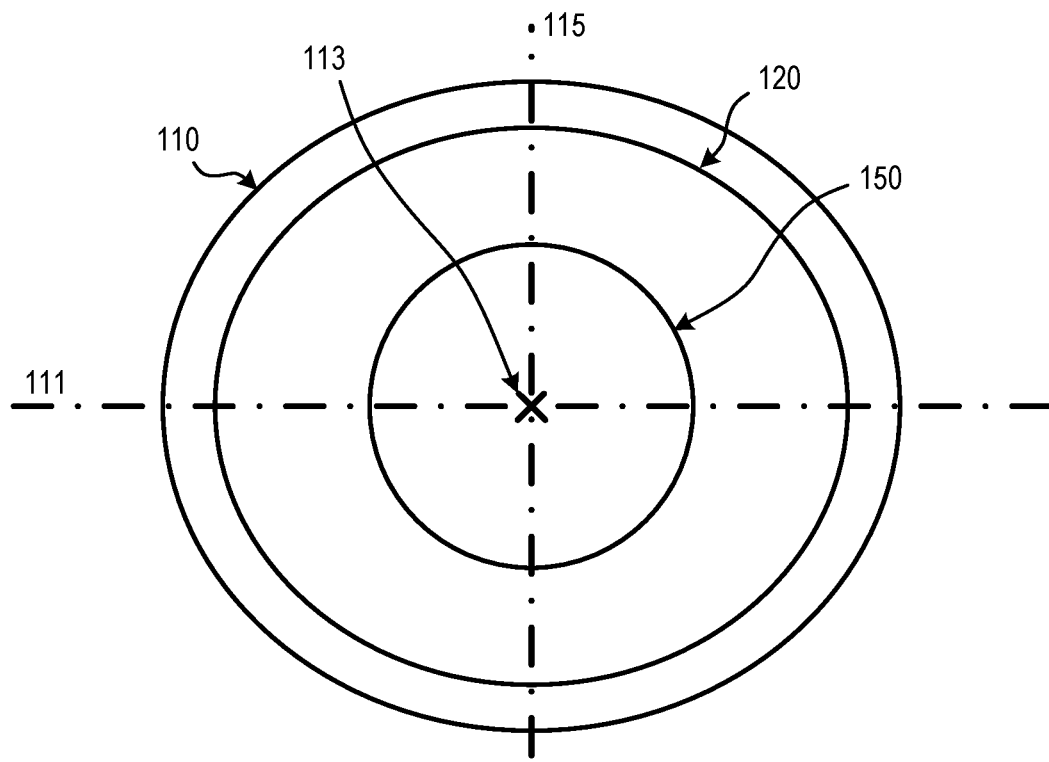
FIGS. 1C and 1D are top view schematic illustrations of the prosthetic valve of FIGS. 1A and 1B, and shown in the expanded configuration and the compressed configuration, respectively.

Disclosed embodiments are directed to transcatheter prosthetic heart valves and/or components thereof, and methods of manufacturing, loading, delivering, and/or deploying the transcatheter prosthetic valves and/or components thereof. In some embodiments, a side-deliverable prosthetic heart valve includes an outer frame having a perimeter wall that circumscribes a central channel extending along a central axis and a flow control component mounted within the central channel. The flow control component includes an inner frame and a set of leaflets coupled to the inner frame. The prosthetic valve is foldable along a longitudinal axis and compressible along the central axis to place the prosthetic valve in a compressed configuration for delivery via a delivery catheter. The longitudinal axis is substantially parallel to a lengthwise axis of the delivery catheter when the prosthetic valve is disposed therein. The prosthetic valve is configured to transition to an expanded configuration when the prosthetic valve is released from the delivery catheter. The prosthetic valve further includes a distal anchoring element having a first end portion coupled to a distal side of the perimeter wall of the outer frame and a second end portion opposite the first end portion. The second end portion is configured to selectively engage a guide wire to allow the distal anchoring element to be advanced along the guide wire during deployment of the prosthetic valve. The distal anchoring element is in an extended configuration during deployment to allow the distal anchoring element to capture at least one of native leaflet or chordae. In response to the guide wire being disengaged from the second end portion, the distal anchoring element transitions to a folded configuration in which at least one of the native leaflet or the chordae is secured between the distal anchoring element and the distal side of the perimeter wall.

In some embodiments, a side-deliverable prosthetic heart valve includes an outer frame having a perimeter wall that circumscribes a central channel extending along a central axis and a flow control component mounted within the central channel. The flow control component includes an inner frame and a set of leaflets coupled to the inner frame. The prosthetic valve is foldable along a longitudinal axis and compressible along the central axis to place the prosthetic valve in a compressed configuration for delivery via a delivery catheter. The longitudinal axis is substantially parallel to a lengthwise axis of the delivery catheter when the prosthetic valve is disposed therein. The prosthetic valve is configured to transition to an expanded configuration when the prosthetic valve is released from the delivery catheter. The prosthetic valve further includes a distal anchoring element coupled to a distal side of the perimeter wall of the outer frame and an anterior anchoring element coupled to an anterior side of the perimeter wall. The distal anchoring element is releasably coupled to a guide wire and is configured to be advanced along the guide wire when in an extended configuration to capture at least one of a distal native leaflet or distal chordae. The distal anchoring element transitions to a folded configuration when released from the guide wire to secure the distal native leaflet or the distal chordae between the distal anchoring element and the distal side of the perimeter wall. The anterior anchoring element includes a sleeve and an anterior clip at least partially disposed in the sleeve. The anterior clip can be transitioned between a first configuration in which the anterior clip extends from the sleeve in the direction of the central axis to allow the anterior clip to capture at least one of an anterior native leaflet or anterior chordae, and a second configuration in which the anterior clip is at least partially retracted into the sleeve to secure the anterior native leaflet or the anterior chordae between the anterior clip and the anterior side of the perimeter wall.

Any of the prosthetic heart valves described herein can be a relatively low profile, side-deliverable implantable prosthetic heart valve. Any of the prosthetic heart valves can be transcatheter prosthetic heart valves configured to be delivered into a heart via a delivery catheter. The prosthetic heart valves can have at least an annular outer valve frame and an inner flow control component (e.g., a 2-leaflet or 3-leaflet valve, sleeve, and/or the like) mounted in the valve frame. In addition, the prosthetic heart valves can include a single anchoring element or multiple anchoring elements configured to anchor the valve in the annulus of a native valve.

Any of the prosthetic heart valves described herein can be configured to transition between an expanded configuration and a compressed configuration. For example, any of the embodiments described herein can be a balloon-inflated prosthetic heart valve, a self-expanding prosthetic heart valve, and/or the like.

Any of the prosthetic heart valves described herein can be compressible—into the compressed configuration—in a lengthwise or orthogonal direction relative to the central axis of the flow control component that can allow a large diameter valve (e.g., having a height of about 5-60 mm and a diameter of about 20-80 mm) to be delivered and deployed from the inferior vena cava directly into the annulus of a native mitral or tricuspid valve using, for example, a 24-36 Fr delivery catheter and without delivery and deployment from the delivery catheter at an acute angle of approach.

Any of the prosthetic heart valves described herein can have a central axis that is coaxial or at least substantially parallel with blood flow direction through the valve. In some embodiments, the compressed configuration of the valve is orthogonal to the blood flow direction. In some embodiments, the compressed configuration of the valve is parallel to or aligned with the blood flow direction. In some embodiment, the valve can be compressed to the compressed configuration in two directions—orthogonal to the blood flow direction (e.g., laterally) and parallel to the blood flow (e.g., axially). In some embodiments, a long-axis or longitudinal axis is oriented at an intersecting angle of between 45-135 degrees to the first direction when in the compressed configuration and/or the expanded configuration.

Any of the prosthetic heart valves described herein can include an outer support frame that includes a set of compressible wire cells having an orientation and cell geometry substantially orthogonal to the central axis to minimize wire cell strain when the outer support frame is in a compressed configuration, a rolled and compressed configuration, or a folded and compressed configuration.

In some embodiments, an outer support frame has a lower body portion and an upper collar portion. The lower body portion forms a shape such as a funnel, cylinder, flat cone, or circular hyperboloid when the outer support frame is in an expanded configuration. In some embodiments, the outer support frame is formed from a wire, a braided wire, or a laser-cut wire frame, and is covered with a biocompatible material. The biocompatible material can be covered such that an inner surface is covered with pericardial tissue, an outer surface is covered with a woven synthetic polyester material, and/or both the inner surface is covered with pericardial tissue and the outer surface is covered with a woven synthetic polyester material.

In some embodiments, an outer support frame has a side profile of a flat cone shape having an outer diameter R of 40-80 mm, an inner diameter r of 20-60 mm, and a height of 5-60 mm. In some embodiments, an annular support frame has a side profile of an hourglass shape having a top diameter R1 of 40-80 mm, a bottom diameter R2 of 50-70 mm, an internal diameter r of 20-60 mm, and a height of 5-60 mm.

Any of the prosthetic heart valves described herein can include one or more anchoring element extending from a sidewall of a valve frame. For example, any of the prosthetic heart valves can include a distal anchoring element, which can be used, for example, as a Right Ventricular Outflow Tract ("RVOT") tab or a Left Ventricular Outflow Tract ("LVOT") tab. Any of the valves described herein can also include an anchoring element extending from a proximal sided of the valve frame, which can be used, for example, to anchor the valve to a proximal sub-annular space. Any of the valves described herein can also include an anterior or posterior anchoring element extended from an anterior or posterior side of the valve frame, respectively. The anchoring elements can include and/or can be formed from a wire loop or wire frame, an integrated frame section, and/or a stent, extending from about 10-40 mm away from the tubular frame.

Any of the prosthetic heart valves described herein can include (i) an upper anchoring element attached to a distal upper edge of the tubular frame, the upper anchoring element can include or be formed from a wire loop or wire frame extending from about 2-20 mm away from the tubular frame, and (ii) a lower anchoring element (e.g., used as a RVOT tab) extending from a distal side of the tubular frame, the lower anchoring element can include and/or can be formed from a wire loop or wire frame extending from about 10-40 mm away from the tubular frame.

Any of the prosthetic heart valves described herein can include a distal lower anchoring element configured to be positioned into the RVOT of the right ventricle and a proximal lower anchoring element configured to be positioned into a sub-annular position in contact with and/or adjacent to sub-annular tissue of the right ventricle. The transcatheter prosthetic heart valve can also include a distal upper anchoring element configured to be positioned into a supra-annular position in contact with and/or adjacent to supra-annular tissue of the right atrium. The distal upper anchoring element can provide a supra-annular downward force in the direction of the right ventricle and the distal and proximal lower anchoring elements can provide a sub-annular upward force in the direction of the right atrium.

Any of the prosthetic heart valves described herein can include an inner flow control component that has a leaflet frame with 2-4 flexible leaflets mounted thereon. The 2-4 leaflets are configured to permit blood flow in a first direction through an inflow end of the flow control component and block blood flow in a second direction, opposite the first direction, through an outflow end of the flow control component. The leaflet frame can include two or more panels of diamond-shaped or eye-shaped wire cells made from heat-set shape memory alloy material such as, for example, Nitinol. The leaflet frame can be configured to be foldable along a z-axis (e.g., a longitudinal axis) from a rounded or cylindrical configuration to a flattened cylinder configuration, and compressible along a vertical y-axis (e.g., a central axis) to a compressed configuration. In some implementations, the leaflet frame can include a pair of hinge areas, fold areas, connection points, etc. that can allow the leaflet frame to be folded flat along the z-axis prior to the leaflet frame being compressed along the vertical y-axis. The inner frame can be, for example, a single-piece structure with two or more living hinges (e.g., stress concentration riser and/or any suitable structure configured to allow for elastic/non-permanent deformation of the inner frame). In other implementations, the inner frame can be a two-piece structure where the hinge areas are formed using a secondary attachment method (e.g. sutures, fabrics, molded polymer components, etc.)

In some embodiments, the inner flow control component in an expanded configuration forms a shape such as a funnel, cylinder, flat cone, or circular hyperboloid. In some embodiments, the inner flow control component has a leaflet frame with a side profile of a flat cone shape having an outer diameter R of 20-60 mm, an inner diameter r of 10-50 mm, where diameter R is great than diameter r, and a height of 5-60 mm. In some embodiments, the leaflet frame is comprised of a wire, a braided wire, or a laser-cut wire. In some embodiments, the leaflet frame can have one or more longitudinal supports integrated into or mounted thereon and selected from rigid or semi-rigid posts, rigid or semi-rigid ribs, rigid or semi-rigid batons, rigid or semi-rigid panels, and combinations thereof.

Any of the prosthetic heart valves described herein and/or any component, feature, and/or aspect thereof can be similar to and/or substantially the same as the prosthetic heart valves (or components, features, and/or aspects thereof) described in International Patent Application No. PCT/US2019/051957, filed Sep. 19, 2019, entitled "Transcatheter Deliverable Prosthetic Heart Valves and Method of Delivery" (referred to herein as "the '957 PCT"), International Patent Application No. PCT/US2019/067010, filed Dec. 18, 2019, entitled "Transcatheter Deliverable Prosthetic Heart Valves and Methods of Delivery" (referred to herein as "the '010 PCT"), and/or International Patent Application No. PCT/US2020/015231, filed Jan. 27, 2020, "Collapsible Inner Flow Control Component for Side-Deliverable Transcatheter Heart Valve Prosthesis" (referred to herein as "the '231 PCT"), the disclosures of which are incorporated herein by reference in their entireties.

In some implementations, a prosthetic valve can be configured for deployment, for example, in an annulus of a native mitral valve. Use of a side-deliverable transcatheter mitral valve replacement allows a relatively large diameter valve to be delivered and deployed from the inferior vena cava trans-septally into the mitral valve without requiring an oversized diameter catheter and without requiring delivery and deployment from a catheter at an acute angle of approach.

In some embodiments, a prosthetic mitral valve can include one or more anchoring elements configured to secure the prosthetic valve in the native valve annulus. For example, a prosthetic mitral valve such as those described herein can include a distal anchoring element, a proximal anchoring element, and one or more anterior or posterior anchoring elements (e.g., an anterior A1, A2, or A3 anchoring element and/or a posterior P1, P2, or P3 anchoring element).

In some embodiments, a prosthetic mitral valve includes a distal anchoring tab that is (i) extended around a posterior leaflet and/or chordae using a guide wire to capture native mitral leaflet and/or chordae tissue and (ii) allowed to contract when the guide wire is withdrawn to pin the native tissue against a sidewall of the valve. In some embodiments, the valve further includes a proximal anchoring element configured to anchor a proximal side of the valve using a tab or loop deployed to the A3-P3 (proximal) commissure area of the native mitral valve. In some embodiments, the valve further includes an A2 clip that is similarly configured to extend or unfold (e.g., via a guide wire or self-actuation) to capture native mitral leaflet and/or chordae tissue and, upon withdrawal of the guide wire and/or otherwise upon retracting or re-folding the A2 clip, to pin the native tissue against the sidewall of the valve. In some embodiments, an A2 clip can be formed of a braided polyethylene, treated pericardial tissue, ePTFE, or Nitinol, and may have one or more radio-opaque markers.

In some embodiments, a delivery system for delivering a side-deliverable prosthetic heart valve can include a catheter that can deliver a guide wire directly to an A1-P1 commissure of a native mitral valve. In some implementations, targeting the A1-P1 commissure area, can allow a side deliverable valve such as those described herein to be directed to the target area via a delivery catheter for successful deployment of the valve.

Any of the delivery systems described herein can include a guide wire catheter that can be used independently of a valve delivery catheter. In some embodiments, the guide wire catheter has a custom shape, which articulates the distal tip of the guide wire catheter to the A1/P1 commissure pointing behind the posterior native leaflets. In some embodiments, the guide wire catheter can be used prior to insertion of the valve delivery catheter or can be threaded through the valve delivery catheter prior to loading the valve and can exit straight through the main lumen of through a side port in communication with the main lumen. After the guide wire is placed, the guide wire catheter can be removed from the patient.

Any of the delivery systems described herein can include a delivery catheter for a side-deliverable prosthetic heart valve that includes an outer shaft having an outer proximal end, an outer distal end, and an outer shaft lumen, wherein the outer distal end is closed with an atraumatic ball mounted thereon. The outer shaft lumen has an inner diameter of 8-10 mm sized for passage of a side delivered transcatheter prosthetic heart valve (e.g., a prosthetic tricuspid valve and/or a prosthetic mitral valve) therethrough.

Any method for manufacturing prosthetic heart valves described herein can include using additive or subtractive metal or metal-alloy manufacturing to produce a self-expanding outer support frame having a central channel and an outer perimeter wall circumscribing a central vertical axis. A collapsible flow control component is mounted within the outer support frame and configured to permit blood flow in a first direction through an inflow end of the valve and block blood flow in a second direction, opposite the first direction, through an outflow end of the valve. The flow control component has a leaflet frame with 2-4 flexible leaflets mounted. The leaflet frame can be formed using additive or subtractive metal or metal-alloy manufacturing. The additive metal or metal-alloy manufacturing can be 3D printing, direct metal laser sintering (powder melt), and/or the like. The subtractive metal or metal-alloy manufacturing is photolithography, laser sintering/cutting, CNC machining, electrical discharge machining, and/or the like. In some embodiments, a process of manufacturing can further include mounting the flow control component within the outer support frame, and covering an outer surface of the outer support frame with a pericardium material or similar biocompatible material.

Any method for delivering prosthetic heart valves described herein can include at least one of (i) compressing the valve along a central vertical axis to reduce a vertical dimension of the valve from top to bottom to place the valve in a compressed configuration, (ii) unilaterally rolling the valve into a compressed configuration from one side of the annular support frame, (iii) bilaterally rolling the valve into a compressed configuration from two opposing sides of the annular support frame, (iv) flattening the valve into two parallel panels that are substantially parallel to the long-axis, (v) flattening the valve into two parallel panels that are substantially parallel to the long-axis and then rolling the flattened valve into a compressed configuration, or (vi) flattening the valve into two parallel panels that are substantially parallel to the long-axis and then compressing the valve along a central vertical axis to reduce a vertical dimension of the valve from top to bottom to place the valve in a compressed configuration.

Any method for delivering prosthetic heart valves described herein can include orthogonal delivery of the prosthetic heart valve to a desired location in the body that includes (i) advancing a delivery catheter to the desired location in the body and (ii) delivering the prosthetic heart valve to the desired location in the body by releasing the valve from the delivery catheter. The valve is in a compressed configuration when in the delivery catheter and transitions to an expanded configuration when released from the delivery catheter.

Any method for delivering prosthetic heart valves described herein can include releasing the valve from the delivery catheter by (i) pulling the valve out of the delivery catheter using a pulling member (e.g., a wire or rod) that is releasably connected to a sidewall, a drum or collar, and/or an anchoring element (e.g., a distal anchoring element), wherein advancing the pulling member away from the delivery catheter pulls the compressed valve out of the delivery catheter, or (ii) pushing the valve out of the delivery catheter using a pushing member (e.g., a wire, rod, catheter, delivery member, etc.) that is releasably connected to a sidewall, a drum or collar, and/or an anchoring element (e.g., a distal anchoring element), wherein advancing the pushing member out of from the delivery catheter pushes the compressed valve out of the delivery catheter.

In some embodiments, a method for deploying a side-deliverable prosthetic heart valve to a patient includes advancing a guide wire to an atrium, through a plane defined by an annulus of a native valve, and behind a native leaflet of the native valve. The prosthetic valve is advanced in an orthogonally compressed configuration through a lumen of a delivery catheter and into the atrium. The prosthetic valve includes a distal anchoring element releasably coupled to the guide wire such that the prosthetic valve is advanced along a portion of the guide wire. The prosthetic valve is released from the delivery catheter to allow at least a portion of the prosthetic valve to transition to an expanded configuration such that the distal anchoring element is in an extended configuration after the releasing. The prosthetic valve is advanced along the guide wire to (i) place the distal anchoring element in a position behind the native leaflet and (ii) seat the prosthetic valve in the annulus of the native valve. The guide wire is withdrawn to release the distal anchoring element to a folded position allowing the distal anchoring element to capture at least one of native leaflet or chordae and to secure the native leaflet or chordae between the distal anchoring element and a perimeter wall of the prosthetic valve.

Any method for delivering and/or deploying prosthetic heart valves described herein can include releasing the valve from a delivery catheter while increasing blood flow during deployment of the valve by (i) partially releasing the valve from the delivery catheter to establish blood flow around the partially released valve and blood flow through the flow control component; (ii) completely releasing the valve from the delivery catheter while maintaining attachment to the valve to transition to a state with increased blood flow through the flow control component and decreased blood flow around the valve; (iii) deploying the valve into a final mounted position in a native annulus to transition to a state with complete blood flow through the flow control component and minimal or no blood flow around the valve; and (iv) disconnecting and withdrawing a positioning catheter, pulling or pushing wire or rod, and/or the delivery catheter.

Any method for delivering and/or deploying prosthetic heart valves described herein can include positioning the valve or a portion thereof in a desired position relative to the native tissue. For example, the method can include positioning a distal anchoring tab of the heart valve prosthesis into a ventricular outflow tract of the left or right ventricle. In some embodiments, the method can further include positioning an upper distal anchoring tab into a supra-annular position, where the upper distal anchoring tab provides a supra-annular downward force in the direction of the ventricle and the distal anchoring tab (e.g., the lower distal anchoring tab) provides a sub-annular upward force in the direction of the atrium. In some embodiments, the method can include rotating the heart valve prosthesis, using a steerable catheter, along an axis parallel to the plane of the valve annulus. In some embodiments, the method can include anchoring one or more tissue anchors attached to the valve into native tissue to secure the valve in a desired position.

Any method for delivering and/or deploying prosthetic heart valves described herein can include orthogonal delivery of the prosthetic heart valve to a native annulus of a human heart that includes at least one of (i) advancing a delivery catheter to the tricuspid valve or pulmonary artery of the heart through the inferior vena cava (IVC) via the femoral vein, (ii) advancing to the tricuspid valve or pulmonary artery of the heart through the superior vena cava (SVC) via the jugular vein, or (iii) advancing to the mitral valve of the heart through a trans-atrial approach (e.g., fossa ovalis or lower), via the IVC-femoral or the SVC jugular approach; and (iv) delivering and/or deploying the prosthetic heart valve to the native annulus by releasing the valve from the delivery catheter.

In some embodiments, a method for delivering and/or deploying prosthetic heart valves described herein to a native mitral valve can include advancing a guide wire trans-septally to the left atrium, through an annular plane at the A1/P1 commissure to a position behind a native posterior (e.g., P2) leaflet of a mitral valve of the patient. A delivery catheter containing the valve in an orthogonally compressed configuration is advanced to the left atrium of the patient a delivery catheter, wherein a distal anchoring tab of the valve is threaded onto the guide wire. In some embodiment, an A2 clip optionally may be threaded onto the guide wire. The valve is released from the delivery catheter, wherein the distal anchoring tab is in an open configuration and tracks over the guide wire during release. The valve is advanced over the guide wire to move the distal anchoring tab to the position behind the native posterior leaflet and to seat the valve into the native annulus. The guide wire is withdrawn to release the distal anchoring tab to the folded position allowing the tab to capture native leaflet and/or native chordae, and sandwich the native leaflet and/or chordae between the folded tab and an outer perimeter wall of the valve. In some embodiments, the method may optionally include withdrawing the guide wire to an A2 clip release position to release the A2 clip to the open position allowing the A2 clip to capture native leaflet and/or native chordae, and sandwich the native leaflet and/or chordae between the A2 clip and the perimeter wall of the annular support frame.

In some embodiments, the method can include delivering and/or deploying the valve, at least in part, via a single fixed curve catheter, a single deflectable catheter, an outer fixed curve catheter with an inner fixed curve catheter, an outer fixed curve catheter with an inner deflectable catheter, and an out deflectable catheter with an inner fixed curve catheter.

Any method for delivering and/or deploying prosthetic heart valves described herein and/or any portion thereof can be similar to and/or substantially the same as one or more methods for delivering and/or deploying prosthetic heart valves (or portion(s) thereof) described in the '957 PCT, the '010 PCT, and/or the '231 PCT.

The terminology used herein is for the purpose of describing particular embodiments only and is not intended to limit the full scope of the claims. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

As used herein, the singular forms "a," "an," and "the" are intended to include the plural forms as well, unless the context clearly indicates otherwise. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

In general, terms used herein, and especially in the appended claims (e.g., bodies of the appended claims) are generally intended as "open" terms (e.g., the term "including" should be interpreted as "including but not limited to," the term "having" should be interpreted as "having at least," etc.). Similarly, the terms "comprises" and/or "comprising," when used in this specification, specify the presence of stated features, integers (or fractions thereof), steps, operations, elements, and/or components, but do not preclude the presence or addition of one or more other features, integers (or fractions thereof), steps, operations, elements, components, and/or groups thereof. As used in this document, the term "comprising" means "including, but not limited to."

As used herein the term "and/or" includes any and all combinations of one or more of the associated listed items. It should be understood that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All ranges disclosed herein also encompass any and all possible subranges and combinations of subranges thereof unless expressly stated otherwise. Any listed range should be recognized as sufficiently describing and enabling the same range being broken down into at least equal subparts unless expressly stated otherwise. As will be understood by one skilled in the art, a range includes each individual member.

The term "valve prosthesis," "prosthetic heart valve," and/or "prosthetic valve" can refer to a combination of a frame and a leaflet or flow control structure or component, and can encompass both complete replacement of an anatomical part (e.g., a new mechanical valve replaces a native valve), as well as medical devices that take the place of and/or assist, repair, or improve existing anatomical parts (e.g., the native valve is left in place).

The disclosed valves include a member (e.g., a frame) that can be seated within a native valve annulus and can be used as a mounting element for a leaflet structure, a flow control component, or a flexible reciprocating sleeve or sleeve-valve. It may or may not include such a leaflet structure or flow control component, depending on the embodiment. Such members can be referred to herein as an "annular support frame," "tubular frame," "wire frame," "valve frame," "flange," "collar," and/or any other similar terms.

The term "flow control component" can refer in a non-limiting sense to a leaflet structure having 2-, 3-, 4-leaflets of flexible biocompatible material such a treated or untreated pericardium that is sewn or joined to a annular support frame, to function as a prosthetic heart valve. Such a valve can be a heart valve, such as a tricuspid, mitral, aortic, or pulmonary, that is open to blood flowing during diastole from atrium to ventricle, and that closes from systolic ventricular pressure applied to the outer surface. Repeated opening and closing in sequence can be described as "reciprocating." The flow control component is contemplated to include a wide variety of (bio)prosthetic artificial heart valves. Bioprosthetic pericardial valves can include bioprosthetic aortic valves, bioprosthetic mitral valves, bioprosthetic tricuspid valves, and bioprosthetic pulmonary valves.

Any of the disclosed valve embodiments may be delivered by a transcatheter approach. The term "transcatheter" is used to define the process of accessing, controlling, and/or delivering a medical device or instrument within the lumen of a catheter that is deployed into a heart chamber (or other desired location in the body), as well as an item that has been delivered or controlled by such as process. Transcatheter access is known to include cardiac access via the lumen of the femoral artery and/or vein, via the lumen of the brachial artery and/or vein, via lumen of the carotid artery, via the lumen of the jugular vein, via the intercostal (rib) and/or sub-xiphoid space, and/or the like. Moreover, transcatheter cardiac access can be via the inferior vena cava (IVC), superior vena cava (SVC), and/or via a trans-atrial (e.g., fossa ovalis or lower). Transcatheter can be synonymous with transluminal and is functionally related to the term "percutaneous" as it relates to delivery of heart valves. As used herein, the term "lumen" can refer to the inside of a cylinder or tube. The term "bore" can refer to the inner diameter of the lumen.

The mode of cardiac access can be based at least in part on "body channel" may be used to define a blood conduit or vessel within the body, the particular application of the disclosed embodiments of prosthetic valves determines the body channel at issue. An aortic valve replacement, for example, would be implanted in, or adjacent to, the aortic annulus. Likewise, a tricuspid or mitral valve replacement would be implanted at the tricuspid or mitral annulus. Certain features are particularly advantageous for one implantation site or the other. However, unless the combination is structurally impossible, or excluded by claim language, any of the valve embodiments described herein could be implanted in any body channel.

The term "expandable" as used herein may refer to a component of the heart valve capable of expanding from a first, delivery diameter to a second, implantation diameter. An expandable structure, therefore, does not mean one that might undergo slight expansion from a rise in temperature, or other such incidental cause. Conversely, "non-expandable" should not be interpreted to mean completely rigid or a dimensionally stable, as some slight expansion of conventional "non-expandable" heart valves, for example, may be observed.

Any of the disclosed valve embodiments may be delivered via traditional transcatheter delivery techniques or via orthogonal delivery techniques. For example, traditional delivery of prosthetic valves can be such that a central cylinder axis of the valve is substantially parallel to a length-wise axis of the delivery catheter. Typically, the valves are compressed in a radial direction relative to the central cylinder axis and advanced through the lumen of the delivery catheter. The valves are deployed from the end of the delivery catheter and expanded outwardly in a radial direction from the central cylinder axis.

As used herein the terms "side-delivered," "side-delivery," "orthogonal delivery," "orthogonally delivered," and/or so forth can be used interchangeably to describe such a delivery method and/or a valve delivered using such a method. Orthogonal delivery of prosthetic valves can be such that the central cylinder axis of the valve is substantially orthogonal to the length-wise axis of the delivery catheter. With orthogonal delivery, the valves are compressed (or otherwise reduced in size) in a direction substantially parallel to the central cylinder axis and/or in a lateral direction relative to the central cylinder axis. As such, a length-wise axis (e.g., a longitudinal axis) of an orthogonally delivered valve is substantially parallel to the length-wise axis of the delivery catheter. In other words, an orthogonally delivered prosthetic valve is compressed and/or delivered at a roughly 90 degree angle compared to traditional processes of compressing and delivering transcatheter prosthetic valves. Moreover, prosthetic valves configured to be orthogonally delivered and the processes of delivering such valves are described in detail in the '957 PCT and/or the '010 PCT incorporated by reference hereinabove.

Mathematically, the term "orthogonal" refers to an intersecting angle of 90 degrees between two lines or planes. As used herein, the term "substantially orthogonal" refers to an intersecting angle of 90 degrees plus or minus a suitable tolerance. For example, "substantially orthogonal" can refer to an intersecting angle ranging from 75 to 105 degrees.

As used herein, the term "tissue anchor" generally refers to a fastening device that connects a portion of an outer frame of a prosthetic to native annular tissue, usually at or near a periphery of a collar of the prosthetic valve. The tissue anchor may be positioned to avoid piercing tissue and just rely on the compressive force of the two plate-like collars on the captured tissue, or a tissue anchor (with or without an integrated securement wire) may pierce through native tissue to provide anchoring, or a combination of both. The tissue anchor may have a securement mechanism, such as a pointed tip, a groove, a flanged shoulder, a lock, one or more apertures, and/or the like. In some embodiments, a securement mechanism can be attached or anchored to a portion of an outer frame by any attachment or anchoring mechanisms, including a knot, a suture, a wire crimp, a wire lock, a cam mechanism, or combinations.

Any of the prosthetic valves and/or components thereof may be fabricated from any suitable biocompatible material or combination of materials. For example, an outer valve frame, an inner valve frame (e.g., of an inner flow control component), and/or components thereof may be fabricated from biocompatible metals, metal alloys, polymer coated metals, and/or the like. Suitable biocompatible metals and/or metal alloys can include stainless steel (e.g., 316 L stainless steel), cobalt chromium (Co—Cr) alloys, nickel-titanium alloys (e.g., Nitinol®), and/or the like. Moreover, any of the outer or inner frames described herein can be formed from superelastic or shape-memory alloys such as nickel-titanium alloys (e.g., Nitinol®). Suitable polymer coatings can include polyethylene vinyl acetate (PEVA), poly-butyl methacrylate (PBMA), translute Styrene Isoprene Butadiene (SIBS) copolymer, polylactic acid, polyester, polylactide, D-lactic polylactic acid (DLPLA), polylactic-co-glycolic acid (PLGA), and/or the like. Some such polymer coatings may form a suitable carrier matrix for drugs such as, for example, Sirolimus, Zotarolimus, Biolimus, Novolimus, Tacrolimus, Paclitaxel, Probucol, and/or the like.

Some biocompatible synthetic material(s) can include, for example, polyesters, polyurethanes, polytetrafluoroethylene (PTFE) (e.g., Teflon), and/or the like. Where a thin, durable synthetic material is contemplated (e.g., for a covering), synthetic polymer materials such expanded PTFE or polyester may optionally be used. Other suitable materials may optionally include elastomers, thermoplastics, polyurethanes, thermoplastic polycarbonate urethane, polyether urethane, segmented polyether urethane, silicone polyether urethane, polyetheretherketone (PEEK), silicone-polycarbonate urethane, polypropylene, polyethylene, low-density polyethylene (LDPE), high-density polyethylene (HDPE), ultra-high density polyethylene (UHDPE), polyolefins, polyethylene-glycols, polyethersulphones, polysulphones, polyvinylpyrrolidones, polyvinylchlorides, other fluoropolymers, polyesters, polyethylene-terephthalate (PET) (e.g., Dacron), Poly-L-lactic acids (PLLA), polyglycolic acid (PGA), poly(D, L-lactide/glycolide) copolymer (PDLA), silicone polyesters, polyamides (Nylon), PTFE, elongated PTFE, expanded PTFE, siloxane polymers and/or oligomers, and/or polylactones, and block co-polymers using the same.

Any of the outer valve frames, inner valve frames (e.g., of the flow control components), and/or portions or components thereof can be internally or externally covered, partially or completely, with a biocompatible material such as pericardium. A valve frame may also be optionally externally covered, partially or completely, with a second biocompatible material such as polyester or Dacron®. Disclosed embodiments may use tissue, such as a biological tissue that is a chemically stabilized pericardial tissue of an animal, such as a cow (bovine pericardium), sheep (ovine pericardium), pig (porcine pericardium), or horse (equine pericardium). Preferably, the tissue is bovine pericardial tissue. Examples of suitable tissue include that used in the products Duraguard®, Peri-Guard®, and Vascu-Guard®, all products currently used in surgical procedures, and which are marketed as being harvested generally from cattle less than 30 months old.

The embodiments herein, and/or the various features or advantageous details thereof, are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein. Rather, these embodiments are provided so that this disclosure will be thorough and complete, and will fully convey the scope of the inventive concepts to those skilled in the art. Like numbers refer to like elements throughout.

FIGS. 1A-1E are various schematic illustrations of a transcatheter prosthetic valve 102 according to an embodiment. The transcatheter prosthetic valve 102 is configured to be deployed in a desired location within a body (e.g., of a human patient) and to permit blood flow in a first direction through an inflow end of the transcatheter prosthetic valve 102 and to block blood flow in a second direction, opposite the first direction, through an outflow end of the transcatheter prosthetic valve 102. For example, the transcatheter prosthetic valve 102 can be a transcatheter prosthetic heart valve configured to be deployed within the annulus of a native tricuspid valve or native mitral valve of a human heart to supplement and/or replace the functioning of the native valve.

The transcatheter prosthetic valve 102 (also referred to herein as "prosthetic valve" or simply "valve") is compressible and expandable in at least one direction relative to a long-axis 111 of the valve 102 (also referred to herein as "horizontal axis," "longitudinal axis," or "lengthwise axis"). The valve 102 is compressible and expandable between an expanded configuration (FIGS. 1A, 1C, and 1E) for implanting at a desired location in a body (e.g., a human heart) and a compressed configuration (FIGS. 1B and 1D) for introduction into the body using a delivery catheter 172.

In some embodiments, the valve 102 can be centric, or radially symmetrical. In other embodiments, the valve 102 can be eccentric, or radially asymmetrical relative to the y-axis or a central axis 113. In some eccentric embodiments, the valve 102 (or an outer frame thereof) may have a D-shape (viewed from the top) so the flat portion can be matched to the anatomy in which the valve 102 will be deployed. For example, in some instances, the valve 102 may be deployed in the tricuspid annulus and may have a complex shape determined by the anatomical structures where the valve 102 is being mounted. In the tricuspid annulus, the circumference of the tricuspid valve may be a rounded ellipse, the septal wall is known to be substantially vertical, and the tricuspid is known to enlarge in disease states along the anterior-posterior line. In other instances, the valve 102 may be deployed in the mitral annulus (e.g., near the anterior leaflet) and may have a complex shape determined by the anatomical structures where the valve 102 is being mounted. For example, in the mitral annulus, the circumference of the mitral valve may be a rounded ellipse, the septal wall is known to be substantially vertical, and the mitral is known to enlarge in disease states.

In some embodiments, the valve 102 (and/or at least a portion thereof) may start in a roughly tubular configuration, and may be heat-shaped and/or otherwise formed into any desired shape. In some embodiments, the valve 102 can include an upper atrial cuff or flange for atrial sealing and a lower transannular section (e.g., a body section, a tubular section, a cylindrical section, etc.) having an hourglass cross-section for about 60-80% of the circumference to conform to the native annulus along the posterior and anterior annular segments while remaining substantially vertically flat along 20-40% of the annular circumference to conform to the septal annular segment. While the valve 102 is shown in FIGS. 1A-1E as having a given shape, it should be understood that the size and/or shape of the valve 102 (and/or at least a portion thereof) can be based on a size and/or shape of the anatomical structures of the native tissue.

As shown, the valve 102 generally includes an annular support frame 110 and a flow control component 150. In addition, the valve 102 and/or at least the annular support frame 110 of the valve 102 optionally can include one or more anchoring element. For example, in the embodiment shown in FIGS. 1A-1E, the annular support frame 110 includes at least a distal anchoring element 132. In other embodiments, the annular support frame 110 can optionally include a proximal anchoring element 134, an anterior anchoring element 135, and/or any other suitable anchoring element (not shown in FIGS. 1A-1E). In some implementations, the distal anchoring element 132, the proximal anchoring element 134, and the anterior anchoring elements 135 can be lower anchoring elements and the valve 102 and/or the annular support frame 110 can include one or more upper anchoring elements (e.g., a distal upper anchoring element, a proximal upper anchoring element, and/or the like (not shown)). In some implementations, the valve 102 and/or aspects or portions thereof can be similar to and/or substantially the same as the valves (and/or the corresponding aspects or portions thereof) described in detail in the '957 PCT, the '010 PCT, and/or the '231 PCT incorporated by reference hereinabove. Accordingly, certain aspects, portions, and/or details of the valve 102 may not be described in further detail herein.

The annular support frame 110 (also referred to herein as "tubular frame," "valve frame," "wire frame," "outer frame," or "frame") can have or can define an aperture or central channel 114 that extends along the central axis 113 (e.g., the y-axis). The central channel 114 (e.g., a central axial lumen or channel) can be sized and configured to receive the flow control component 150 across a portion of a diameter of the central channel 114. The frame 110 may have an outer circumferential surface for engaging native annular tissue that may be tensioned against an inner aspect of the native annulus to provide structural patency to a weakened native annular ring.

The frame 110 includes a cuff or collar (not shown) and a transannular, body, and/or tubular section (not shown). The cuff or collar (referred to herein as "collar") can be attached to and/or can form an upper edge of the frame 110. When the valve 102 is deployed within a human heart, the collar can be an atrial collar. The collar can be shaped to conform to the native deployment location. In a mitral valve replacement, for example, the collar can have varying portions to conform to the native valve and/or a portion of the atrial floor surrounding the mitral valve. In some embodiments, the collar can have a distal and proximal upper collar portion. The distal collar portion can be larger than the proximal upper collar portion to account for annular geometries, supra-annular geometries, and/or subannular geometries. Examples of collars are described below with reference to specific embodiments.

The frame 110 may optionally have a separate atrial collar attached to the upper (atrial) edge of the frame 110, for deploying on the atrial floor that is used to direct blood from the atrium into the flow control component 150 and to seal against blood leakage (perivalvular leakage) around the frame 110. The frame 110 may also optionally have a separate ventricular collar attached to the lower (ventricular) edge of the frame 110, for deploying in the ventricle immediately below the native annulus that is used to prevent regurgitant leakage during systole, to prevent dislodging of the valve 102 during systole, to sandwich or compress the native annulus or adjacent tissue against the atrial cuff or collar, and/or optionally to attach to and support the flow control component 150. Some embodiments may have both an atrial collar and a ventricular collar, whereas other embodiments either include a single atrial collar, a single ventricular collar, or have no additional collar structure. In some embodiments, an atrial collar and/or ventricular collar can be formed separately from the transannular or body section of the frame 110 and can be coupled to the transannular section via any suitable coupling method (e.g., sewn, bound, welded, etc.). In other embodiments, an atrial collar and/or a ventricular collar can be unitarily and/or monolithically formed with the transannular or body section of the frame 110.

The frame 110 and/or at least the transannular or body section thereof can be a ring, a cylindrical tube, a conical tube, D-shaped tube, and/or any other suitable annular shape. In some embodiments, the frame 110 and/or at least the transannular or body section thereof may have a side profile of a flat-cone shape, an inverted flat-cone shape (narrower at top, wider at bottom), a concave cylinder (walls bent in), a convex cylinder (walls bulging out), an angular hourglass, a curved, graduated hourglass, a ring or cylinder having a flared top, flared bottom, or both. The frame 110 may have a height in the range of about 5-60 mm, may have an outer diameter dimension, R, in the range of about 20-80 mm, and may have an inner diameter dimension in the range of about 21-79 mm, accounting for the thickness of the frame 110 (e.g., a wire material forming the frame 110).

The frame 110 is compressible for delivery and when released it is configured to return to its original (uncompressed) shape. The frame 110 may be constructed as a wire, a braided wire, or a laser cut wire frame. In some embodiments, the frame 110 can include and/or can form a set of compressible wire cells having an orientation and cell geometry substantially orthogonal to the central vertical axis 113 to minimize wire cell strain when the frame 110 is in a vertical compressed configuration, a rolled and compressed configuration, or a folded and compressed configuration. In some implementations, the frame 110 can include and/or can be formed of a shape-memory element allowing the frame 110 to be self-expanding. In some instances, suitable shape-memory materials can include metals and/or plastics that are durable and biocompatible. For example, the frame 110 can be made from superelastic metal wire, such as a Nitinol wire or other similarly functioning material. In some embodiments, the frame 110 can be formed from stainless steel, cobalt-chromium, titanium, and/or other functionally equivalent metals and/or alloys. In other embodiments, the frame 110 can be formed from any suitable material and can be expandable from the compressed configuration using a transcatheter expansion balloon and/or the like.

The frame 110 may also have and/or form additional functional elements (e.g., loops, anchors, etc.) for attaching accessory components such as biocompatible covers, tissue anchors, releasable deployment and retrieval control guides, knobs, attachments, rigging, and so forth. The frame 110 may be optionally internally or externally covered, partially or completely, with a biocompatible material such as pericardium, polyester, Dacron®, and/or the like. In some implementations, the frame 110 (or aspects and/or portions thereof) can be structurally and/or functionally similar to the frames (or corresponding aspects and/or portions thereof) described in detail in the '957 PCT, the '010 PCT, and/or the '231 PCT.

As described above, the frame 110 and/or the valve 102 can include at least a distal anchoring element 132. In some embodiments, the frame 110 and/or the valve 102 can include the distal anchoring element 132 as well as the proximal anchoring element 134 and/or the anterior anchoring element 135. The anchoring elements of the valve 102 and/or the frame 110 can be any suitable shape, size, and/or configuration such as any of those described in detail in the '957 PCT, the '010 PCT, the '231 PCT, and/or any of those described herein with respect to specific embodiments. For example, the distal, proximal, and anterior anchoring elements 132, 134, and 135 can be lower anchoring elements (e.g., coupled to and/or included in a lower portion of the frame 110). In some embodiments, the frame 110 and/or the valve 102 can also optionally include one or more of a distal upper anchoring element, one or more proximal upper anchoring element, and/or any other suitable anchoring element(s). The anchoring elements of the frame 110 can include and/or can be formed from a wire loop or wire frame, an integrated frame section, and/or a stent, extending about 10-40 mm away from the frame 110.

In some embodiments, the frame 110 can optionally include a guide wire coupler 133 configured to selectively engage and/or receive a portion of a guide wire or a portion of a guide wire assembly. In certain embodiments, the distal lower anchoring element 132 can form and/or can include a feature that forms the guide wire coupler 133. In other implementations, the guide wire coupler 133 can be attached to any suitable portion of the frame 110, to the proximal anchoring element 134, to the anterior anchoring element 135, and/or to any other anchoring elements and/or features of the frame 110 (e.g., a distal or proximal upper anchoring element). In some embodiments, the guide wire coupler 133 is configured to allow a portion of the guide wire to extend through an aperture of the guide wire coupler 133, thereby allowing the valve 102 to be advanced over or along the guide wire. In some embodiments, the guide wire coupler 133 can selectively allow the guide wire to be advanced therethrough while blocking or preventing other elements and/or components such as a pusher or the like.

In some embodiments, the distal anchoring element 132 can include the guide wire coupler 133 and can be configured to transition between one or more states and/or configurations based at least in part on an interaction with the guide wire. For example, in some embodiments, the distal anchoring element 132 can have and/or can be placed in an extended configuration when the guide wire is coupled to and/or otherwise extends through the guide wire coupler 133, and can have and/or can be placed in an contracted or folded configuration when the guide wire is released from the guide wire coupler 133.

The anchoring elements 132, 134, and 135 of the valve 102 can be configured to engage a desired portion of the native tissue to mount the frame 110 to the annulus of the native valve in which the valve 102 is deployed. For example, in some implementations, the distal anchoring element 132 can extend from a lower distal side of the frame 110 and into a RVOT or a LVOT. In such implementations, the distal anchoring element 132 can be shaped and/or biased such that the distal anchoring element 132 exerts a force on the subannular tissue operable to at least partially secure the distal end portion of the valve 102 in the native annulus. In some implementations, the proximal anchoring element 134 can be, for example, a proximal lower anchoring element and can be configured to engage subannular tissue on a proximal side of the native annulus to aid in the securement of the valve 102 in the annulus. Likewise, the anterior anchoring element 134 can be an anterior lower anchoring element that can engage subannular tissue on an anterior side of the native annulus to aid in the securement of the valve 102 in the annulus.

In some implementations, the distal anchoring element 132, the proximal anchoring element 134, and/or the anterior anchoring element 135 can be configured to transition, move, and/or otherwise reconfigure between a first configuration in which the anchoring elements 132, 134, and/or 135, respectively, extend from the frame 110 a first amount or distance and a second configuration in which the anchoring elements 132, 134, and/or 135, respectively, extend from the frame 110 a second amount or distance. For example, in some embodiments, the anchoring elements 132, 134, and/or 135 can have a first configuration in which the anchoring elements 132, 134, and/or 135 are in a compressed, undeployed, folded, and/or restrained state (e.g., a position that is near, adjacent to, and/or in contact with the transannular section of the frame 110, and a second configuration in which the anchoring elements 132, 134, and/or 135 are in an expanded, extended, deployed, unfolded, and/or unrestrained state (e.g., extending away from the transannular section of the frame 110). As described in further detail herein, any of the anchoring elements 132, 134, and/or 135 can be actuated and/or otherwise transitioned between the first configuration and the second configuration during deployment to selectively engage native tissue, chordae, and/or any other anatomic structures to aid in the securement of the valve 102 in the native annulus.

The flow control component 150 can refer in a non-limiting sense to a device for controlling fluid flow therethrough. In some embodiments, the flow control component 150 can be a leaflet structure having 2-leaflets, 3-leaflets, 4-leaflets, or more, made of flexible biocompatible material such a treated or untreated pericardium. The leaflets can be sewn or joined to a support structure such as an inner frame, which in turn, can be sewn or joined to the outer frame 110. For example, in some embodiments, the flow control component 150 can be coupled to the frame 110 (e.g., to a drum, collar portion, transannular section, and/or the like) via tissue, a biocompatible mesh, one or more woven or knitted fabrics, one or more superelastic or shape-memory alloy structures, which is sewn, sutured, and/or otherwise secured to a portion of the frame. In some embodiments, the flow control component 150 (or portions and/or aspects thereof) can be similar to, for example, any of the flow control components described in the '231 PCT.

Figure 1D:
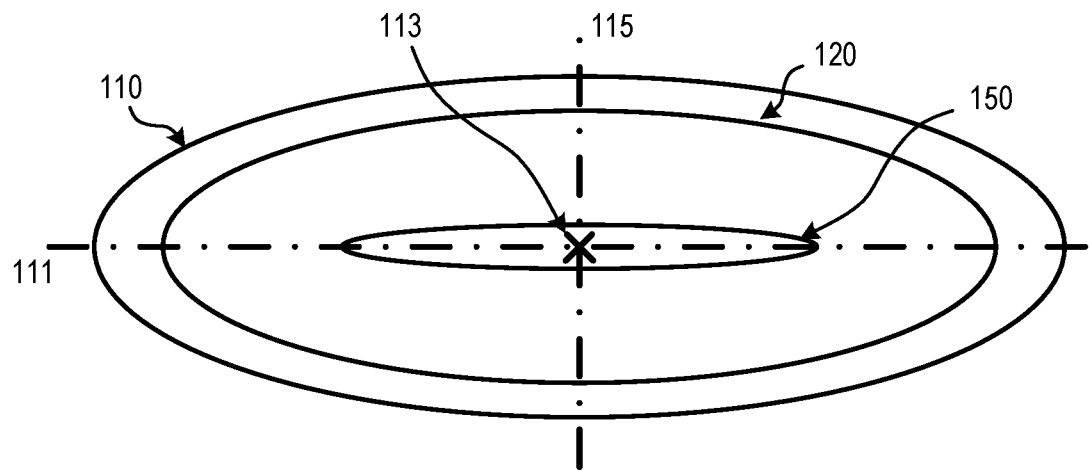

In some embodiments, the flow control component 150 and/or the inner frame thereof can have a substantially cylindrical or tubular shape when the valve 102 is in the expanded configuration (see e.g., FIG. 1C) and can be configured to elastically deform when the valve 102 is placed in the compressed configuration (see e.g., FIGS. 1B and 1D). The inner frame and/or portions or aspects thereof can be similar in at least form and/or function to the outer frame 110 and/or portions or aspects thereof. For example, the inner frame can be compressible for delivery and when released it is configured to return to its original (uncompressed) shape. The inner frame can be formed of a shape-memory element allowing the inner frame to be self-expanding. In some instances, suitable shape-memory materials can include metals and/or plastics that are durable and biocompatible such as, for example, Nitinol.

The inner frame of the flow control component 150 can be similar in at least form and/or function the inner frame of the flow control components 150 described in the '231 PCT. For example, the inner frame may be constructed as a wire, a braided wire, or a laser cut wire frame. In some embodiments, the inner frame can include and/or can form a set of compressible wire cells having an orientation and cell geometry substantially orthogonal to an axis of the flow control component 150 to minimize wire cell strain when the inner frame is in a compressed configuration. In some embodiments, the inner frame can have and/or can form any suitable number of elastically deformable diamond-shaped or eye-shaped wire cells, and/or the like. Although not shown in FIGS. 1A-1E, in some embodiments, the inner frame can include and/or can be formed with two halves that can be coupled together to allow the inner frame to elastically deform in response to lateral compression or folding along or in a direction of a lateral axis 115, as described in further detail herein.

The flow control component 150 can be mounted within the frame 110 and configured to permit blood flow in a first direction through an inflow end of the valve and block blood flow in a second direction, opposite the first direction, through an outflow end of the valve. For example, the flow control component 150 can be configured such that the valve 102 functions, for example, as a heart valve, such as a tricuspid valve, mitral valve, aortic valve, or pulmonary valve, that can open to blood flowing during diastole from atrium to ventricle, and that can close from systolic ventricular pressure applied to the outer surface. Repeated opening and closing in sequence can be described as "reciprocating."

As shown in FIGS. 1A-1D, the flow control component 150 is mounted within the central channel 114 of the frame 110. More specifically, the flow control component 150 can be mounted within the central channel 114 such that the axis of the flow control component 150 that extends in the direction of blood flow through the flow control component 150 is substantially parallel to the central axis 113 of the frame 110. In some embodiments, the flow control component 150 can be centered within the central channel 114 of the frame 110. In other embodiments, the flow control component 150 can be disposed in an off-center position within the central channel 114. In some embodiments, the central channel 114 can have a diameter and/or perimeter that is larger than a diameter and/or perimeter of the flow control component 150. Although not shown in FIGS. 1A-1E, in some embodiments, the valve 102 can include a spacer or the like that can be disposed within the central channel 114 adjacent to the flow control component 150. In other embodiments, a spacer can be a cover or the like coupled to a portion of the frame 110 and configured to cover a portion of the central channel 114. In some instances, the spacer can be used to facilitate the coupling of the flow control component 150 to the frame 110.

As described above, the valve 102 is compressible and expandable between the expanded configuration and the compressed configuration. The valve 102 can have a first height or size along the central axis 113 when in the expanded configuration and can have a second height or size, less than the first height or size, along the central axis 113 when in the compressed configuration. The valve 102 can also be compressed in additional directions. For example, the valve 102 can be compressed along the lateral axis 115 that is perpendicular to both the longitudinal axis 111 and the central axis 113 (see e.g., FIG. 1D).

The valve 102 is compressed during delivery of the valve 102 and is configured to expand once released from the delivery catheter. More specifically, the valve 102 is configured for transcatheter orthogonal delivery to the desired location in the body (e.g., the annulus of a native valve), in which the valve 102 is compressed in an orthogonal or lateral direction relative to the dimensions of the valve 102 in the expanded configuration (e.g., along the central axis 113 and/or the lateral axis 115). During delivery, the longitudinal axis 111 of the valve 102 is substantially parallel to a longitudinal axis of the delivery catheter. In orthogonal delivery, the longitudinal axis 111 is oriented at an intersecting angle between 45 and 135 degrees relative to the central axis 113 (e.g., perpendicular or at about 90 degrees) and is in a substantially parallel orientation relative to a lengthwise cylindrical axis of the delivery catheter.

The valve 102 is in the expanded configuration prior to being loaded into the delivery catheter and/or after being released from the delivery catheter and deployed or implanted (or ready to be deployed or implanted) at the desired location in the body. The shape of the expanded valve 102 can be that of a large diameter shortened cylinder with an extended collar (e.g., the collar). When in the expanded configuration shown in FIGS. 1A, 1C, and 1E, the valve 102 has an extent in any direction orthogonal or lateral to the longitudinal axis 111 (e.g., along the central axis 113 and/or the lateral axis 115) that is larger than a diameter of the lumen of the delivery catheter used to deliver the valve 102. For example, in some embodiments, the valve 102 can have an expanded height (e.g., along the central axis 113) of 5-60 mm. In certain embodiments, the valve 102 can have an expanded height including, for example, 5 mm, 10 mm, 15 mm, 20 mm, 25 mm, 30 mm, 35 mm, 40 mm, 45 mm, 50 mm, 55 mm, and 60 mm, and/or any size or fraction of a size therebetween. In some embodiments, the valve 102 can have an expanded diameter length (e.g., along the longitudinal axis 111) and width (e.g., along the lateral axis 115) of about 20-80 mm, or about 40-80 mm. In certain embodiments, the valve 102 can have an expanded length and/or width including, for example, 20 mm, 25 mm, 30 mm, 35 mm, 40 mm, 45 mm, 50 mm, 55 mm, 60 mm, 65 mm, 70 mm, 75 mm, and 80 mm, and/or any size or fraction of a size therebetween.

When in the compressed configuration shown in FIGS. 1B and 1D, the valve 102 has an extent in any direction orthogonal or lateral to the longitudinal axis 111 (e.g., along the central axis 113 and/or the lateral axis 115) that is smaller than the diameter of the lumen of the delivery catheter, allowing the valve 102 to be delivered therethrough. For example, in some embodiments, the valve 102 can have a compressed height (e.g., along the central axis 113) and a compressed width (e.g., along the lateral axis 115) of about 6-15 mm, about 8-12 mm, or about 9-10 mm. In certain embodiments, the valve 102 can have a compressed height and/or width including, for example, 6 mm, 7 mm, 8 mm, 9 mm, 10 mm, 11 mm, 12 mm, 13 mm, 14 mm, and 15 mm, and/or any size or faction of a size therebetween. The valve 102 can be compressed by compressing, rolling, folding, and/or any other suitable manner, or combinations thereof, as described in detail in the '957 PCT, the '010 PCT, and/or the '231 PCT. It is contemplated in some embodiments that the length of the valve 102 (e.g., along the longitudinal axis 111) is not compressed for delivery. Rather, in some embodiments, the length of the 102 can be increased in response to compression of the valve 102 along the central axis 113 and/or the lateral axis 115.

Although not shown in FIGS. 1A-1E, in some implementations, a delivery system can include one or more features or components configured to deliver the valve 102 to a desired location in the body (e.g., the annulus of a native valve). For example, a delivery system can include the delivery catheter, a positioning tool, and the guide wire. The delivery system can be configured to orthogonally deliver the compressed valve 102 and/or portions of the valve 102 (e.g., the compressed frame 110 or the compressed flow control component 150) to a desired location in the body such as, for example, the annulus of a native tricuspid valve and/or the annulus of a native mitral valve of the human heart. For example, the delivery catheter can be 12-34 Fr, with any suitable corresponding internal lumen diameter and/or an internal lumen diameter sufficient to receive the prosthetic valve 102 in the compressed configuration. In some implementations, the delivery system and/or aspects or portions thereof can be substantially similar in at least form, function, and/or operation as those described in detail in the '957 PCT, the '010 PCT, and/or the '231 PCT, and thus, is not described in further detail herein.

Figure 1E:
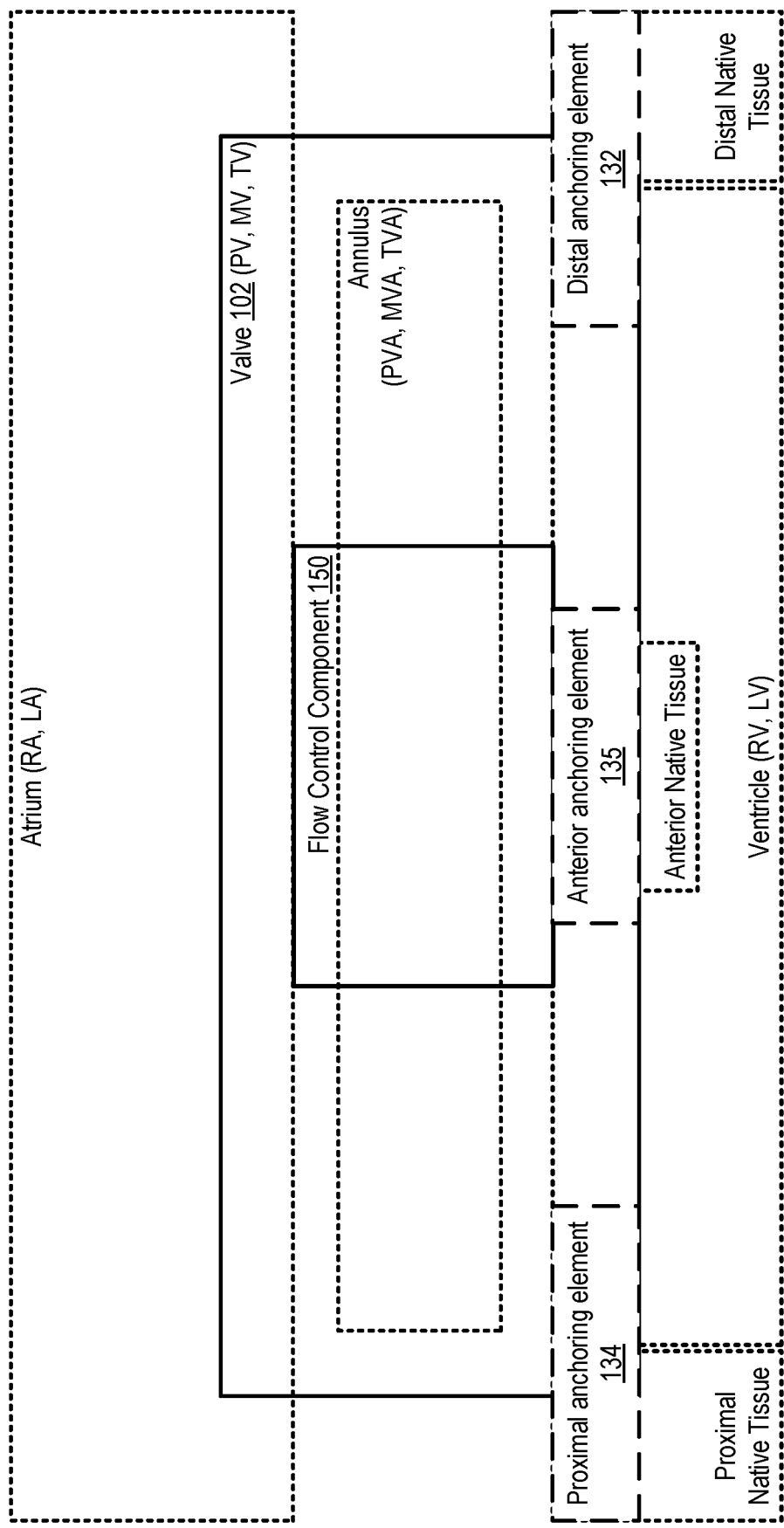
FIG. 1E is a schematic illustration of the prosthetic valve of FIGS. 1A-1D deployed within an annulus of a native heart valve.

As shown in FIG. 1E, the valve 102 can be delivered, for example, to an atrium of the human heart and disposed within an annulus of a native valve such as, for example, the pulmonary valve (PV), the mitral valve (MV), the aortic valve (AV), and/or the tricuspid valve (TV). As described above, the valve 102 can be in the compressed configuration and delivered to the annulus via the delivery system and can be released from the delivery system and allowed to expand to the expanded configuration. For example, the valve 102 can be delivered to the atrium of the human heart and released from the delivery catheter (not shown) via any of the delivery systems, devices, and/or methods described in detail in the '957 PCT, the '010 PCT, and/or the '231 PCT.

In some implementations, the delivery of the valve 102 can include advancing a guide wire into the atrium of the human heart, through the native valve, and to a desired position within the ventricle (e.g., the RVOT or the LVOT). After positioning the guide wire, the delivery catheter can be advanced along and/or over the guide wire and into the atrium (e.g., via the IVC, the SVC, and/or a trans-septal access). In some embodiments, the guide wire coupler 136 can be coupled to a proximal end portion of the guide wire and the valve 102 can be placed in the compressed configuration, allowing the valve 102 to be advanced along the guide wire and through a lumen of the delivery catheter, and into the atrium.

The deployment of the valve 102 can include placing the distal anchoring element 132 (e.g., the distal lower anchoring element 132) in the ventricle (RV, LV) below the annulus while the remaining portions of the valve 102 are in the atrium (RA, LA). In some instances, the distal anchoring element 132 can be advanced over and/or along the guide wire to a desired position within the ventricle such as, for example, an outflow tract of the ventricle. For example, in some implementations, the valve 102 can be delivered to the annulus of the native tricuspid valve (TV) and at least a portion of the distal anchoring element 132 can be positioned in the RVOT. In other implementations, the valve 102 can be delivered to the annulus of the native mitral valve (MV) and at least a portion of the distal anchoring element 132 can be positioned in the LVOT.

In some implementations, the distal anchoring element 132 can be placed and/or transitioned from the first or folded configuration to the second or extended configuration during delivery and/or deployment prior to the valve 102 being completely seated in the native annulus. In some embodiments, for example, the distal anchoring element 132 can be in the second or extended configuration by virtue of the guide wire coupler 136 being coupled to and/or otherwise engaging the guide wire. The distal anchoring element 132, therefore, can be in the second or extended configuration when inserted through the native annulus and into the ventricle. In some instances, the distal anchoring element 132 can extend around and/or through one or more portions of native tissue, chordae, and/or the like, which can allow the distal anchoring element 132 to capture and/or engage the native tissue, chordae, etc. when the distal anchoring element 132 is transitioned and/or returned to the first configuration, as described in further detail here.

In some implementations, the prosthetic valve 102 can be temporarily maintained in a partially deployed state. For example, the valve 102 can be partially inserted into the annulus and held at an angle relative to the annulus to allow blood to flow from the atrium to the ventricle partially through the native valve annulus around the valve 102, and partially through the valve 102, which can allow for assessment of the valve function.

The valve 102 can be placed or seated in the annulus (PVA, MVA, AVA, and/or TVA) of the native valve (PV, MV, AV, and/or TV) such that the transannular section of the valve frame 110 extends through the annulus and into the ventricle while the collar (e.g., atrial collar) remains in the atrium (for a tricuspid or mitral valve, or aorta for an aortic valve, or pulmonary artery for a pulmonary valve) in a supra-annular position. For example, in some embodiments, a positioning tool and/or pusher (not shown) can be used to push at least the proximal end portion of the valve 102 into the annulus. In some implementations, the proximal anchoring element 134 can be maintained in its first configuration as the valve 102 is seated in the annulus. For example, as described above, the proximal anchoring element 134 can be in contact with, adjacent to, and/or near the transannular section of the frame 110 while in the first configuration, which in turn, can limit an overall circumference of a lower portion of the frame 110, thereby allowing the transannular section of the frame 110 to be inserted through the annulus.

Once seated, the proximal anchoring element 134 can be transitioned from its first configuration to its second configuration, as described in detail in the '010 PCT. Accordingly, once the valve 102 is seated in the annulus, the proximal anchoring element 134 can be placed in its second configuration in which the proximal anchoring element 134 contacts, engages, and/or is otherwise disposed adjacent to subannular tissue. In some implementations, the proximal anchoring element 134 can be configured to engage and/or capture native tissue, chordae, and/or the like when the proximal anchoring element 134 is disposed in the ventricle. For example, in some implementations, after seating the valve 102 in the annulus, the proximal anchoring element 134 can be transitioned from the first (compressed) configuration to the second (extended) configuration such that the proximal anchoring element 134 extends around and/or through one or more portions of native tissue, chordae, etc. The proximal anchoring element 134 can then be returned to the first configuration to capture and/or secure the one or more portions of native tissue, chordae, etc. between the proximal anchoring element 134 and, for example, the transannular section of the outer frame 110. In other implementations, the proximal anchoring element 134 can be maintained in the second (extended) configuration after the valve 102 is seated in the native annulus. In such implementations, the proximal anchoring element 134, for example, can contact and/or engage subannular tissue on a proximal side of the annulus such that the proximal anchoring element and a proximal portion of the atrial collar exert a compressive force on a proximal portion of the annular tissue.

In embodiments in which the valve 102 includes the optional anterior anchoring element 135, the anterior anchoring element 135 can be in the first (compressed or retracted) configuration prior to the valve 102 being completed seated in the native annulus, as described above with reference to the proximal anchoring element 134. As such, a perimeter of transannular section can be sufficiently small to allow the transannular section to the inserted through the annulus of the native valve. Once seated, the anterior anchoring element 135 can be transitioned from its first configuration to its second (extended) configuration. For example, in some embodiments, the valve 102 and/or the frame 110 can include a sleeve, conduit, tube, channel, etc. in which a first portion of the anterior anchoring element 135 is disposed when in the first configuration and when transitioned to the second configuration, a second portion of the anterior anchoring element 135 less than the first portion is disposed within the sleeve, conduit, tube, channel, etc. Said another way, the anterior anchoring element 135 can extend from the sleeve, conduit, tube, channel, etc. when in the second configuration.

In some embodiments, the anterior anchoring element 135 can form a hook or clip when in the second configuration. For example, the anterior anchoring element 135 can be formed from a shape-memory alloy or the like that is biased or heat set into the hook or clip shape or configuration. In some implementations, such an arrangement can allow the anterior anchoring element 135 to extend around and/or through a portion of native tissue, chordae, and/or the like. The anterior anchoring element 135 can then be actuated, transitioned, moved, etc. from the second (extended) configuration back toward the first (compressed or folded) configuration. For example, the anterior anchoring element 135 can be retracted or at least partially retracted into the sleeve, conduit, tube, channel, etc. of the valve 102. With the anterior anchoring element 135 positioned around, positioned through, and/or otherwise engaged with the native tissue, chordae, etc., the transitioning of the anterior anchoring element 135 from the second configuration to the first configuration can result in the anterior anchoring element 135 capturing and/or securing at least a portion of the native tissue, chordae, etc. between the anterior anchoring element 135 and, for example, the transannular section of the frame 110.

In this manner, the distal anchoring element 132 can be configured to engage native tissue on a distal side of the annulus, the proximal anchoring element 134 can be configured to engage native tissue on a proximal side of the annulus, and the anterior anchoring element 135 can be configured to engage native tissue on the anterior side of the annulus, thereby securely seating the valve 102 in the native annulus, as shown in FIG. 1E.

While not shown in FIGS. 1A-1E, in some implementations, the valve 102 and/or the delivery system can include one or more tissue anchors that can be used to anchor one or more portions of the valve 102 to the annular tissue, as described in detail in the '957 PCT. In some embodiments, the tissue anchors can be configured to puncture, pierce, and/or otherwise secure the anchoring elements 132, 134, and/or 135, and/or the atrial collar to the annular tissue. In other embodiments, the tissue anchors can be, for example, a traumatic anchors configured to secure the anchoring elements 132, 134, and/or 135, and/or the atrial collar to the annular tissue without puncturing, piercing, and/or otherwise causing trauma to the native tissue.

Provided below is a discussion of certain aspects or embodiments of side deliverable transcatheter prosthetic valves (e.g., prosthetic heart valves). The transcatheter prosthetic valves (or aspects or portions thereof) described below with respect to specific embodiments can be substantially similar in at least form and/or function to the valve 102 and/or corresponding aspects or portions of the valve 102 described above with reference to FIGS. 1A-1E. Similarly, the valves described below (or aspects or portions thereof) can be similar in at least form and/or function to the valves described in detail in the '957 PCT, the '010 PCT, and/or the '231 PCT. Thus, certain aspects and/or portions of the specific embodiments may not be described in further detail herein.

Any of the prosthetic valves described herein can be used to replace a native valve of a human heart including, for example, a mitral valve, a tricuspid valve, an aortic valve, and/or a pulmonary valve. While examples of specific valves are described herein, it should be understood that they have been presented by way of example only and not limitation. Thus, while some prosthetic valves are described herein as being configured to replace a native mitral valve or a native tricuspid valve, it should be understood that such a prosthetic valve can be used to replace any native valve unless expressly stated otherwise or unless one skilled in the art would clearly recognize that one or more components and/or features would otherwise make the prosthetic valve incompatible for such use.

Figure 2A:
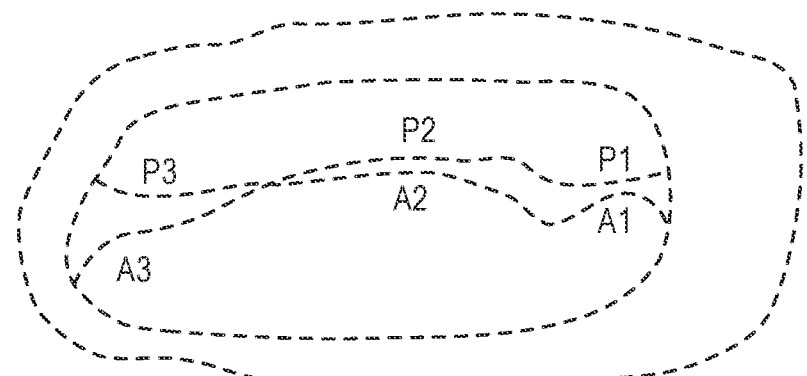
FIG. 2A is an illustration of a top view of a native mitral valve showing approximate locations of leaflet areas A1-A2-A3 and P1-P2-P3.

In some embodiments, a side deliverable transcatheter prosthetic heart valve can be configured to replace, for example, a native mitral valve of the human heart. FIG. 2A is an illustration of a top view of a native mitral valve showing approximate locations of native leaflet anterior (A) areas A1-A2-A3 and native leaflet posterior (P) areas P1-P2-P3.

Figure 2B:
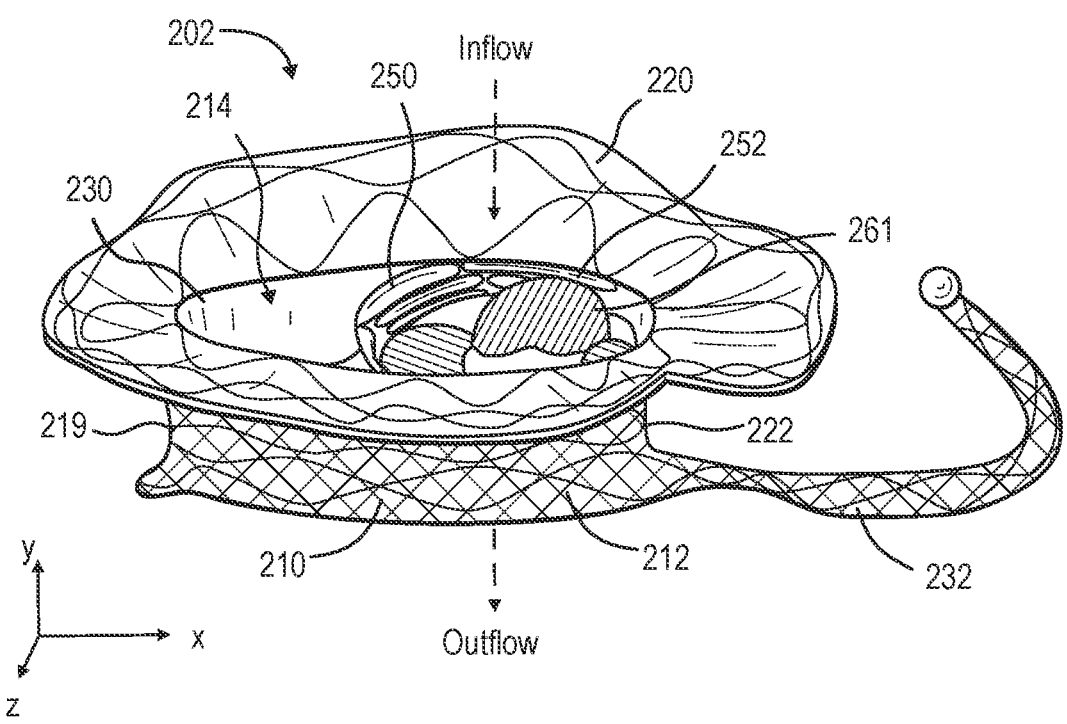
FIGS. 2B and 2C are illustrations of a side perspective view and an exploded view, respectively, of a side deliverable transcatheter prosthetic heart valve with an extendable distal anchoring element, according to an embodiment.
Figure 2C:
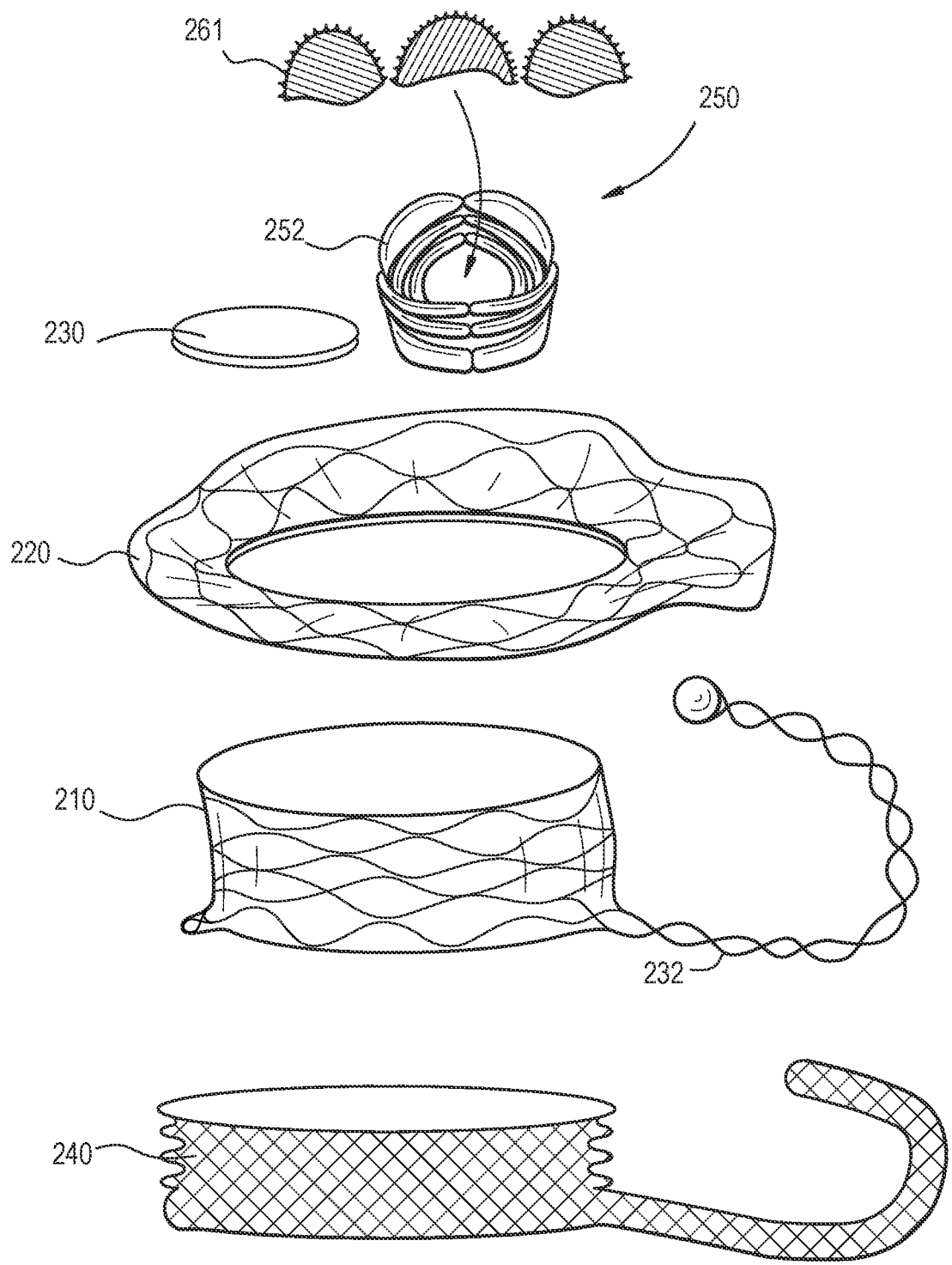

FIGS. 2B and 2C are illustrations of a side perspective view and an exploded view, respectively, of a side-deliverable (orthogonally deliverable) transcatheter prosthetic heart valve 202 (also referred to herein as "prosthetic valve" or "valve"), according to an embodiment. In some implementations, the valve 202 can be deployed in, for example, an annulus of a native mitral valve. The valve 202 is configured to permit blood flow in a first direction through an inflow end of the valve 202 and to block blood flow in a second direction, opposite the first direction, through an outflow end of the valve 202. For example, the prosthetic valve 202 can be a side deliverable transcatheter prosthetic heart valve configured to be deployed within the annulus of a native tricuspid valve or native mitral valve of a human heart to supplement and/or replace the functioning of the native valve.

The valve 202 is compressible and expandable in at least one direction relative to an x-axis of the valve 202 (also referred to herein as "horizontal axis," "longitudinal axis," "long axis," and/or "lengthwise axis"). The valve 202 is compressible and expandable between an expanded configuration for implanting at a desired location in a body (e.g., a human heart) and a compressed configuration for introduction into the body using a delivery catheter (not shown in FIGS. 2B and 2C). In some embodiments, the horizontal x-axis of the valve 202 is orthogonal to (90 degrees), or substantially orthogonal to (75-105 degrees), or substantially oblique to (45-135 degrees) to a central (vertical) y-axis when in the expanded and/or compressed configuration. Moreover, the horizontal x-axis of the valve 202 in the compressed configuration is substantially parallel to a lengthwise cylindrical axis of the delivery catheter in which the valve 202 is disposed.

In some embodiments, the valve 202 has an expanded or deployed height of about 5-60 mm, about 5-30 mm, about 5-20 mm, about 8-12 mm, or about 8-10 mm, and an expanded or deployed diameter (e.g., length and/or width) of about 25-80 mm, or about 40-80 mm. In certain embodiments, the expanded or deployed diameter (e.g., length and/or width) can be about 25 mm, 30 mm, 35 mm, 40 mm, 45 mm, 50 mm, 55 mm, 60 mm, 65 mm, 70 mm, 75 mm, and 80 mm (or any value or fraction of a value therebetween). In some embodiments, the valve 202 has a compressed height (y-axis) and width (z-axis) of about 6-15 mm, about 8-12 mm, or about 9-10 mm. It is contemplated in preferred embodiments that the length of the valve 202 (e.g., along the x-axis) is not compressed or otherwise reduced since it can extend along the length of the central cylindrical axis of the delivery catheter.

In certain preferred embodiments, the valve 202 is centric, or radially symmetrical. In other preferred embodiments, the valve 202 is eccentric, or radially asymmetrical (e.g., along or relative to the y-axis). In some eccentric embodiments, the frame 210 may have a D-shape in cross-section, with a flat portion or surface configured to substantially match an annulus of a native mitral valve at or near the anterior leaflet.

The valve 202 includes an annular outer support frame 210 and a collapsible flow control component 250 mounted within the annular outer support frame 210. The annular outer support frame 210 (also referred to herein as "outer frame") is made from a shape-memory material such as Nickel-Titanium alloy, for example Nitinol, and is therefore a self-expanding structure from a compressed configuration to an expanded configuration. The outer frame 210 has a transannular and/or body section 212 that circumscribes, forms, and/or defines a central (interior) channel 214 about and/or along the vertical or central axis (y-axis), and has an atrial collar 220 attached circumferentially at a top edge of the transannular and/or body section 212 of the outer frame 210. The atrial collar 220 is shaped to conform to the native deployment location. In a tricuspid replacement, for example, the atrial collar 220 can have a tall back wall portion to conform to the septal area of the native valve, and can have a distal upper and proximal upper collar portion. The distal upper collar portion can be larger than the proximal upper collar portion to account for the larger flat space above (atrial) the ventricular outflow tract (VOT) subannular area. In a mitral replacement, for example, the annular collar 220 and/or outer frame 210 may be D-shaped or shaped like a hyperbolic paraboloid to mimic the native structure.

The outer frame 210 further has a proximal side 219 and a distal side 222. A distal anchoring element 232 (e.g., a superelastic wire loop distal tab) is coupled to and/or extends from the distal side 222. In some embodiments, the distal anchoring element 232 is an integrated tab that is unitarily constructed with the body section 212 of the outer frame 210. The distal anchoring element 232 may vary in size and shape. For example, in some embodiments, the distal anchoring element 232 (e.g., a right VOT tab) may be sufficiently long to reach into the entry of the pulmonary artery (in the case of a tricuspid replacement).

In other embodiments, the shape of the distal anchoring element 232 is configured to conform to the A1 commissural area of the mitral valve. For example, in some embodiments, the distal anchoring element 232 can be about 10-40 mm in length. Moreover, the distal anchoring element 232 can be a reconfigurable distal anchoring element 232 configured to transition between, for example, a compressed, contracted, and/or folded configuration (e.g., a first configuration) and an extended or unfolded configuration (e.g., a second configuration).

For example, in some implementations, the distal anchoring element 232 is configured to track on a guide wire (not shown) inserted near the A1 leaflet/commissure of the mitral valve. In some implementations, the guide wire is pre-positioned around the native mitral leaflets and/or chordae, especially the mitral A2 leaflet, to facilitate the over-wire placement of the distal anchoring element 232 around the "back side" of the A2 leaflet to clamp the native A2 leaflet against the frame 210. In some implementations, the distal anchoring element 232 can be configured in the extended configuration to reach around the P2 and/or P3 leaflets of a native mitral valve and/or chordae associated therewith and can be transitioned to the compressed configuration to capture and/or pin native tissue, chordae, etc., between the distal anchoring element 232 and the transannular section 212 of the outer frame 210.

As shown in FIG. 2C, at least the outer support frame 210 of the valve 202 is covered, wrapped, and/or surrounded by a biocompatible cover 240. The biocompatible cover 240 can be a mesh material, a pericardial tissue, a woven synthetic polyester material, and/or any other suitable biocompatible material such as those described above.

The collapsible (inner) flow control component 250 is mounted within the outer frame 210. The flow control component 250 has a foldable and compressible inner wire frame 252 (also referred to as "inner leaflet frame" or "inner frame") with two or more fold areas, hinge areas, coupling areas, elastically deformable regions, etc. A set of 2-4 flexible leaflets 261 are mounted in or on the inner frame 252. In some embodiments, the flow control component 250 has three leaflet 261 cusps or pockets mounted within the inner frame 252.

The inner flow control component 250, like the outer frame 210, is foldable and compressible. For example, the inner frame 252 is foldable along or in the direction of a z-axis (e.g., foldable at the fold areas or the like) from a cylindrical configuration to a flattened cylinder configuration (or a two-layer band), where the fold areas are located on a distal side and on a proximal side of the inner frame 252. The flow control component 250, like the outer frame 210, is also vertically (y-axis) compressible to a shortened or compressed configuration. By folding (compressing) in the direction of the z-axis and vertically compressing in the y-axis, the valve 202 is permitted to maintain a relatively large dimension along the horizontal (x-axis). In some implementations, the outer frame 210 and the flow control component 250 are reduced along z-axis until the side walls are in contact or nearly so. This also allows the outer frame 210 and the flow control component 250 to maintain the radius along the horizontal axis (x-axis), to minimize the number of wire cells, which make up the outer and the inner frames, that can be damaged by forces applied during folding and/or compression necessary for loading into the delivery catheter.

The flow control component 250 has a diameter and/or perimeter that is smaller than a diameter and/or perimeter of the central channel 214 of the outer frame 210. The flow control component 250 is mounted to or within the outer frame 210 such that a central or vertical axis (y-axis) of the inner frame 252 is parallel to the central or vertical axis (y-axis) of the outer frame 210. In some embodiments, the y-axis defined by the inner frame 252 is parallel to but offset from the y-axis defined by the outer frame 210 (FIG. 2B). In some implementations, a spacer element 230 is disposed within the central channel 214 and can facilitate the mounting of a portion of the flow control component 250 (e.g., an otherwise unsupported portion) to the outer support frame 210. In some embodiments, the spacer element 230 can be a cylindrical tube or frame configured to support a portion of the flow control component 250. In other embodiments, the spacer element 230 can be any suitable shape, size, and/or configuration. The spacer element 230 can be a covered or uncovered wire loop or the like that can be coupled to and/or integrated with a drum or collar of the frame 210.

In some embodiments, the spacer element 230 can also provide for controlled regurgitation of the valve 202. For example, in some embodiments, the spacer 230 can be uncovered or covered with a fluid permeable mesh, cloth, and/or biocompatible material. In some embodiments, the uncovered spacer 230 can be later plugged with an inserted stent, cover, plug, and/or the like (e.g., once regurgitation is no longer desirable for the proper functioning of the heart of the patient). In some embodiments, the spacer element 230 can be used for pace-maker wiring, or for punching a hole for planned partial regurgitation. In an embodiment where planned partial regurgitation is warranted, the used of an uncovered spacer 230 in place of the spacer element 230 provides for controlled regurgitation of the valve. The uncovered spacer 230 can be later plugged with a later-inserted stent or cover or plug once regurgitation is no longer needed by the patient.

In some embodiments, the spacer element 230 can be similar to or substantially the same as the inner frame 252 of the flow control component 250 without having leaflets mounted therein. In other embodiments, the spacer element 230 can include leaflets mounted therein (e.g., similar in form and/or configuration as the leaflets 261 or different in form and/or configuration from the leaflets 261). Similarly stated, the valve 202 can include two flow control components 250 with each flow control component 250 acting as a spacer with respect to the other flow control component 250.

In certain embodiments, the inner frame 252 can have a diameter of about 25-30 mm, the outer frame 210 can have a diameter of about 50-80 mm, and the atrial collar 220 can extend beyond the top edge of the outer frame by about 20-30 mm to provide a seal on the atrial floor against perivalvular leaks (PVLs). The flow control component 250 and the outer frame 210 can be foldable (e.g., in the direction of the z-axis) and/or compressible (e.g., in the direction of the y-axis) to reduce a side of the entire valve 202 to fit within the inner diameter of a 24-36 Fr (8-12 mm inner diameter) delivery catheter (not shown in this FIGS. 2B and 2C).

Figure 3A:
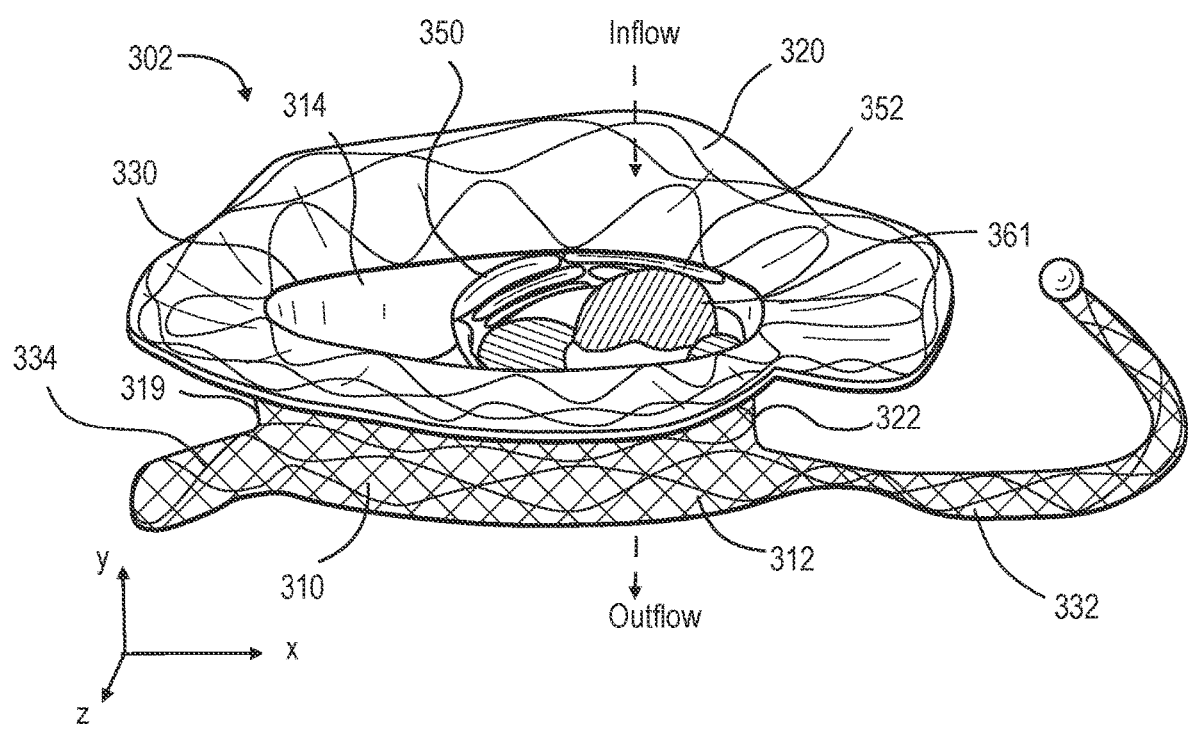
FIGS. 3A and 3B are illustrations of a side perspective view and an exploded view, respectively, of a side deliverable transcatheter prosthetic heart valve with an extendable distal anchoring element and an anterior anchoring element, according to an embodiment.
Figure 3B:
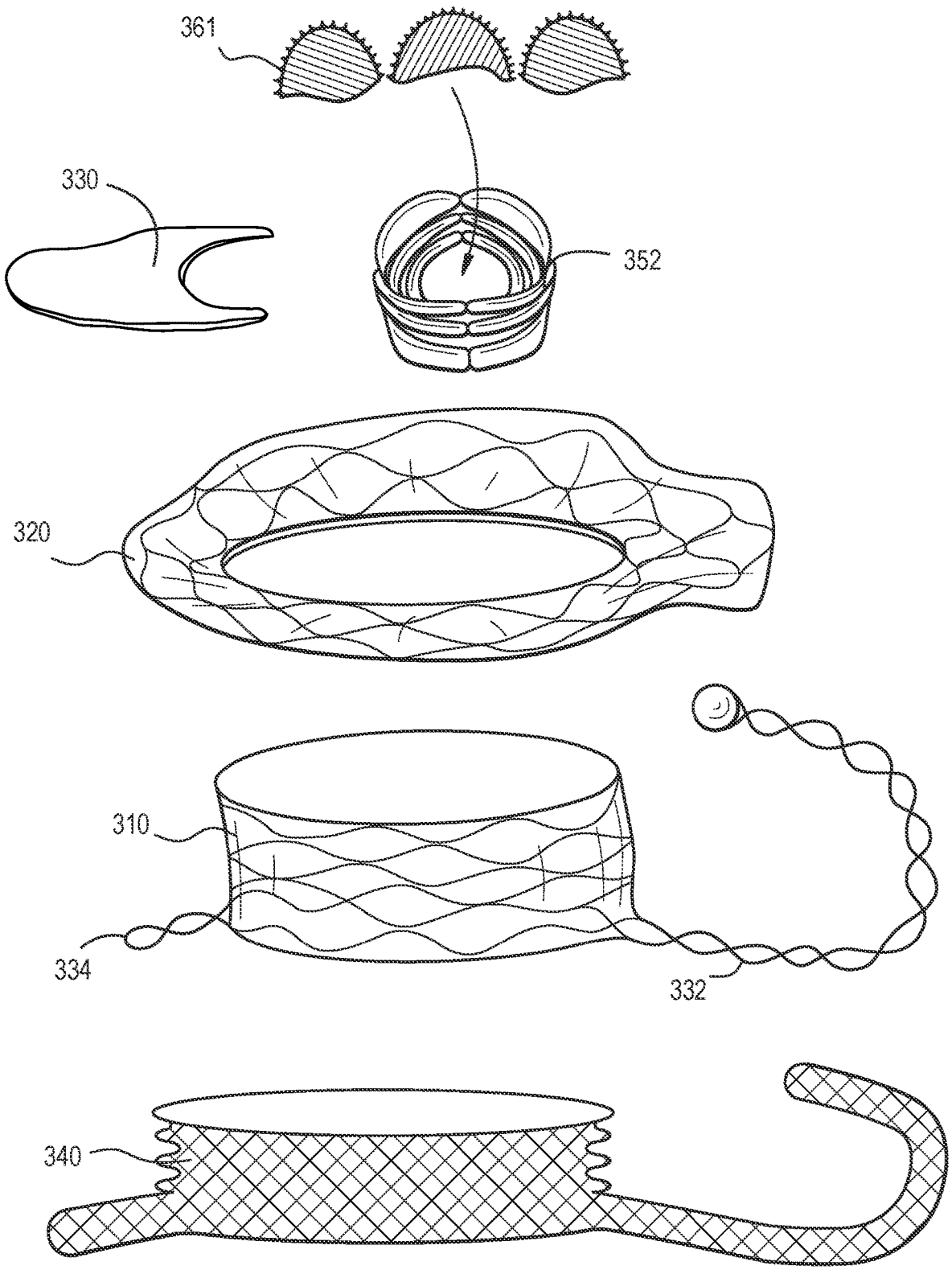

FIGS. 3A and 3B are illustrations of a side perspective view and an exploded view, respectively, of a side-deliverable (orthogonally deliverable) transcatheter prosthetic heart valve 302 (also referred to herein as "prosthetic valve" or "valve"), according to an embodiment. In some implementations, the valve 302 can be deployed in, for example, an annulus of a native mitral valve. The valve 302 is configured to permit blood flow in a first direction through an inflow end of the valve 302 and to block blood flow in a second direction, opposite the first direction, through an outflow end of the valve 302. The valve 302 is compressible and expandable between an expanded configuration for implanting in an annulus of a target valve (e.g., in a human heart) and a compressed configuration for introduction into the body using a delivery catheter (not shown in FIGS. 3A and 3B).

The valve 302 includes an annular outer support frame 310 and a collapsible flow control component 350 mounted within the annular outer support frame 310. The annular outer support frame 310 (also referred to herein as "outer frame") is made from a shape-memory material such as Nickel-Titanium alloy, for example Nitinol, and is therefore a self-expanding structure from a compressed configuration to an expanded configuration. At least a portion of the outer frame 310 is covered, wrapped, and/or surrounded by a biocompatible cover 340 such as those described above.

The outer frame 310 has a transannular and/or body section 312 that circumscribes, forms, and/or defines a central (interior) channel 314 about and/or along the vertical or central axis (y-axis), and has an atrial collar 320 attached circumferentially at a top edge of the transannular and/or body section 312 of the outer frame 310. The outer frame 310 has a proximal side 319 and a distal side 322.

The collapsible (inner) flow control component 350 is mounted within the outer frame 310 adjacent to a covered or uncovered spacer 330. The flow control component 350 has an inner frame 352 with two or more fold areas, hinge areas, coupling areas, elastically deformable regions, etc. A set of 2-4 flexible leaflets 361 are mounted in or on the inner frame 352. The inner flow control component 350, like the outer frame 310, is foldable and compressible. The flow control component 350 is mounted to or within the outer frame 310 such that a central or vertical axis (y-axis) of the inner frame 352 is coaxial with and/or at least parallel to (e.g., parallel to but offset from) the central axis (y-axis) of the outer frame 310.

FIGS. 3A and 3B further show the valve 302 includes a distal anchoring element 332 and a proximal anchoring element 334. The distal anchoring element 332 (e.g., a superelastic wire loop distal tab) is coupled to and/or extends from the distal side 322 of the outer frame 310 and the proximal anchoring element 334 (e.g., a superelastic wire loop proximal tab) is coupled to and/or extends from the proximal side 319 of the outer support frame 310. In some embodiments, the distal anchoring element 332 and the proximal anchoring element 334 can be integrated tabs that are unitarily constructed with the body section 312 of the outer frame 310. The anchoring elements 332 and 334 may vary in size and shape. For example, in some embodiments, the shape of the distal anchoring element 332 is configured to conform to the A1 commissural area of the mitral valve. In some embodiments, the shape of the proximal anchoring element 334 is configured to conform to the A3 commissural area of the mitral valve.

In some embodiments, at least the distal anchoring element 332 can be transitioned between, for example, a compressed, contracted, and/or folded configuration (e.g., a first configuration) and an extended or unfolded configuration (e.g., a second configuration). In the extended configuration, the distal anchoring element 332 can reach around the P2 and/or P3 leaflets of a native mitral valve and/or chordae associated therewith and when transitioned to the compressed configuration, the distal anchoring element 332 can capture and/or pin native tissue, chordae, etc., between the distal anchoring element 332 and the transannular section 312 of the outer frame 310.

Figure 4A:
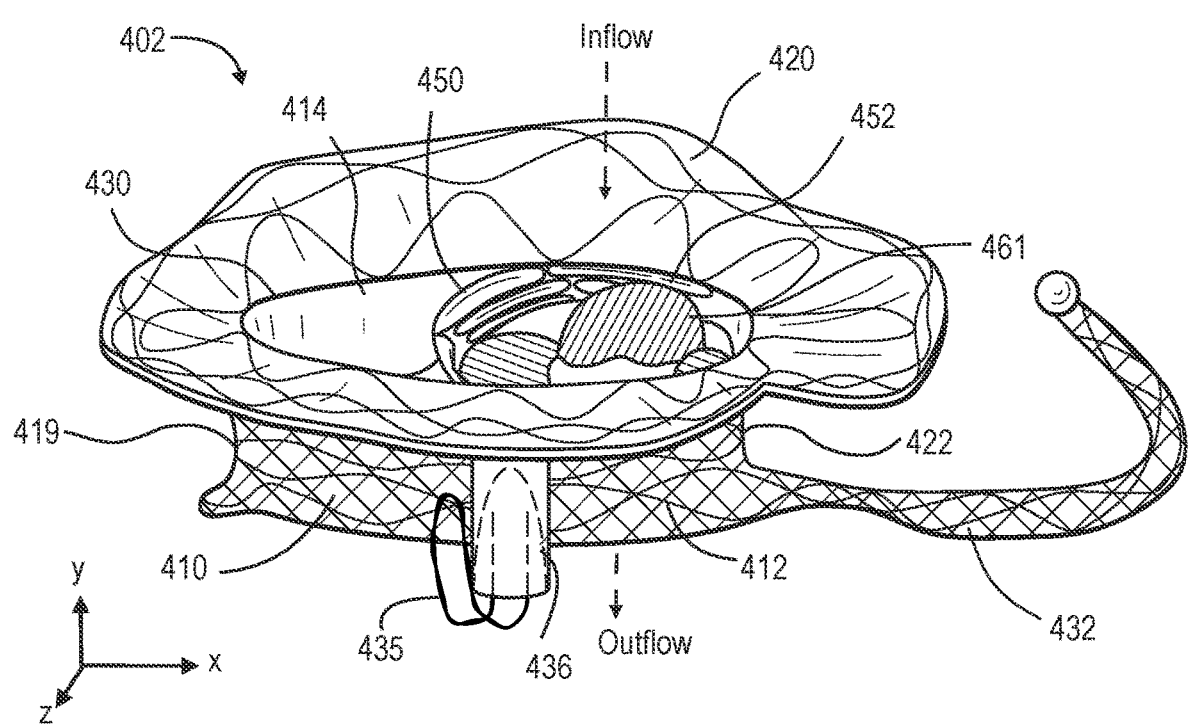
FIGS. 4A and 4B are illustrations of a side perspective view and an exploded view, respectively, of a side deliverable transcatheter prosthetic heart valve with an extendable distal anchoring element and a proximal anchoring element, according to an embodiment.
Figure 4B:
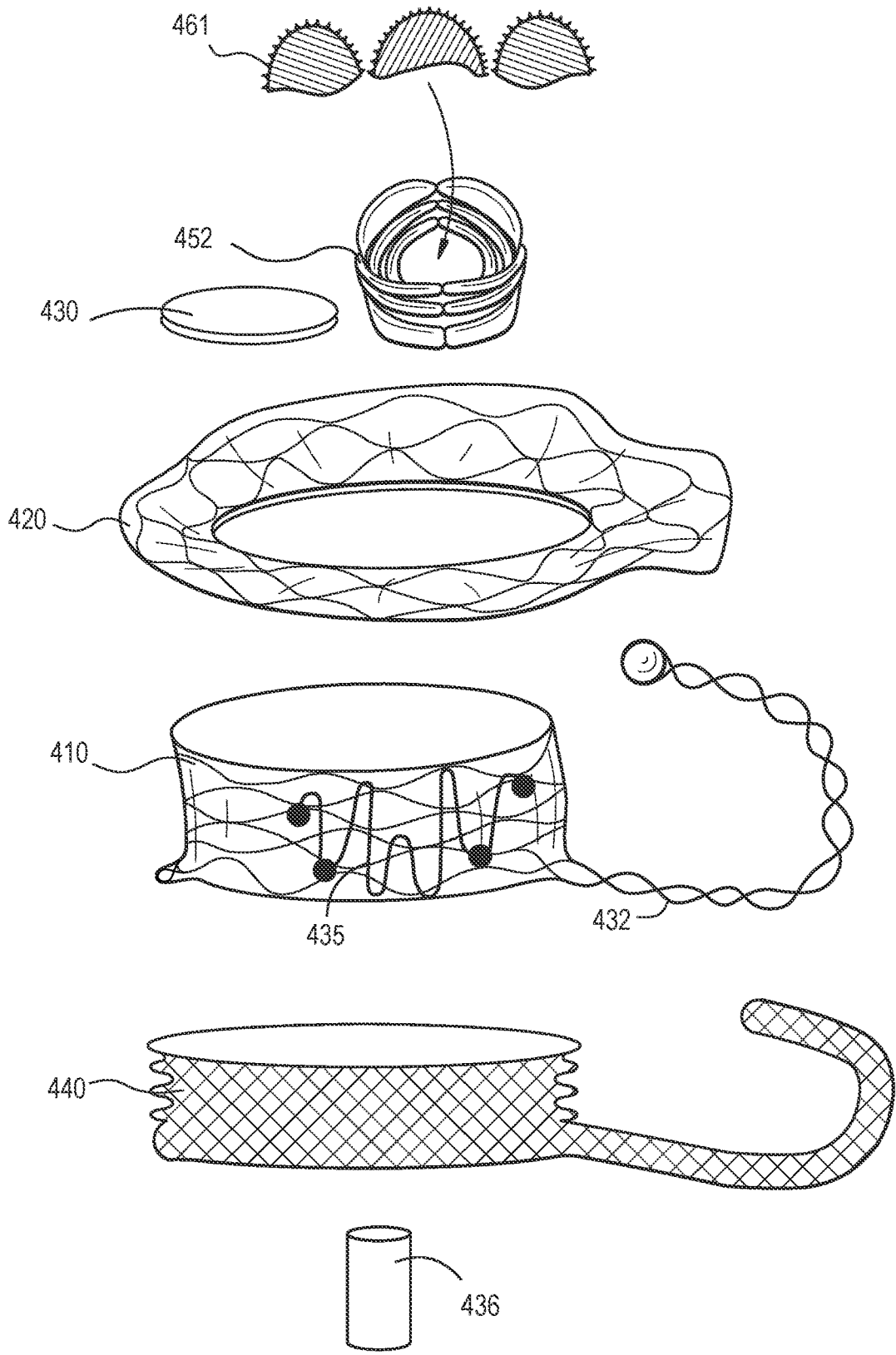

FIGS. 4A and 4B are illustrations of a side perspective view and an exploded view, respectively, of a side-deliverable (orthogonally deliverable) transcatheter prosthetic heart valve 402 (also referred to herein as "prosthetic valve" or "valve"), according to an embodiment. In some implementations, the valve 402 can be deployed in, for example, an annulus of a native mitral valve. The valve 402 is configured to permit blood flow in a first direction through an inflow end of the valve 402 and to block blood flow in a second direction, opposite the first direction, through an outflow end of the valve 402. The valve 402 is compressible and expandable between an expanded configuration for implanting in an annulus of a target valve (e.g., in a human heart) and a compressed configuration for introduction into the body using a delivery catheter (not shown in FIGS. 4A and 4B).

The valve 402 includes an annular outer support frame 410 and a collapsible flow control component 450 mounted within the annular outer support frame 410. The annular outer support frame 410 (also referred to herein as "outer frame") is made from a shape-memory material such as Nickel-Titanium alloy, for example Nitinol, and is therefore a self-expanding structure from a compressed configuration to an expanded configuration. At least a portion of the outer frame 410 is covered, wrapped, and/or surrounded by a biocompatible cover 440 such as those described above.

The outer frame 410 has a transannular and/or body section 412 that circumscribes, forms, and/or defines a central (interior) channel 414 about and/or along the vertical or central axis (y-axis), and has an atrial collar 420 attached circumferentially at a top edge of the transannular and/or body section 412 of the outer frame 410. The outer frame 410 has a proximal side 419 and a distal side 422.

The collapsible (inner) flow control component 450 is mounted within the outer frame 410 adjacent to a covered or uncovered spacer 430. The flow control component 450 has an inner frame 452 with two or more fold areas, hinge areas, coupling areas, elastically deformable regions, etc. A set of 2-4 flexible leaflets 461 are mounted in or on the inner frame 452. The inner flow control component 450, like the outer frame 410, is foldable and compressible. The flow control component 450 is mounted to or within the outer frame 410 such that a central or vertical axis (y-axis) of the inner frame 452 is coaxial with and/or at least parallel to (e.g., parallel to but offset from) the central axis (y-axis) of the outer frame 410.

FIGS. 4A and 4B further show the valve 402 includes a distal anchoring element 432, an anterior anchoring element 435, and a sleeve 436. The distal anchoring element 432 (e.g., a superelastic wire loop distal tab) is coupled to and/or extends from the distal side 422. In some embodiments, the distal anchoring element 432 is an integrated tab that is unitarily constructed with the body section 412 of the outer frame 410. In some embodiments, the shape of the distal anchoring element 432 is configured to conform to the A1 commissural areas of the mitral valve and can be transitioned between, for example, a compressed, contracted, and/or folded configuration (e.g., a first configuration) and an extended or unfolded configuration (e.g., a second configuration). In some implementations, the distal anchoring element 432 can be configured in the extended configuration to reach around the P2 and/or P3 leaflets of a native mitral valve and/or chordae associated therewith and can be transitioned to the compressed configuration to capture and/or pin native tissue, chordae, etc., between the distal anchoring element 432 and the transannular section 412 of the outer frame 410.

The anterior anchoring element 435 and the sleeve 436 are mounted on an anterior side of the transannular section 412 of the outer frame 410. At least a portion of the anterior anchoring element 435 is disposed in the sleeve 436. The anterior anchoring element 435 is reconfigurable between a first configuration (e.g., a retracted) and a second configuration (e.g., extended). In some implementations, the anterior anchoring element 435 can be extended (e.g., to the second configuration) subannularly during deployment of the valve 402 (e.g., after at least partially seating the valve 402 in the annulus) such that a portion of the anterior anchoring element 435 extends from the sleeve 436 to engage and/or capture native leaflet tissue (e.g., the A2 leaflet, tissue, chordae, etc.). The anterior anchoring element 435 can be retracted (e.g., to the first configuration) to capture and secure the tissue between the anterior anchoring element 435 and the transannular section 412 of the outer frame 410.

In some embodiments, the anterior anchoring element 435 can be actuated and/or transitioned using a steerable catheter and/or a guide wire. In some embodiments, the anterior anchoring element 435 and/or the sleeve 436 can include imaging markers or the like that can help guide the steerable catheter or guide wire to the anterior anchoring element 435. While the anterior anchoring element 435 is described as being moved, actuated, and/or transitioned relative to the sleeve 436, in some embodiments, the sleeve 436 can be retracted or moved relative to the anterior anchoring element 435 to expose a larger portion thereof allowing the anterior anchoring element 435 to engage native tissue. In some embodiments, both the anterior anchoring element 435 and the sleeve 436 can be actuated, transitioned, moved, and/or reconfigured.

In some implementations, the use of an anterior anchoring element 435 on one side (A2) and a wrap-around distal anchoring element 432 on an opposite side (P2) can provide oppositional anchoring and securement and can reduce micro-motion and encourage in-growth success of the valve.

Figure 5A:
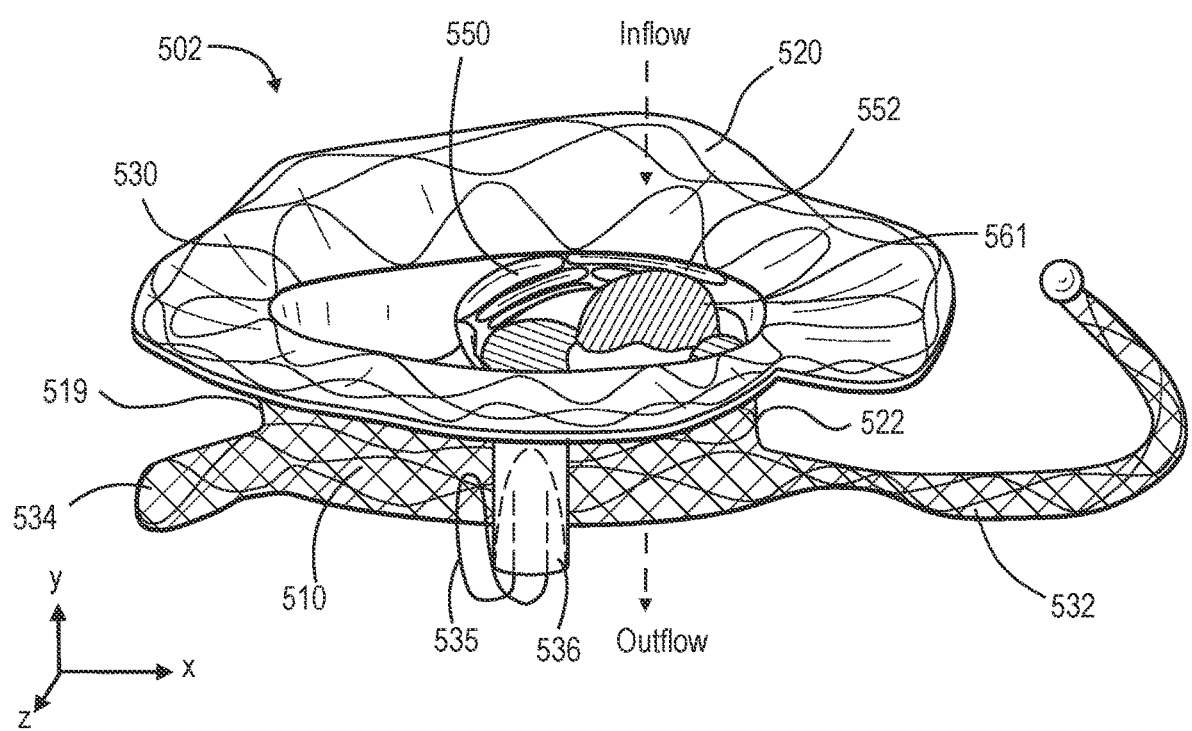
FIGS. 5A and 5B are illustrations of a side perspective view and an exploded view, respectively, of a side deliverable transcatheter prosthetic heart valve with an extendable distal anchoring element, an anterior anchoring element, and a proximal anchoring element, according to an embodiment.
Figure 5B:
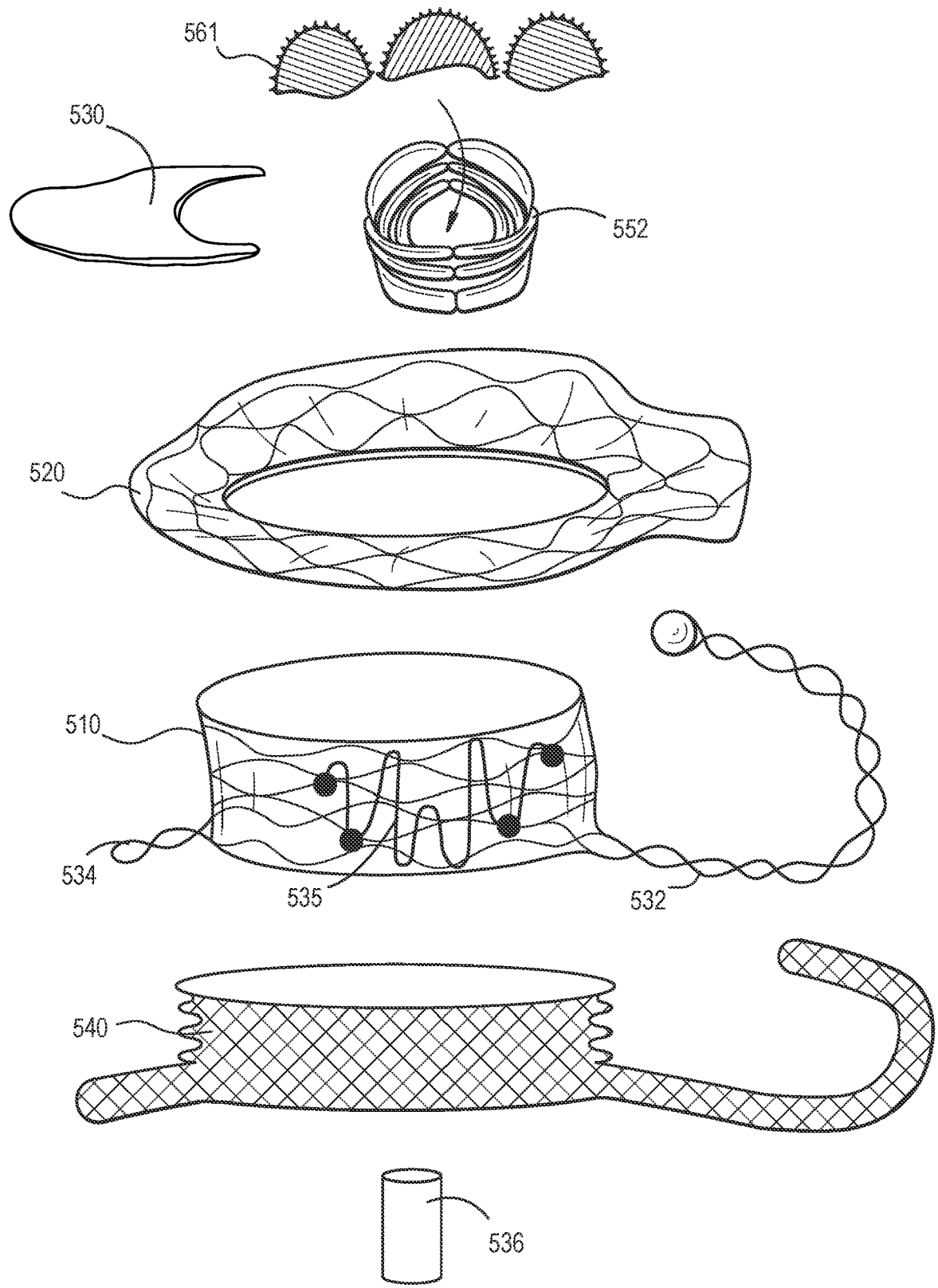

FIGS. 5A and 5B are illustrations of a side perspective view and an exploded view, respectively, of a side-deliverable (orthogonally deliverable) transcatheter prosthetic heart valve 502 (also referred to herein as "prosthetic valve" or "valve"), according to an embodiment. In some implementations, the valve 502 can be deployed in, for example, an annulus of a native mitral valve. The valve 502 is configured to permit blood flow in a first direction through an inflow end of the valve 502 and to block blood flow in a second direction, opposite the first direction, through an outflow end of the valve 502. The valve 502 is compressible and expandable between an expanded configuration for implanting in an annulus of a target valve (e.g., in a human heart) and a compressed configuration for introduction into the body using a delivery catheter (not shown in FIGS. 5A and 5B).

The valve 502 includes an annular outer support frame 510 and a collapsible flow control component 550 mounted within the annular outer support frame 510. The annular outer support frame 510 (also referred to herein as "outer frame") is made from a shape-memory material such as Nickel-Titanium alloy, for example Nitinol, and is therefore a self-expanding structure from a compressed configuration to an expanded configuration. At least a portion of the outer frame 510 is covered, wrapped, and/or surrounded by a biocompatible cover 540 such as those described above.

The outer frame 510 has a transannular and/or body section 512 that circumscribes, forms, and/or defines a central (interior) channel 514 about and/or along the vertical or central axis (y-axis), and has an atrial collar 520 attached circumferentially at a top edge of the transannular and/or body section 512 of the outer frame 510. The outer frame 510 has a proximal side 519 and a distal side 522.

The collapsible (inner) flow control component 550 is mounted within the outer frame 510 adjacent to a covered or uncovered spacer 530. The flow control component 550 has an inner frame 552 with two or more fold areas, hinge areas, coupling areas, elastically deformable regions, etc. A set of 2-4 flexible leaflets 561 are mounted in or on the inner frame 552. The inner flow control component 550, like the outer frame 510, is foldable and compressible. The flow control component 550 is mounted to or within the outer frame 510 such that a central or vertical axis (y-axis) of the inner frame 552 is coaxial with and/or at least parallel to (e.g., parallel to but offset from) the central axis (y-axis) of the outer frame 510.

FIGS. 5A and 5B further show the valve 502 includes a distal anchoring element 532, a proximal anchoring element 534, an anterior anchoring element 535, and a sleeve 536. The distal anchoring element 532 (e.g., a superelastic wire loop distal tab) is coupled to and/or extends from the distal side 522 of the outer frame 510 and the proximal anchoring element 534 (e.g., a superelastic wire loop proximal tab) is coupled to and/or extends from the proximal side 519 of the outer support frame 510. In some embodiments, the distal anchoring element 532 and the proximal anchoring element 534 can be integrated tabs that are unitarily constructed with the body section 512 of the outer frame 510. The anterior anchoring element 535 and the sleeve 536 are mounted on an anterior side of the transannular section 512 of the outer frame 510. At least a portion of the anterior anchoring element 535 is disposed in the sleeve 536. The anchoring elements 532, 534, and/or 535 may vary in size and shape. For example, in some embodiments, the shape of the distal anchoring element 532 is configured to conform to the A1 commissural area of the mitral valve; the shape of the proximal anchoring element 534 is configured to conform to the A3 commissural area of the mitral valve; and the shape of the anterior proximal anchoring element 535 is configured to conform to the A2 commissural area of the mitral valve.

In some embodiments, the distal anchoring element 532 can be transitioned between, for example, a compressed, contracted, and/or folded configuration (e.g., a first configuration) and an extended or unfolded configuration (e.g., a second configuration). In the extended configuration, the distal anchoring element 532 can reach around the P2 and/or P3 leaflets of a native mitral valve and/or chordae associated therewith and when transitioned to the compressed configuration, the distal anchoring element 532 can capture and/or pin native tissue, chordae, etc., between the distal anchoring element 532 and the transannular section 512 of the outer frame 510.

In some embodiments, the anterior anchoring element 535 is reconfigurable between a first configuration (e.g., a retracted) and a second configuration (e.g., extended). In some implementations, the anterior anchoring element 535 can be extended (e.g., to the second configuration) subannularly during deployment of the valve 502 (e.g., after at least partially seating the valve 502 in the annulus) such that a portion of the anterior anchoring element 535 extends from the sleeve 536 to engage and/or capture native leaflet tissue (e.g., the A2 leaflet, tissue, chordae, etc.). The anterior anchoring element 535 can be retracted (e.g., to the first configuration) to capture and secure the tissue between the anterior anchoring element 535 and the transannular section 512 of the outer frame 510. In some embodiments, the distal anchoring element 532 and/or the anterior anchoring element 535 can be actuated and/or transitioned using a steerable catheter and/or the guide wire. In some implementations, retracting the guide wire can allow the distal anchoring element 532 and/or the anterior anchoring element 535 to transition from, for example, the extended configurations to the retracted or folded configurations.

Figure 6A:
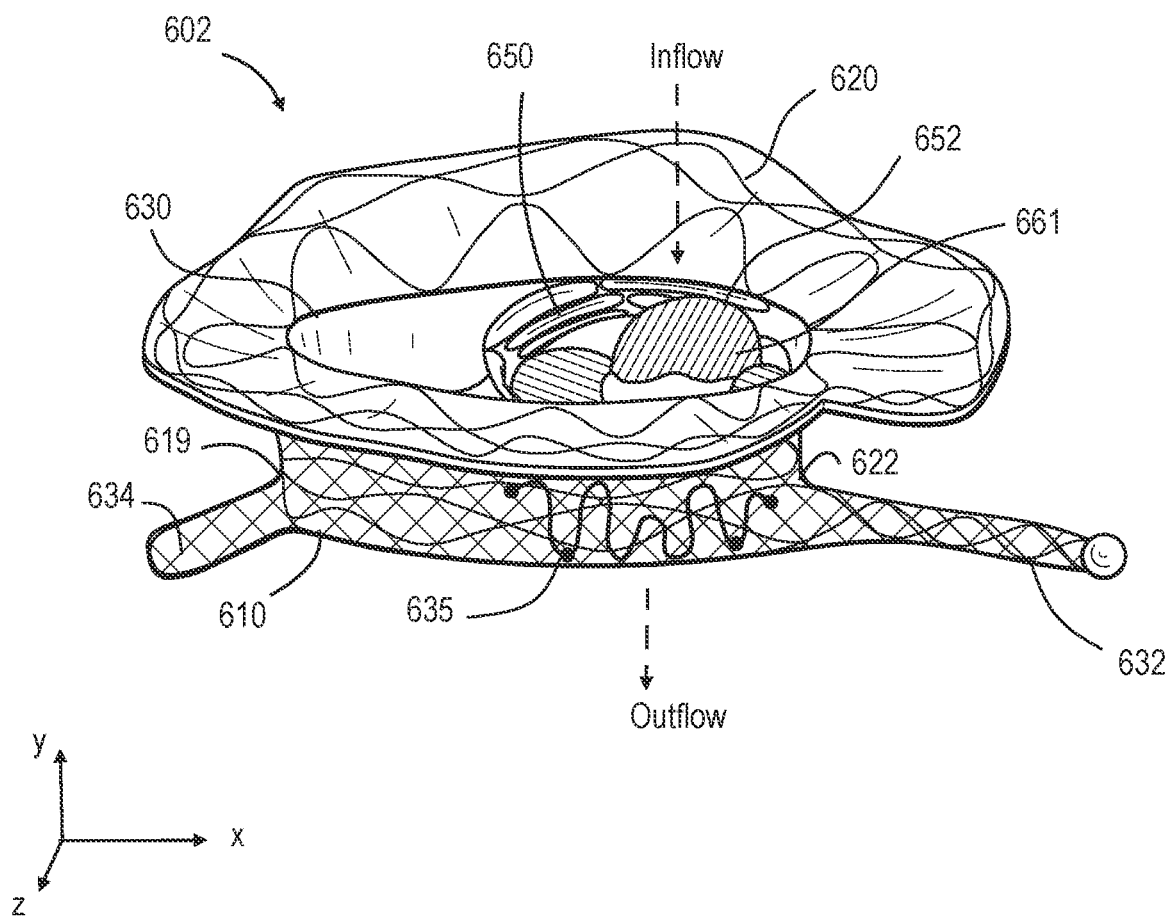
FIGS. 6A and 6B are illustrations of a side perspective view and an exploded view, respectively, of a side deliverable transcatheter prosthetic heart valve with an extendable distal anchoring element and an anterior anchoring element, according to an embodiment.
Figure 6B:
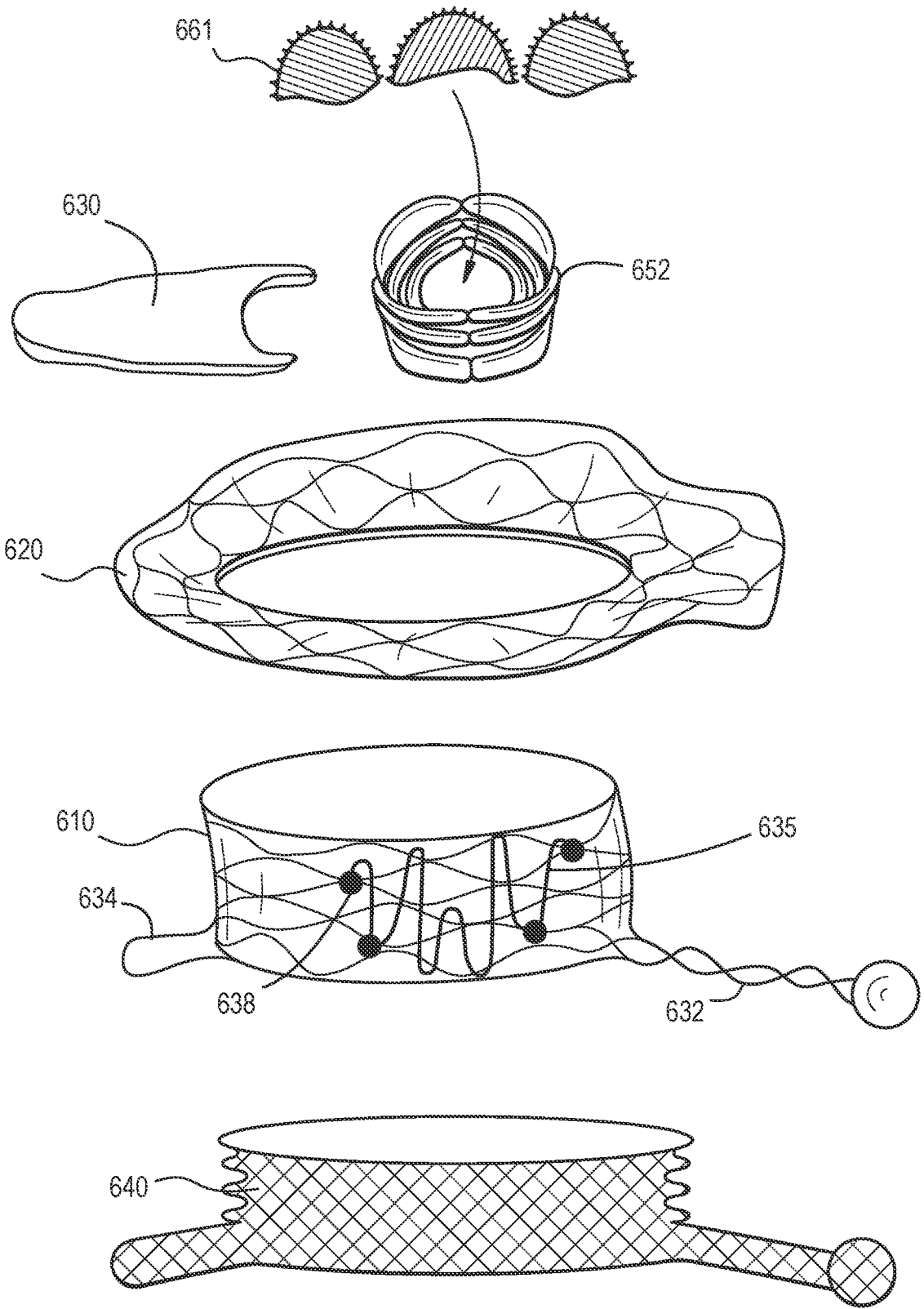

FIGS. 6A and 6B are illustrations of a side perspective view and an exploded view, respectively, of a side-deliverable (orthogonally deliverable) transcatheter prosthetic heart valve 602 (also referred to herein as "prosthetic valve" or "valve"), according to an embodiment. In some implementations, the valve 602 can be deployed in, for example, an annulus of a native mitral valve. The valve 602 is configured to permit blood flow in a first direction through an inflow end of the valve 602 and to block blood flow in a second direction, opposite the first direction, through an outflow end of the valve 602. The valve 602 is compressible and expandable between an expanded configuration for implanting in an annulus of a target valve (e.g., in a human heart) and a compressed configuration for introduction into the body using a delivery catheter (not shown in FIGS. 6A and 6B).

The valve 602 includes an annular outer support frame 610 and a collapsible flow control component 650 mounted within the annular outer support frame 610. The annular outer support frame 610 (also referred to herein as "outer frame") is made from a shape-memory material such as Nickel-Titanium alloy, for example Nitinol, and is therefore a self-expanding structure from a compressed configuration to an expanded configuration. At least a portion of the outer frame 610 is covered, wrapped, and/or surrounded by a biocompatible cover 640 such as those described above.

The outer frame 610 has a transannular and/or body section 612 that circumscribes, forms, and/or defines a central (interior) channel 614 about and/or along the vertical or central axis (y-axis), and has an atrial collar 620 attached circumferentially at a top edge of the transannular and/or body section 612 of the outer frame 610. The outer frame 610 has a proximal side 619 and a distal side 622.

The collapsible (inner) flow control component 650 is mounted within the outer frame 610 adjacent to a covered or uncovered spacer 630. The flow control component 650 has an inner frame 652 with two or more fold areas, hinge areas, coupling areas, elastically deformable regions, etc. A set of 2-4 flexible leaflets 661 are mounted in or on the inner frame 652. The inner flow control component 650, like the outer frame 610, is foldable and compressible. The flow control component 650 is mounted to or within the outer frame 610 such that a central or vertical axis (y-axis) of the inner frame 652 is coaxial with and/or at least parallel to (e.g., parallel to but offset from) the central axis (y-axis) of the outer frame 610.

FIGS. 6A and 6B further show the valve 602 includes a distal anchoring element 632, a proximal anchoring element 634, and an anterior anchoring element 635. The distal anchoring element 632 (e.g., a superelastic wire loop distal tab) is coupled to and/or extends from the distal side 622 of the outer frame 610 and the proximal anchoring element 634 (e.g., a superelastic wire loop proximal tab) is coupled to and/or extends from the proximal side 619 of the outer support frame 610. In some embodiments, the distal anchoring element 632 and the proximal anchoring element 634 can be integrated tabs that are unitarily constructed with the body section 612 of the outer frame 610. In the embodiment shown in FIGS. 6A and 6B, the anterior anchoring element 635 is not disposed in a sleeve, as described above with reference to the anchoring element 535. Rather, the anterior anchoring element 635 is mounted on an anterior side of the transannular section 612 of the outer frame 610 via one or more attachment points 638.

The anchoring elements 632, 634, and/or 635 may vary in size and shape. For example, in some embodiments, the shape of the distal anchoring element 632 is configured to conform to the A1 commissural area of the mitral valve; the shape of the proximal anchoring element 634 is configured to conform to the A3 commissural area of the mitral valve;

and the shape of the anterior proximal anchoring element 635 is configured to conform to the A2 commissural area of the mitral valve.

In some embodiments, the distal anchoring element 632 can be transitioned between, for example, a compressed, contracted, and/or folded configuration (e.g., a first configuration) and an extended or unfolded configuration (e.g., a second configuration). In the extended configuration, the distal anchoring element 632 can reach around the P2 and/or P3 leaflets of a native mitral valve and/or chordae associated therewith and when transitioned to the compressed configuration, the distal anchoring element 632 can capture and/or pin native tissue, chordae, etc., between the distal anchoring element 632 and the transannular section 612 of the outer frame 610.

In some embodiments, the anterior anchoring element 635 is reconfigurable between a first configuration (e.g., a retracted) and a second configuration (e.g., extended). In some implementations, the anterior anchoring element 635 can be extended (e.g., to the second configuration) subannularly during deployment of the valve 602 to engage and/or capture native leaflet tissue (e.g., the A2 leaflet, tissue, chordae, etc.). The anterior anchoring element 635 can be retracted (e.g., to the first configuration) to capture and secure the tissue between the anterior anchoring element 635 and the transannular section 612 of the outer frame 610. In some embodiments, the distal anchoring element 632 and/or the anterior anchoring element 635 can be actuated and/or transitioned using a steerable catheter and/or the guide wire. In some implementations, retracting the guide wire can allow the distal anchoring element 632 and/or the anterior anchoring element 635 to transition from, for example, the extended configurations to the retracted or folded configurations.

Figure 7A:
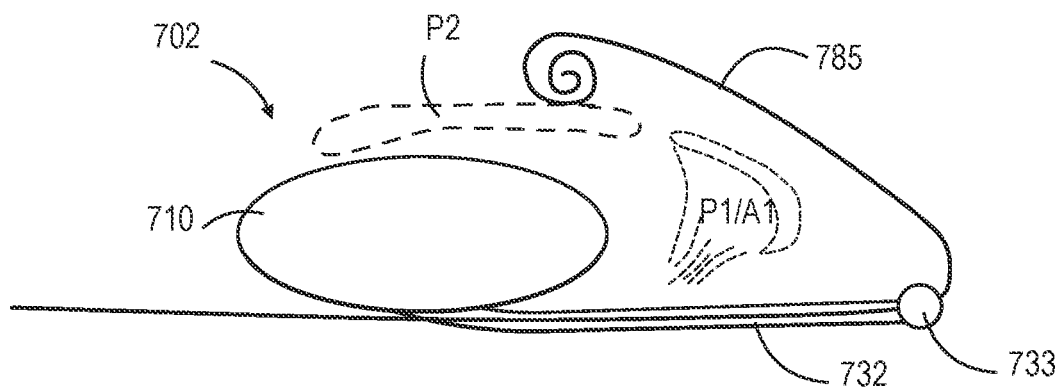
FIGS. 7A-7D are a series of illustrations showing a process of a distal anchoring element of a side deliverable transcatheter prosthetic heart valve capturing native tissue, according to an embodiment.
Figure 7B:
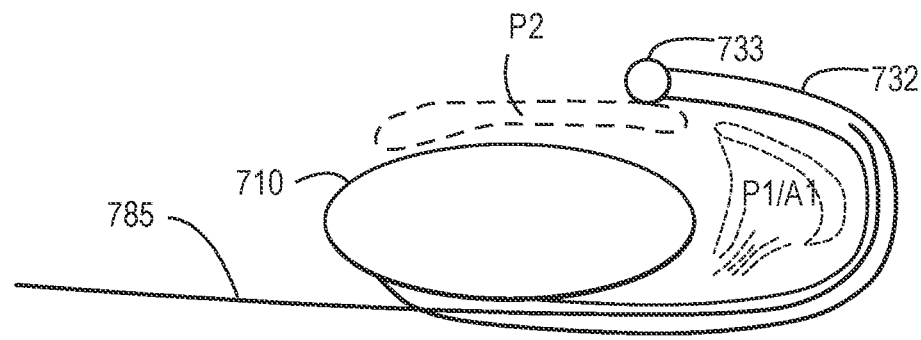
Figure 7C:
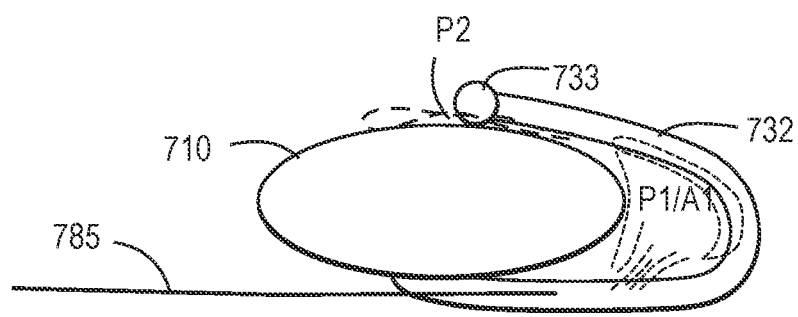
Figure 7D:
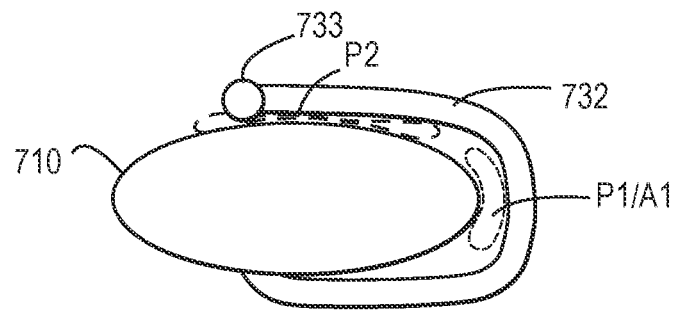
Figure 7E:
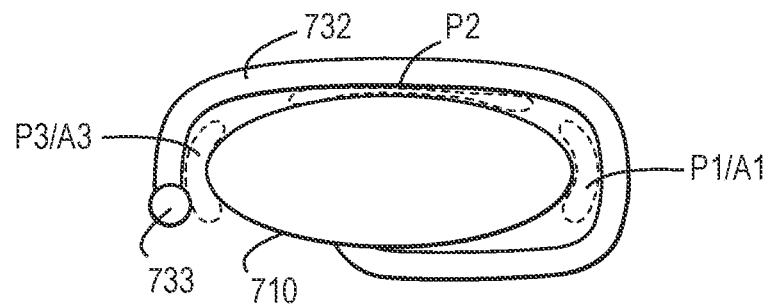
FIG. 7E is an illustration of a top view of the side deliverable transcatheter prosthetic heart valve of FIGS. 7A-7D showing the distal anchoring element wrapped around the prosthetic valve to capture native tissue, according to an embodiment.

FIGS. 7A-7E are a series of illustrations of a prosthetic valve 702 showing capture of native tissue P1, P2 by a distal anchoring element 732. FIG. 7A shows the distal anchoring element 732 tracking over a guide wire 785 to a desired position relative to the native tissue P1, P2. FIG. 7B shows the distal anchoring element 732 in the desired position and a withdrawal of the guide wire 785. The distal anchoring element 732 is actuated and/or contracted when the guide wire 785 is withdrawn (e.g., the distal anchoring element 732 can be a shape-memory device or the like). FIG. 7C shows the distal anchoring element 732 pulling the native tissue P1, P2 against a distal wall of an outer frame 710 of the valve 702. FIG. 7D shows a completed capture of the native tissue P1, P2 and anchoring of the valve 702 with the distal anchoring element 732 pressing the native tissue against the outer frame 710 to facilitate in-growth and reduce micro-motion of the valve. FIG. 7E shows that, in some implementations, the distal anchoring element 732 can be configured to wrap around substantially all or a relatively large portion of the valve 702 to capture P1/A1, P2, and P3/A3 native tissue.

Figure 8:
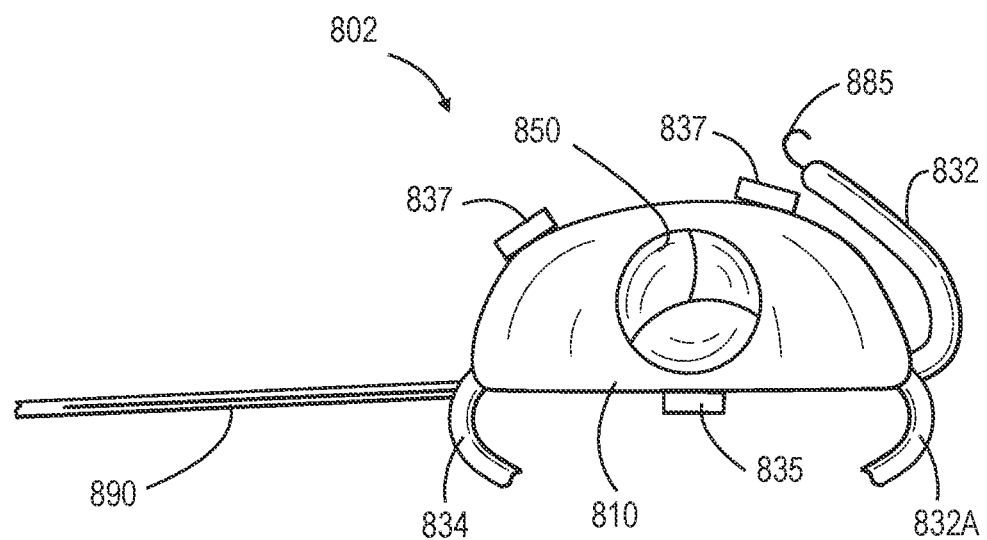
FIG. 8 is an illustration of a top view of a side deliverable transcatheter prosthetic heart valve having a number of anchoring elements, according to an embodiment.

FIG. 8 is an illustration of a top view of side deliverable transcatheter prosthetic valve 802, according to an embodiment. The prosthetic valve 802 has an outer frame 810 and a flow control component 850 mounted therein. The outer frame 810 is eccentric having a D-shape that can conform to a native annulus (e.g., an annulus of a native mitral valve). The outer frame 810 can also be slightly over-sized (e.g., by about 10-15% for a particular patient anatomy, as determined by pre-operative planning and inter-operative or pre-operative imaging).

The outer frame 810 includes and/or is coupled to a distal anchoring element 832 that can track over a guide wire 885.

In addition, the prosthetic valve 802 and/or outer frame 810 includes or is coupled to a proximal anchoring element 834, an anterior anchoring element 835, and two posterior anchoring elements 837. FIG. 8 also shows a positioning tool 890 (e.g., a catheter such as, for example, a guide wire catheter) that can engage and/or transition any of the anchoring elements 832, 834, 835, and/or 837 to capture native leaflet and or chordae. In some implementations, the positioning tool 890 can initially advance the valve 802 out of a delivery catheter (not shown), and secondarily can steer and/or position the valve 802 within the annulus or one or more of the anchoring elements 832, 834, 835, and/or 837 relative to the annulus. In some embodiments, one or more of the posterior anchoring elements 837 can be configured to engage and/or contact a portion of the distal anchoring element 832 that wraps around the valve 802 to the posterior side. In such embodiments, the one or more posterior anchoring element 837 can secure the distal anchoring element 832 in a desired (e.g., wrapped) configuration.

FIG. 8 further shows that, in some embodiments, the outer frame 810 can include a distal stabilizing element 832A that is adjacent to the distal anchoring element 832. In some implementations, the distal stabilizing element 832A can contact subannular tissue to stabilize, reduce, and/or minimize undesirable rotation or twisting of the valve 802 relative to the annulus.

Figure 9A:
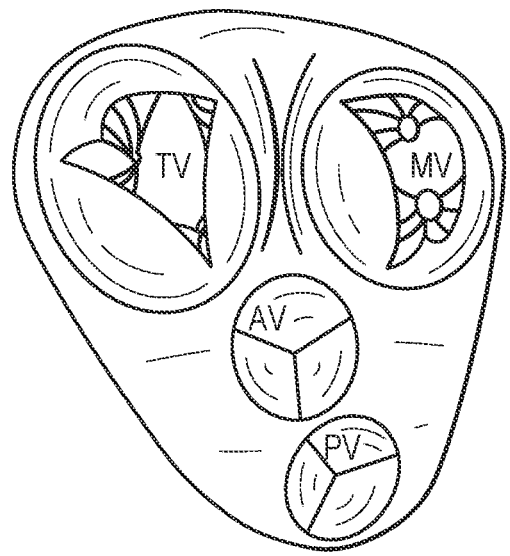
FIG. 9A is an illustration of a cross-sectional view of a human heart showing the relative locations of the mitral valve, the tricuspid valve, the aortic valve, and the pulmonary valve.

FIG. 9A is an illustration of a cross-sectional view of a human heart showing the relative locations of the mitral valve (MV), the tricuspid valve (TV), the aortic valve (AV), and the pulmonary valve (PV), according to an embodiment.

Figure 9B:
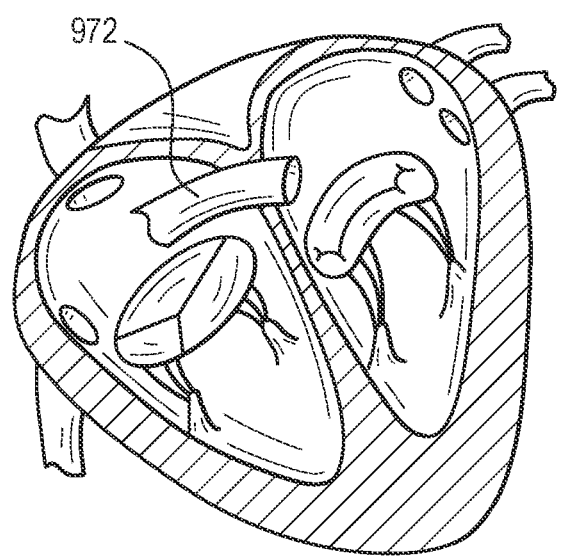
FIG. 9B is an illustration of a cut-away side view of the human heart having a trans-septal (trans-femoral/inferior vena cava (IVC) or superior vena cava (SVC)) delivery catheter crossing from the right atrium to the left atrium for access to the mitral valve, according to an embodiment.

FIG. 9B is an illustration of a side view of a human heart having a trans-septal (trans-femoral/IVC or SVC) delivery catheter 972 crossing from the right atrium to the left atrium for access to the mitral valve, according to an embodiment. The delivery catheter 972 can be used, for example, to orthogonally or side deliver a transcatheter prosthetic mitral valve such as any of those described herein.

Figure 10:
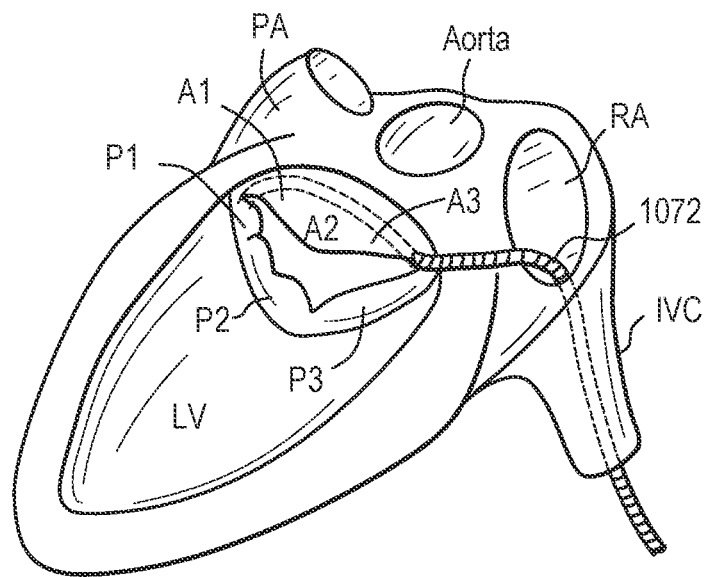
FIGS. 10 and 11 are illustrations of a perspective view and a side perspective view, respectively, of a guide wire accessing a native valve annulus through the IVC and wrapping under or around a native A2 leaflet, according to an embodiment.
Figure 11:
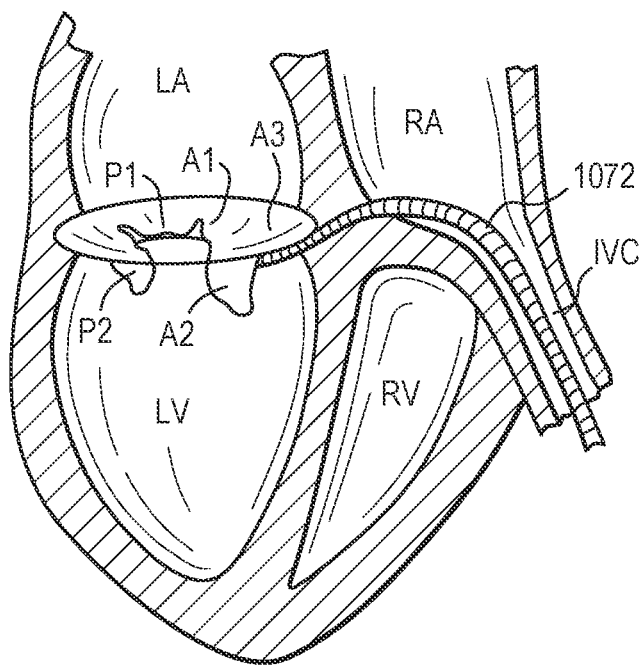

FIGS. 10 and 11 are illustrations of a side perspective view and a side view, respectively, of a delivery catheter 1072 (or guide wire 1085) accessing a native valve via the IVC and wrapping under and/or around a native A2 leaflet to access, for example, a P2 location of the native valve, according to an embodiment.

Figure 12:
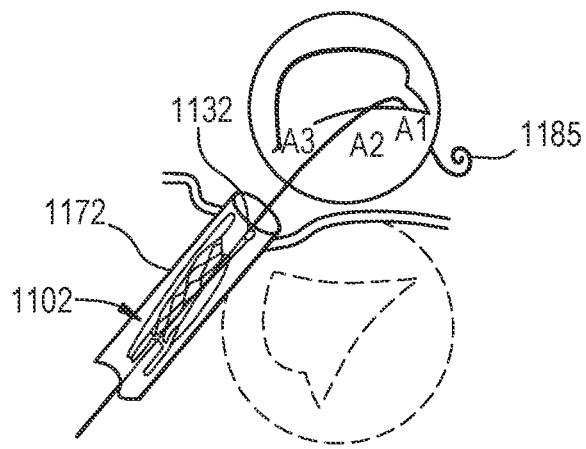
FIGS. 12-16 are various illustrations of a process of delivering and deploying a side deliverable transcatheter prosthetic heart valve in, for example, a native mitral valve, according to an embodiment.

FIGS. 12-16 are various illustrations of a process of delivering and deploying a side deliverable transcatheter prosthetic heart valve 1102 in, for example, a native mitral valve, according to an embodiment. FIG. 12 shows a guide wire 1185 directing the prosthetic valve 1102 to an A1 leaflet with the valve 1102 in a compressed configuration within a delivery catheter 1172, according to an embodiment. The prosthetic valve 1102 includes a distal anchoring element 1132 is disposed or threaded over the guide wire 1185 to guide the distal anchoring element 1132 (and thus, the valve 1102) into a desired deployment location.

Figure 13:
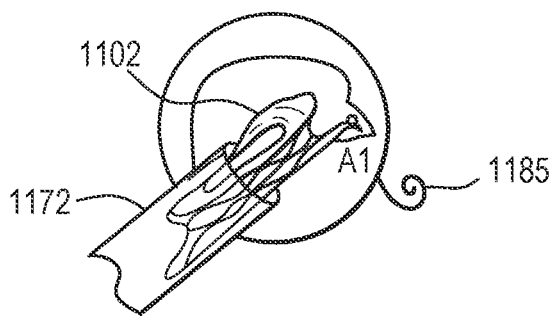

FIG. 13 shows the distal anchoring element 1132 being deployed in an A1 location of the native mitral valve. The valve 1102 is shown in a partial deployment stage being partially expelled from delivery catheter 1172.

Figure 14:
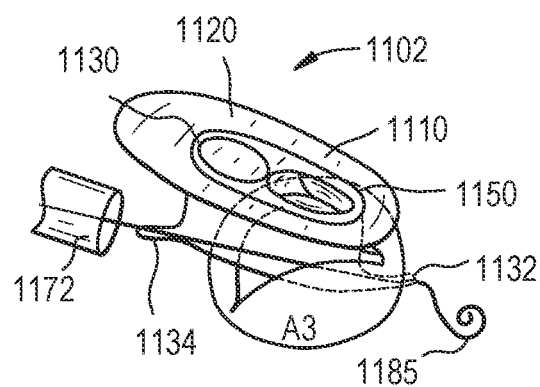

FIG. 14 shows an outer frame 1110, an atrial collar 1120, a flow control component 1150, and a spacer 130 of the prosthetic valve 1102. The valve 1102 is shown fully expelled from delivery catheter 1172 and positioned temporarily at an upwards angle with the distal anchoring element 132 in the A1 location the atrial collar about the annulus of the mitral valve. This angled positioning avoids a pop-off effect and allows the prosthetic valve 1102 to engage the blood flow while the native mitral valve continues to operate. A proximal anchoring element 1134 is shown above the annulus prior to a proximal side of the valve 1102 being shoe-horned into place anchoring the proximal side of the valve 1102.

Figure 15:
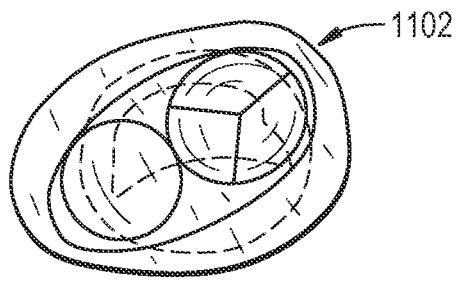
Figure 16:
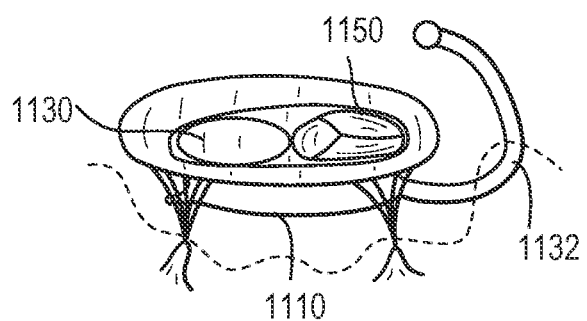

FIG. 15 is a top view showing the prosthetic valve 1102 deployed in the native annulus (visible in dashed line). FIG. 16 is a side perspective view of the prosthetic valve 1102 deployed in the native annulus (visible in dashed line). The flow control component 1150 is shown offset within the outer frame 1110 and disposed distally within the outer frame 1110 relative to a spacer 1130. The distal anchoring element 1132 is shown wrapping around a portion of the native tissue to secure the native tissue against a transannular section of the outer frame 1110.

Figure 17A:
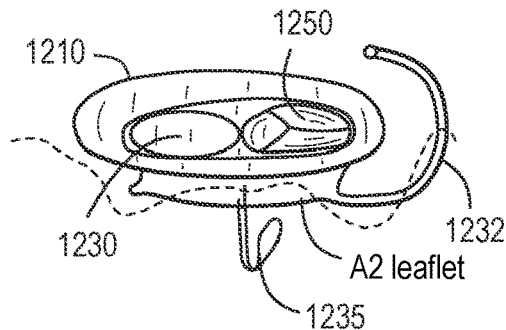
FIGS. 17A and 17B are illustrations of a side perspective view of a side deliverable transcatheter prosthetic heart valve deployed in a native annulus (in dashed line) with an anterior anchoring element in an extended position and a retracted position, respectively, according to an embodiment.
Figure 17B:
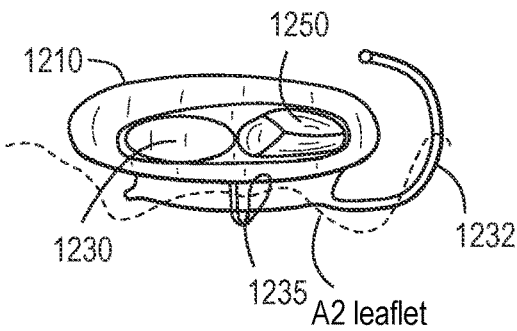

FIGS. 17A and 17B are side perspective views of a side deliverable transcatheter prosthetic heart valve 1202 deployed in an annulus of a native valve such as, for example, a native mitral valve (visible in dashed line), according to an embodiment. The prosthetic valve 1202 includes an outer frame 1210 with a flow control component 1250 mounted within a central channel of the outer frame 1210 and a spacer 1230 mounted adjacent to the flow control component 1250. The valve 1202 further includes a distal anchoring element 1232 coupled to and/or extending from a distal side of the outer frame 1210 and an anterior anchoring element 1235 coupled to and/or extending from an anterior side of the outer frame 1210.

FIG. 17A shows the valve 1202 deployed in the annulus with the distal anchoring element 1232 wrapping around a portion of the native tissue to secure the native tissue against a transannular section of the outer frame 1210. The anterior anchoring element 1235 is shown in an extended configuration to engage native tissue such as, for example, an A2 leaflet, chordae, and/or the like. FIG. 17B shows the anterior anchoring element 1235 in a retracted or compressed configuration in which the anterior anchoring element 1235 secures at least a portion of the A2 leaflet, chordae, and/or anterior native tissue against the transannular section of the outer frame 1210.

Figure 18A:
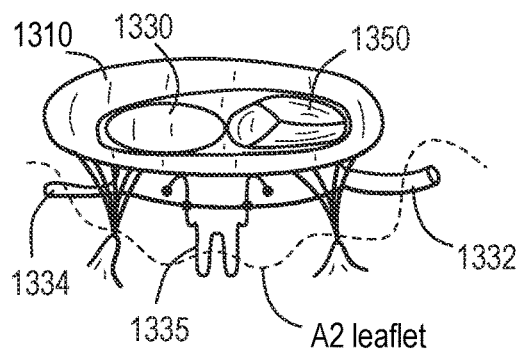
FIGS. 18A and 18B are illustrations of a side perspective view of a side deliverable transcatheter prosthetic heart valve deployed in a native annulus (in dashed line) with an anterior anchoring element in an extended position and a retracted position, respectively, according to an embodiment.
Figure 18B:
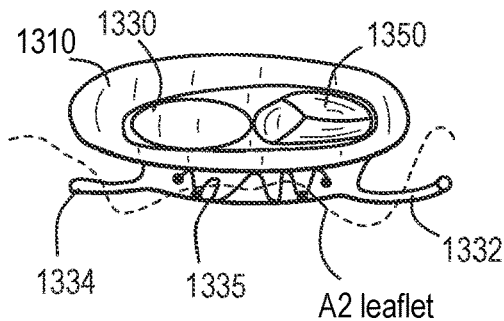

FIGS. 18A and 18B are side perspective views of a side deliverable transcatheter prosthetic heart valve 1302 deployed in an annulus of a native valve such as, for example, a native mitral valve (visible in dashed line), according to an embodiment. The prosthetic valve 1302 includes an outer frame 1310 with a flow control component 1350 mounted within a central channel of the outer frame 1310 and a spacer 1330 mounted adjacent to the flow control component 1350. The valve 1302 further includes a distal anchoring element 1332 coupled to and/or extending from a distal side of the outer frame 1310, a proximal anchoring element 1334 coupled to and/or extending from a proximal side of the outer frame 1310, and an anterior anchoring element 1335 coupled to and/or extending from an anterior side of the outer frame 1310.

FIG. 18A shows the valve 1302 deployed in the annulus with the distal anchoring element 1332 extending from the outer frame 1310 and engaging native tissue on a distal side of the annulus, and the proximal anchoring element 1334 extending from the outer frame 1310 and engaging native tissue on a proximal side of the annulus. The anterior anchoring element 1335 is shown in an extended configuration to engage native tissue such as, for example, an A2 leaflet, chordae, and/or the like. FIG. 18B shows the anterior anchoring element 1335 in a retracted or compressed configuration in which the anterior anchoring element 1335 secures at least a portion of the A2 leaflet, chordae, and/or anterior native tissue against the transannular section of the outer frame 1310.

Figure 19A:
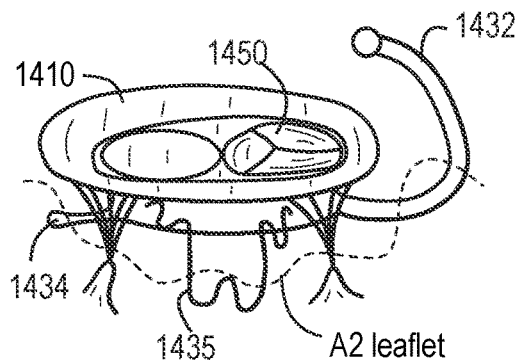
FIGS. 19A and 19B are illustrations of a side perspective view of a side deliverable transcatheter prosthetic heart valve deployed in a native annulus (in dashed line) with an anterior anchoring element in an extended position and a retracted position, respectively, according to an embodiment.
Figure 19B:
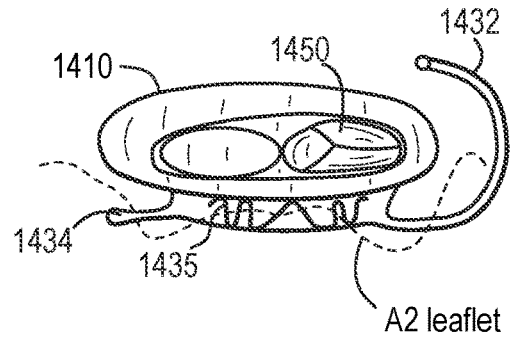

FIGS. 19A and 19B are side perspective views of a side deliverable transcatheter prosthetic heart valve 1402 deployed in an annulus of a native valve such as, for example, a native mitral valve (visible in dashed line), according to an embodiment. The prosthetic valve 1402 includes an outer frame 1410 with a flow control component 1450 mounted within a central channel of the outer frame 1410 and a spacer 1430 mounted adjacent to the flow control component 1450. The valve 1402 further includes a distal anchoring element 1432 coupled to and/or extending from a distal side of the outer frame 1410, a proximal anchoring element 1434 coupled to and/or extending from a proximal side of the outer frame 1410, and an anterior anchoring element 1435 coupled to and/or extending from an anterior side of the outer frame 1410.

FIG. 19A shows the valve 1402 deployed in the annulus with the distal anchoring element 1432 wrapping around a portion of the native tissue to secure the native tissue against a transannular section of the outer frame 1410. The proximal anchoring element 1334 is shown extending from the outer frame 1310 and engaging native tissue on a proximal side of the annulus. The anterior anchoring element 1435 is shown in an extended configuration to engage native tissue such as, for example, an A2 leaflet, chordae, and/or the like. FIG. 19B shows the anterior anchoring element 1435 in a retracted or compressed configuration in which the anterior anchoring element 1435 secures at least a portion of the A2 leaflet, chordae, and/or anterior native tissue against the transannular section of the outer frame 1410.

Figure 20:
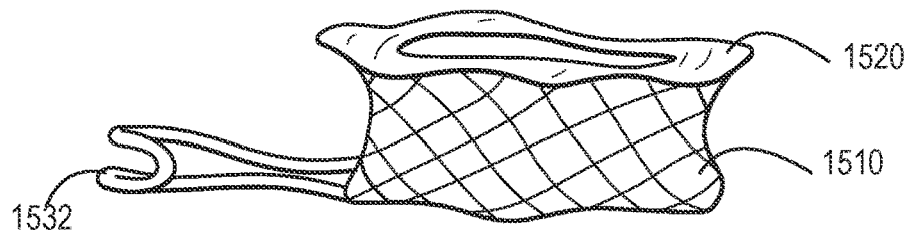
FIGS. 20 and 21 are illustrations of a side view and a top view, respectively, of a side deliverable transcatheter prosthetic heart valve having a distal anchoring element extending from a valve body, according to an embodiment.

FIGS. 20-24 are various illustrations of a process of delivering and deploying a side deliverable transcatheter prosthetic heart valve 1502 in, for example, a native mitral valve, according to an embodiment. FIG. 20 is a side view of the prosthetic valve 1502 in an expanded configuration and having a distal anchoring element 1532 extending from an outer frame 1510 of the prosthetic valve 1502. The outer frame 1510 is also shown including and/or being coupled to an atrial collar 1520.

Figure 21:
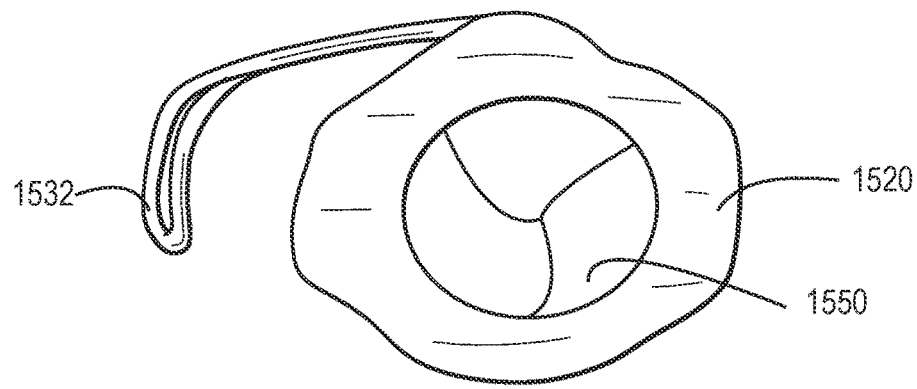

FIG. 21 is a top view of the prosthetic valve 1502 in the expanded configuration and showing the distal anchoring element 1532 extending from the outer frame 1510, the atrial collar 1520 coupled to and/or included in the outer frame 1510, and a flow control component 1550 mounted within a central channel of the outer frame 1510.

Figure 22:
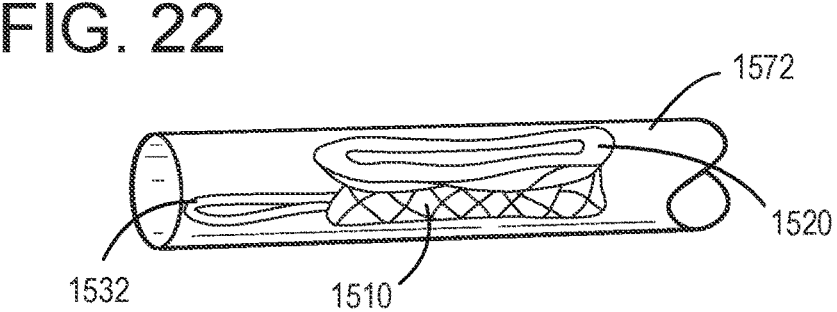
FIG. 22 is an illustration of the prosthetic valve of FIG. 20 in a compressed configuration and disposed within a delivery catheter.

FIG. 22 is a side view of the prosthetic valve 1502 in a compressed configured and disposed within a delivery catheter 1572 from delivery into an atrium of a heart. The valve 1502 is in an orthogonally folded and/or compressed configuration that allows the valve 1502 to be advanced through a lumen of the delivery catheter 1572.

Figure 23:
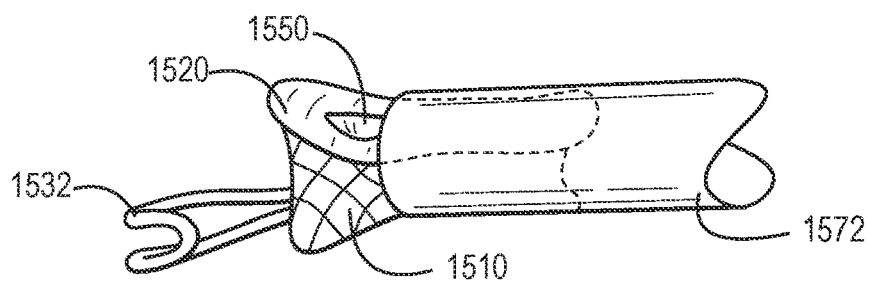
FIG. 23 is an illustration of the prosthetic valve of FIG. 20 in a partially expanded configuration and partially released from the delivery catheter.

FIG. 23 is a side view of the prosthetic valve 1502 partially released from the delivery catheter 1572 for deployment. The valve 1502 is configured to transition from the compressed configuration to the expanded configuration as the valve 1502 is released from the delivery catheter 1572. Moreover, the distal anchoring element 1532 is shown extending from the valve 1502 in a distal direction.

Figure 24:
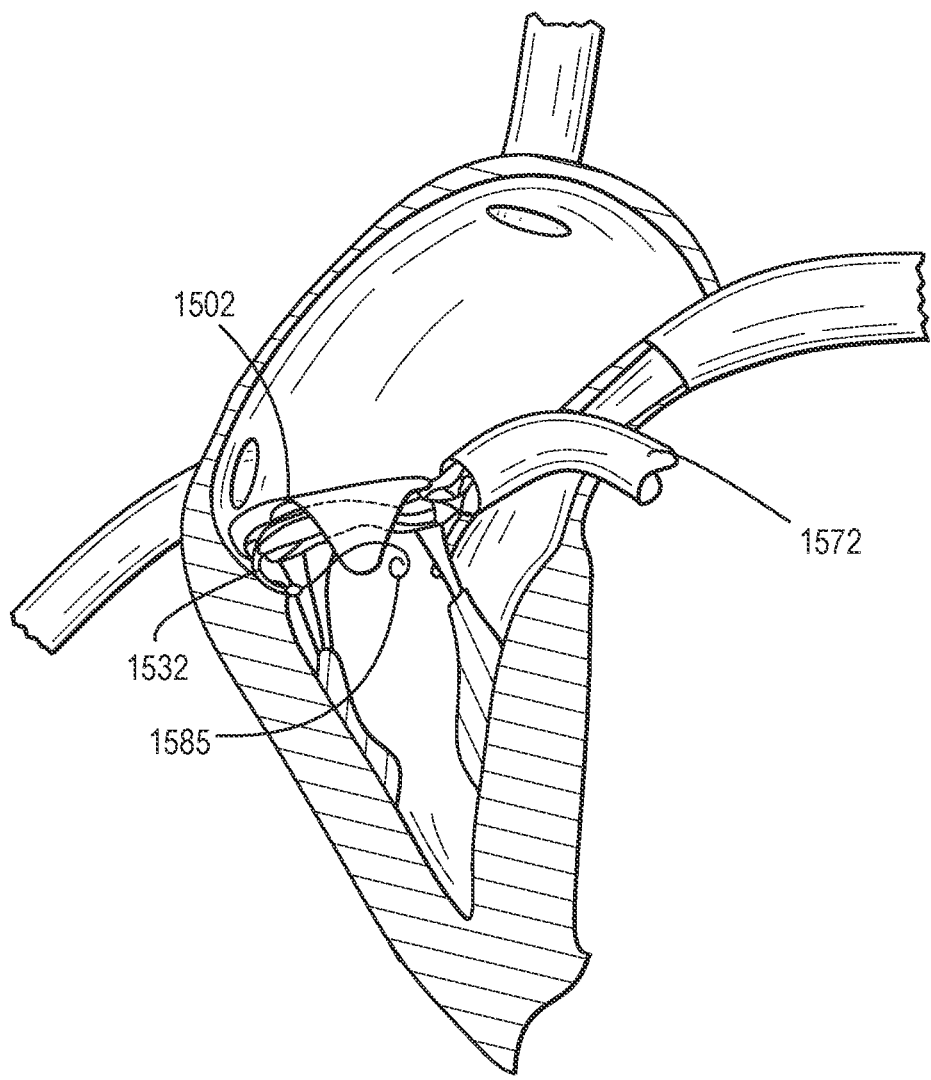
FIG. 24 is an illustration of a cut-away side view of the human heart and showing a side deliverable transcatheter prosthetic heart valve deployed in a native valve, according to an embodiment.

FIG. 24 is a side view of the delivery catheter 1572 at least partially disposed in the atrium of the heart and shown with the valve 1502 partially released from the delivery catheter 1572. The distal anchoring element 1532 is shown tracking over and/or along a guide wire 1585 in a process of capturing native tissue (e.g., native leaflet(s) and/or chordae).

FIGS. 25A-25E illustrate a side-delivered transcatheter prosthetic heart valve 1602 according to an embodiment, and shown being transitioned to a compressed configuration, loaded into a delivery catheter 1672 for transcatheter delivery to a native annulus of a heart, and partially released from the deliver catheter 1672 for deployment into the native annulus.

Figure 25A:
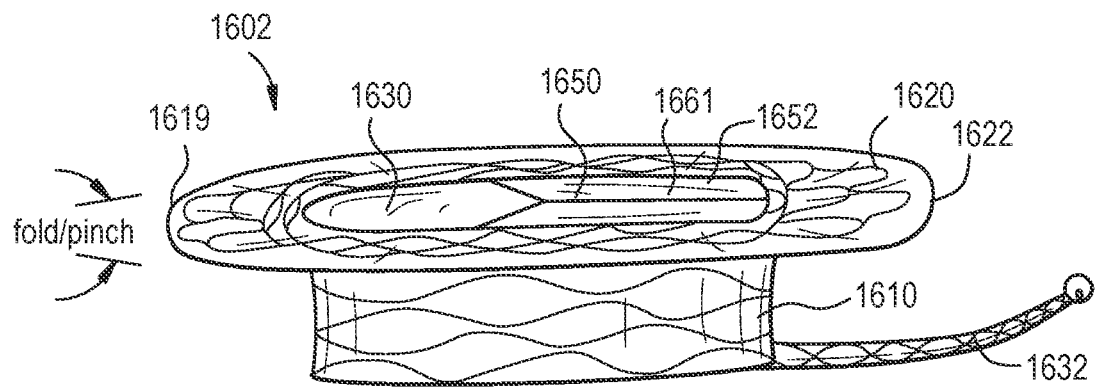
FIGS. 25A-25E illustrate various views of a process of placing a side deliverable transcatheter prosthetic heart valve in a compressed configuration, delivering the compressed prosthetic valve via a delivery catheter, and partially releasing the prosthetic valve from the delivery catheter for deployment in a native valve, according to an embodiment.

FIG. 25A shows the valve 1602 in a folded configuration along the z-axis (front to back when viewed from the broader side). FIG. 25A shows an outer frame 1610 with a flow control component 1650 and a spacer 1630 disposed within a central channel of the outer frame 1610. A distal anchoring element 1632 is shown extending from a distal side of the outer frame 1610. A collar 1620 of the outer frame 1610 is shown folded/flattened at proximal and distal hinge points or fold areas 1619 and 1622. The flow control component 1650 is shown including leaflets 1661 that are mounted within a folded/flattened inner frame 1652.

Figure 25B:
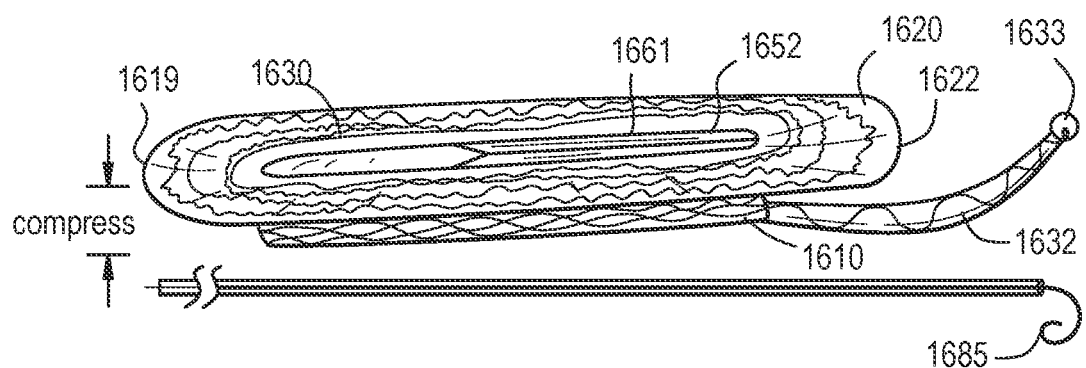

FIG. 25B shows the valve 1602 in a vertically compressed configuration. For example, the valve 1602 is laterally folded (e.g., in the direction of the z-axis, at the hinge points and/or fold areas 1619 and 1622 of the outer frame 1610) and compressed vertically (e.g., in the direction of the y-axis). The flow control component 1650 and the spacer 1630 are also folded and compressed. FIG. 25B also shows a guide wire 1685, which can be threaded through a guide wire coupler 1633 of the distal anchoring element 1632.

Figure 25C:
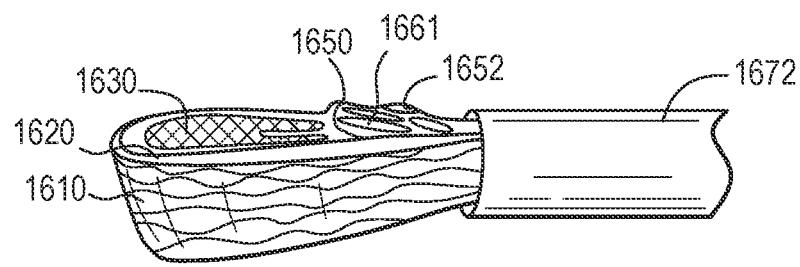

FIG. 25C shows the valve 1602 partially loaded into the delivery catheter 1672. The outer frame 1610, the folded collar 1620, the spacer 1630, and the flow control component 1650 having the leaflets 1661 and the inner frame 1652 are in and/or are being transitioned into a folded and compressed configuration.

Figure 25D:
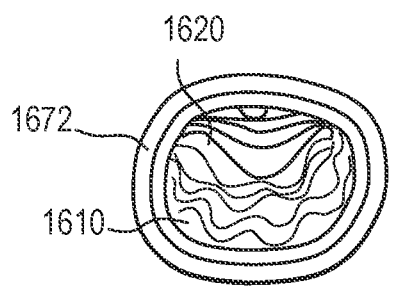

FIG. 25D is an end view of the delivery catheter 1672 that shows the loaded valve 1602 in the folded and compressed configuration.

Figure 25E:
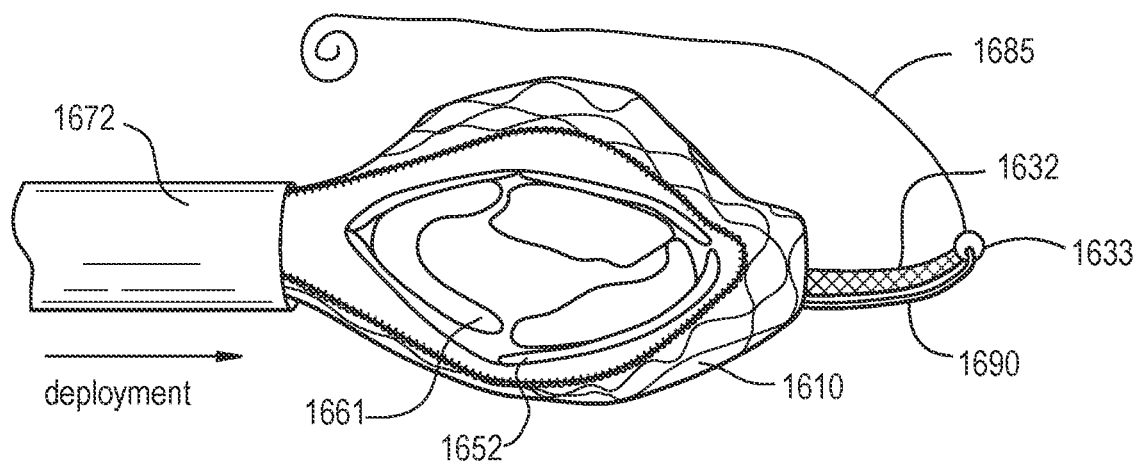

FIG. 25E shows the folded and compressed valve 1602 being released from the delivery catheter 1672, and beginning to transition from the folded and compressed configuration to an expanded configuration for deployment into the native annulus. The guide wire coupler 1633 of the distal anchoring element 1632 is shown disposed or threaded over the guide wire 1685.

Figure 26A:
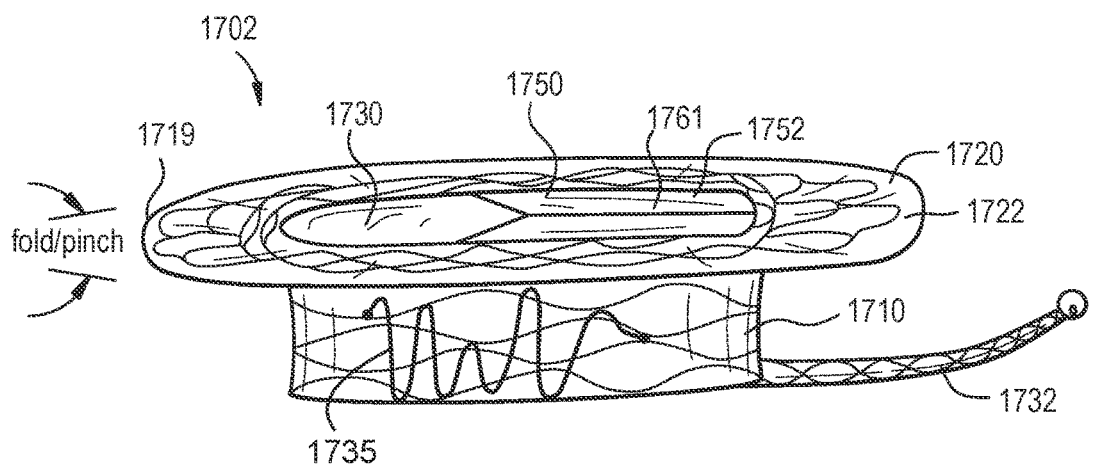
FIGS. 26A-26C illustrate various views of a process of placing a side deliverable transcatheter prosthetic heart valve in a compressed configuration and loading the compressed prosthetic valve in a delivery catheter, according to an embodiment.
Figure 26B:
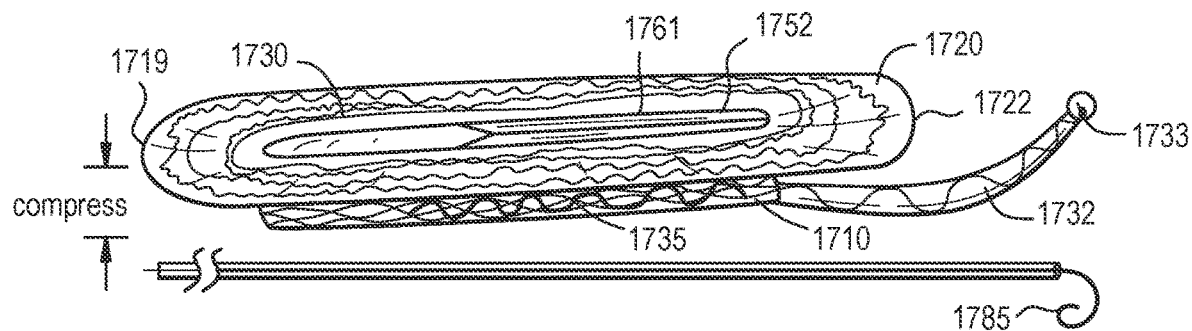
Figure 26C:
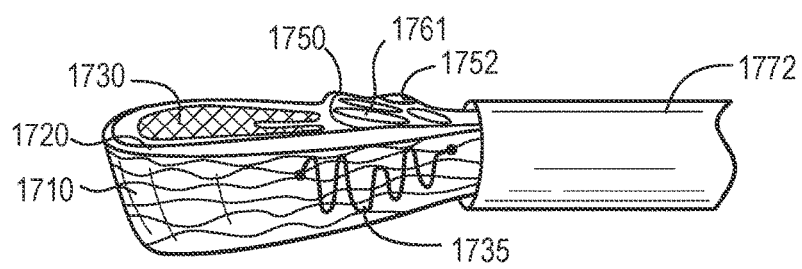

FIGS. 26A-26C illustrate a side-delivered transcatheter prosthetic heart valve 1702 according to an embodiment, and shown being transitioned to a compressed configuration and loaded into a delivery catheter 1772 for transcatheter delivery to a native annulus of a heart.

FIG. 26A shows the valve 1702 in a folded configuration along the z-axis (front to back when viewed from the broader side). FIG. 26A shows an outer frame 1710 with a flow control component 1750 and a spacer 1730 disposed within a central channel of the outer frame 1710. A distal anchoring element 1732 is shown extending from a distal side of the outer frame 1710. An anterior anchoring element 1735 is shown mounted to an anterior side of the outer frame 1710. The anterior anchoring element 1735 is in a non-extended or unactuated configuration. A collar 1720 of the outer frame 1710 is shown folded/flattened at proximal and distal hinge points or fold areas 1719 and 1722. The flow control component 1750 is shown including leaflets 1761 that are mounted within a folded/flattened inner frame 1752.

FIG. 26B shows the valve 1702 in a vertically compressed configuration. For example, the valve 1702 is laterally folded (e.g., in the direction of the z-axis, at the hinge points and/or fold areas 1719 and 1722 of the outer frame 1710) and compressed vertically (e.g., in the direction of the y-axis). The flow control component 1750 and the spacer 1730 are also folded and compressed. The anterior anchoring element 1735 is shown vertically compressed in response to the vertical compression of the outer frame 1710. FIG. 26B also shows a guide wire 1785, which can be threaded through a guide wire coupler 1733 of the distal anchoring element 1732.

FIG. 26C shows the valve 1702 partially loaded into the delivery catheter 1772. The outer frame 1710 having the anterior anchoring element 1735, the folded collar 1720, the spacer 1730, and the flow control component 1750 having the leaflets 1761 and the inner frame 1752 are in and/or are being transitioned into a folded and compressed configuration.

Figure 27A:
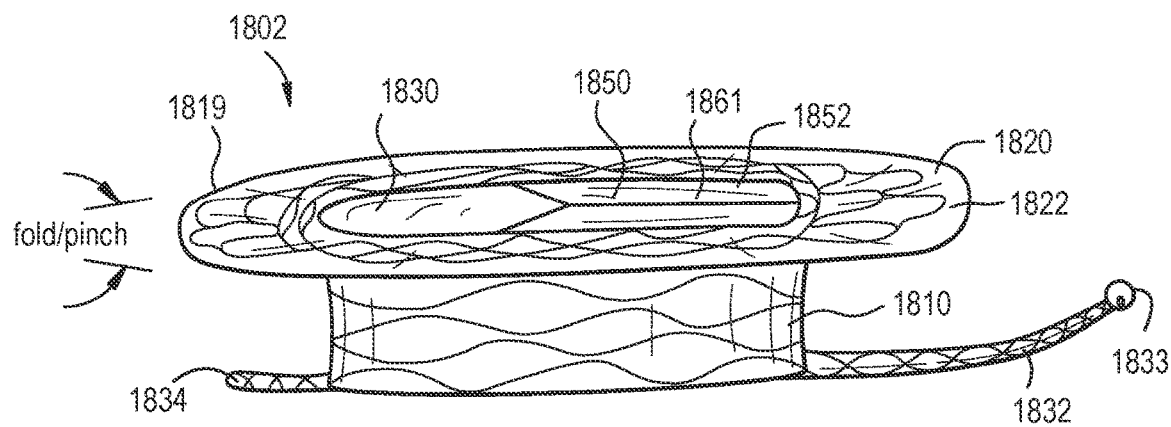
FIGS. 27A-27C illustrate various views of a process of placing a side deliverable transcatheter prosthetic heart valve in a compressed configuration and loading the compressed prosthetic valve in a delivery catheter, according to an embodiment.
Figure 27B:
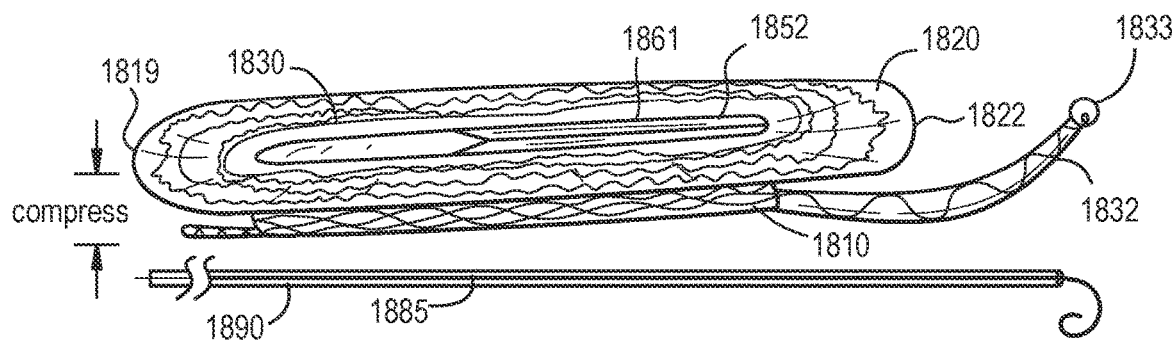
Figure 27C:
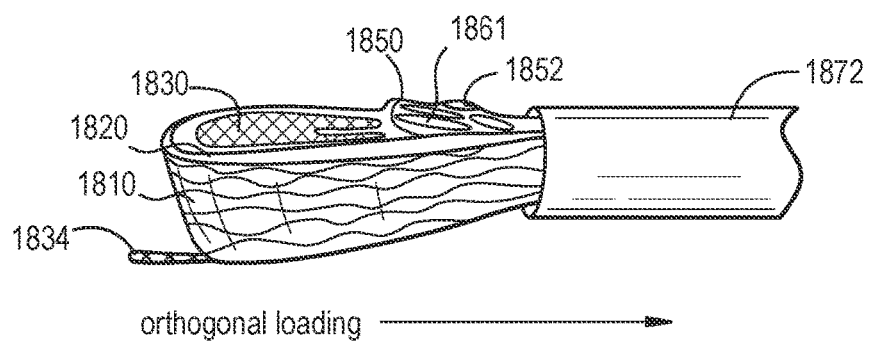

FIGS. 27A-27C illustrate a side-delivered transcatheter prosthetic heart valve 1802 according to an embodiment, and shown being transitioned to a compressed configuration and loaded into a delivery catheter 1872 for transcatheter delivery to a native annulus of a heart.

FIG. 27A shows the valve 1802 in a folded configuration along the z-axis (front to back when viewed from the broader side). FIG. 27A shows an outer frame 1810 with a flow control component 1850 and a spacer 1830 disposed within a central channel of the outer frame 1810. A distal anchoring element 1832 is shown extending from a distal side of the outer frame 1810 and a proximal anchoring element 1834 is shown extending from a proximal side of the outer frame 1810. A collar 1820 of the outer frame 1810 is shown folded/flattened at proximal and distal hinge points or fold areas 1819 and 1822. The flow control component 1850 is shown including leaflets 1861 that are mounted within a folded/flattened inner frame 1852.

FIG. 27B shows the valve 1802 in a vertically compressed configuration. For example, the valve 1802 is laterally folded (e.g., in the direction of the z-axis, at the hinge points and/or fold areas 1819 and 1822 of the outer frame 1810) and compressed vertically (e.g., in the direction of the y-axis). The flow control component 1850 and the spacer 1830 are also folded and compressed. The anterior anchoring element 1835 is shown vertically compressed in response to the vertical compression of the outer frame 1810. FIG. 27B also shows a guide wire 1885, which can be threaded through a guide wire coupler 1833 of the distal anchoring element 1832.

FIG. 27C shows the valve 1802 partially loaded into the delivery catheter 1872. The outer frame 1810, the folded collar 1820, the spacer 1830, and the flow control component 1850 having the leaflets 1861 and the inner frame 1852 are in and/or are being transitioned into a folded and compressed configuration.

Figure 28A:
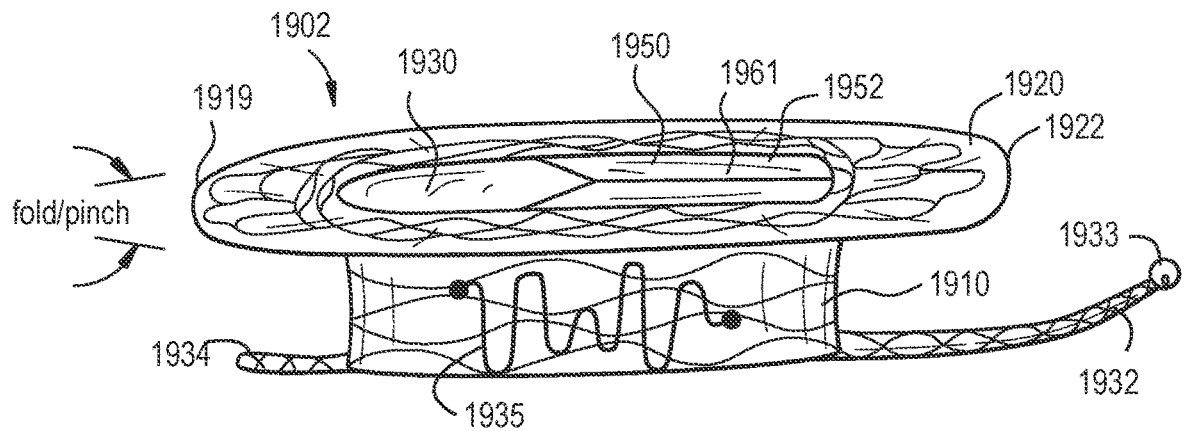
FIGS. 28A-28C illustrate various views of a process of placing a side deliverable transcatheter prosthetic heart valve in a compressed configuration and loading the compressed prosthetic valve in a delivery catheter, according to an embodiment.
Figure 28B:
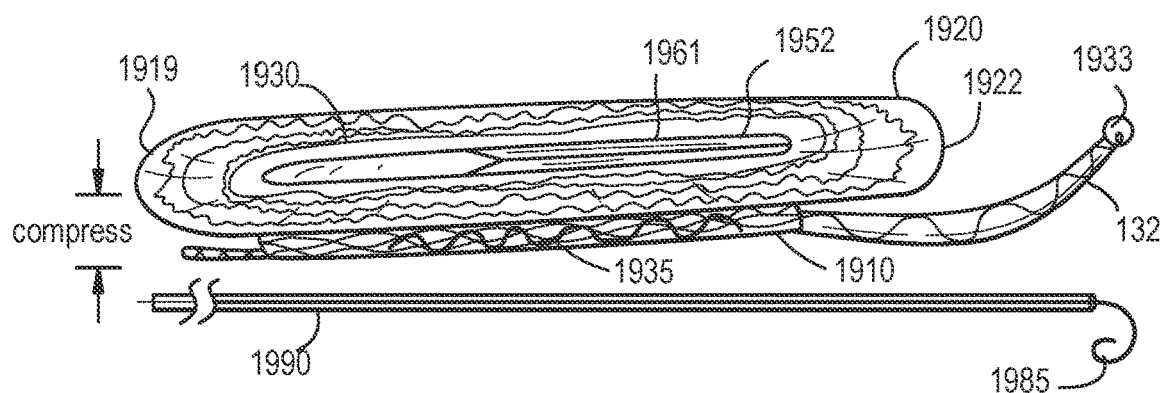
Figure 28C:
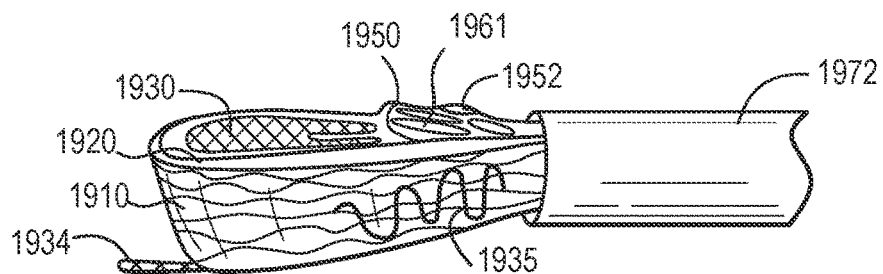

FIGS. 28A-28C illustrate a side-delivered transcatheter prosthetic heart valve 1902 according to an embodiment, and shown being transitioned to a compressed configuration and loaded into a delivery catheter 1972 for transcatheter delivery to a native annulus of a heart.

FIG. 28A shows the valve 1902 in a folded configuration along the z-axis (front to back when viewed from the broader side). FIG. 28A shows an outer frame 1910 with a flow control component 1950 and a spacer 1930 disposed within a central channel of the outer frame 1910. A distal anchoring element 1932 is shown extending from a distal side of the outer frame 1910 and a proximal anchoring element 1934 is shown extending from a proximal side of the outer frame 1910. An anterior anchoring element 1935 is shown mounted to an anterior side of the outer frame 1910. The anterior anchoring element 1935 is in a non-extended or unactuated configuration. A collar 1920 of the outer frame 1910 is shown folded/flattened at proximal and distal hinge points or fold areas 1919 and 1922. The flow control component 1950 is shown including leaflets 1961 that are mounted within a folded/flattened inner frame 1952.

FIG. 28B shows the valve 1902 in a vertically compressed configuration. For example, the valve 1902 is laterally folded (e.g., in the direction of the z-axis, at the hinge points and/or fold areas 1919 and 1922 of the outer frame 1910) and compressed vertically (e.g., in the direction of the y-axis). The flow control component 1950 and the spacer 1930 are also folded and compressed. The anterior anchoring element 1935 is shown vertically compressed in response to the vertical compression of the outer frame 1910. FIG. 28B also shows a guide wire 1985, which can be threaded through a guide wire coupler 1933 of the distal anchoring element 1932.

FIG. 28C shows the valve 1902 partially loaded into the delivery catheter 1972. The outer frame 1910 having the anterior anchoring element 1935, the folded collar 1920, the spacer 1930, and the flow control component 1950 having the leaflets 1961 and the inner frame 1952 are in and/or are being transitioned into a folded and compressed configuration.

Figure 29A:
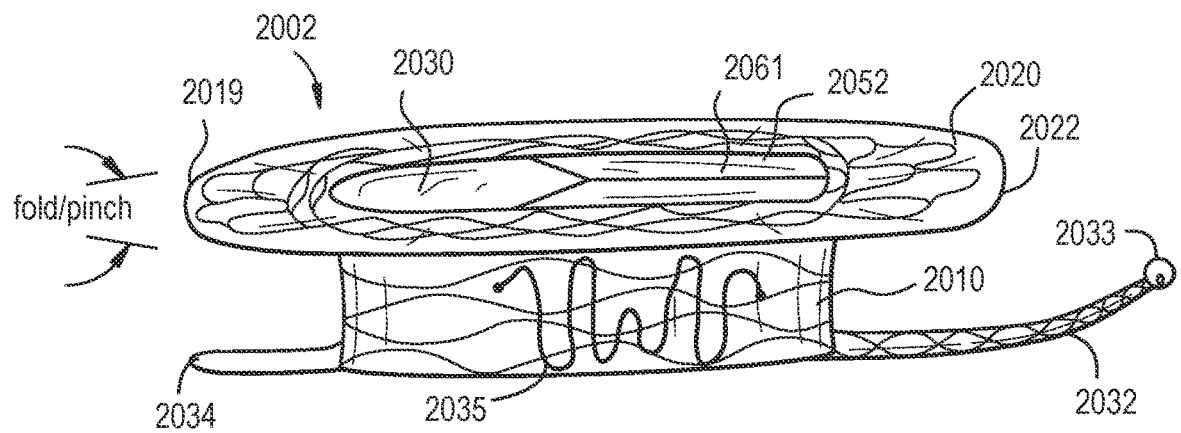
FIGS. 29A-29C illustrate various views of a process of placing a side deliverable transcatheter prosthetic heart valve in a compressed configuration and loading the compressed prosthetic valve in a delivery catheter, according to an embodiment.
Figure 29B:
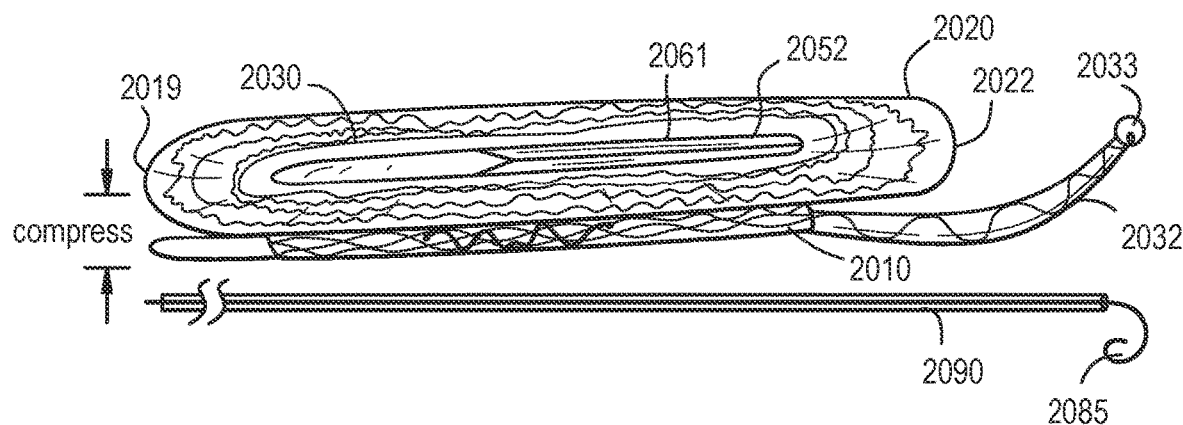
Figure 29C:
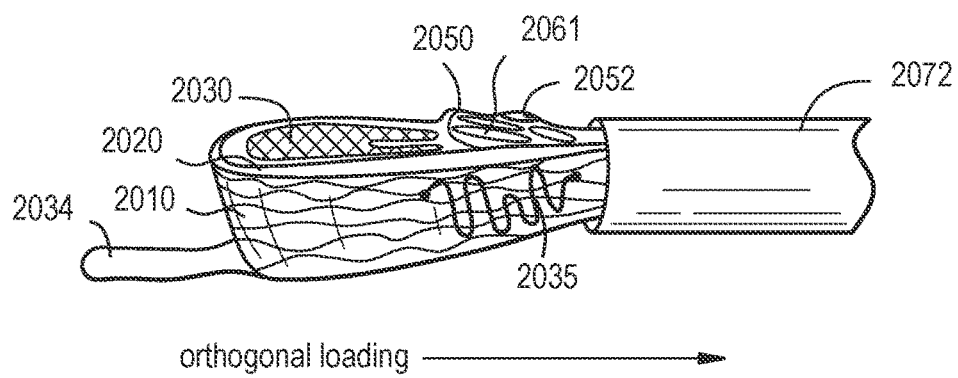

FIGS. 29A-29C illustrate a side-delivered transcatheter prosthetic heart valve 2002 according to an embodiment, and shown being transitioned to a compressed configuration and loaded into a delivery catheter 2072 for transcatheter delivery to a native annulus of a heart.

FIG. 29A shows the valve 2002 in a folded configuration along the z-axis (front to back when viewed from the broader side). FIG. 29A shows an outer frame 2010 with a flow control component 2050 and a spacer 2030 disposed within a central channel of the outer frame 2010. A distal anchoring element 2032 is shown extending from a distal side of the outer frame 2010 and a proximal anchoring element 2034 is shown extending from a proximal side of the outer frame 2010. An anterior anchoring element 2035 is shown mounted to an anterior side of the outer frame 2010. The anterior anchoring element 2035 is in a non-extended or unactuated configuration. A collar 2020 of the outer frame 2010 is shown folded/flattened at proximal and distal hinge points or fold areas 2019 and 2022. The flow control component 2050 is shown including leaflets 2061 that are mounted within a folded/flattened inner frame 2052.

FIG. 29B shows the valve 2002 in a vertically compressed configuration. For example, the valve 2002 is laterally folded (e.g., in the direction of the z-axis, at the hinge points and/or fold areas 2019 and 2022 of the outer frame 2010) and compressed vertically (e.g., in the direction of the y-axis). The flow control component 2050 and the spacer 2030 are also folded and compressed. The anterior anchoring element 2035 is shown vertically compressed in response to the vertical compression of the outer frame 2010. FIG. 29B also shows a guide wire 2085, which can be threaded through a guide wire coupler 2033 of the distal anchoring element 2032.

FIG. 29C shows the valve 2002 partially loaded into the delivery catheter 2072. The outer frame 2010 having the anterior anchoring element 2035, the folded collar 2020, the spacer 2030, and the flow control component 2050 having the leaflets 2061 and the inner frame 2052 are in and/or are being transitioned into a folded and compressed configuration.

Figure 30:
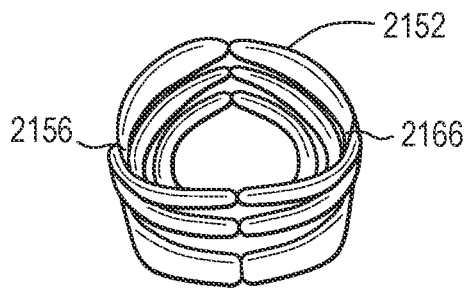
FIG. 30 is an illustration of a top perspective view of an inner frame of a flow control component included in a prosthetic valve according to an embodiment.

FIGS. 30-33 illustrate an inner leaflet frame 2152 of a flow control component according to an embodiment. FIG. 30 is an illustration of a top perspective view of the inner leaflet frame 2152. In some embodiments, the inner leaflet frame 2152 is formed of two separate wireframe sheets or members that are coupled at lateral connection points 2165 and 2166 (e.g., fold areas, elastically deformable regions, coupled edged portions, etc.). The inner leaflet frame 2152 is shown in an expanded or cylindrical configuration (e.g., prior to being folded and/or compressed).

Figure 31:
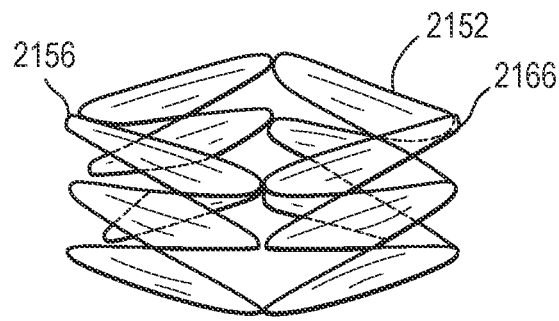
FIGS. 31-33 illustrate of various views of the inner frame of FIG. 30 and shown in a partially folded configuration, a folded configuration, and a folded and compressed configuration, respectively.
Figure 32:
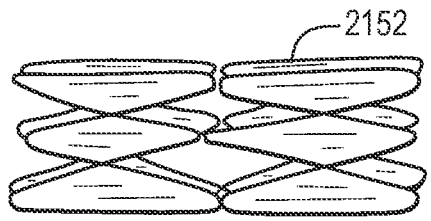

FIG. 31 shows the inner leaflet frame 2152 in a partially folded configuration. The inner leaflet frame 2152 is shown with wireframe sidewalls that allow for rotating or hinging at least at the lateral connection points 2165 and 2166. The inner leaflet frame 2152 can be configured to fold as shown in response to the valve being folded and/or compressed for delivery. FIG. 32 shows the inner leaflet frame 2152 in a completely folded configuration. The wireframe sidewalls have been rotated, hinged, and/or folded at their lateral connection points 2165 and 2166.

Figure 33:

FIG. 33 shows the inner leaflet frame 2152 in a folded and vertically compressed into a compressed configuration. The wireframe sidewalls can form cells (e.g., diamond-shaped cells or the like) that can be oriented in a direction of compression to allow for elastic compression of the inner frame 2152. In some embodiments, the inner frame 2152 can be vertically compressed into a pleated or accordion (compressed) configuration.

Figure 34:
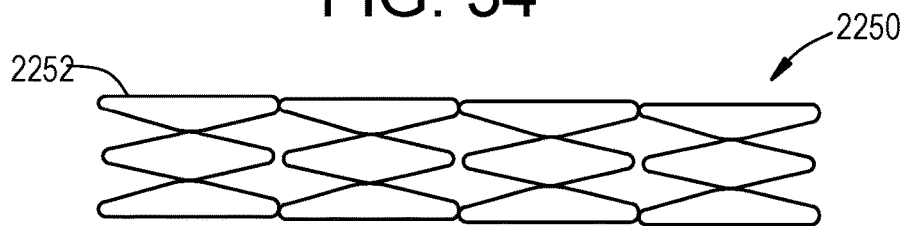
FIG. 34 is an illustration of a side view of an inner frame of a flow control component included in a prosthetic valve and shown as a linear wireframe sheet prior to being formed into a cylindrical configuration, according to an embodiment.
Figure 35:
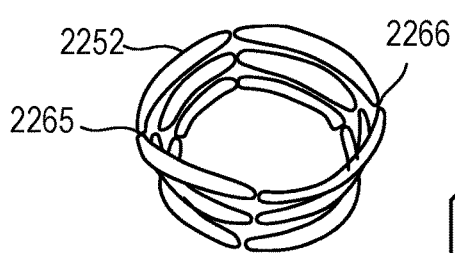
FIG. 35 is an illustration of a side perspective view of the inner frame of FIG. 34 and shown in the cylindrical configuration.

FIGS. 34-40 illustrate one or more portions of an inner flow control component 2250 according to an embodiment. FIG. 34 is an illustration of a side view of an inner leaflet frame 2252 of the flow control component. The inner leaflet frame 2252 is configured as and/or otherwise forms a linear wireframe sheet prior to being further assembled into a cylinder structure. FIG. 35 shows the inner leaflet frame 2252 in the cylinder structure or configuration (or a conical structure or configuration) with edge portions of the linear wireframe sheet being connected or coupled at lateral connection points 2265 and 2266 (e.g., hinge areas, fold areas, etc.). Moreover, the inner leaflet frame 2252 can be expanded (e.g., driven, formed, bent, etc.) from the linear sheet configuration into the cylinder structure or configuration.

Figure 36:
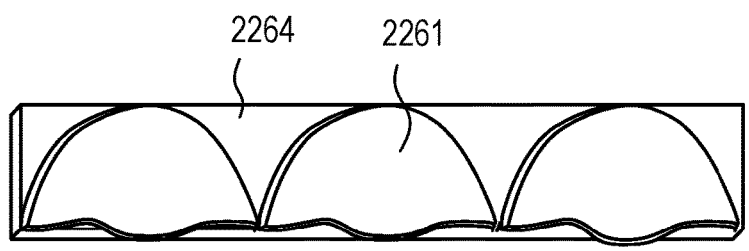
FIG. 36 is an illustration of a side view of a leaflet band of the inner flow control component having leaflet pockets sewn into a structural band of pericardial tissue and shown in a linear configuration.
Figure 37:
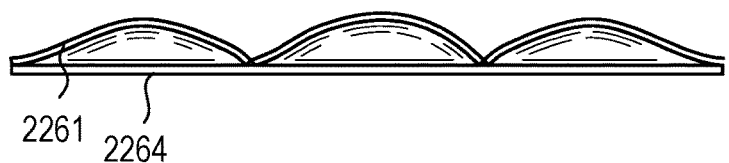
FIG. 37 is an illustration of a bottom view of the leaflet band of FIG. 36 and shown in the linear configuration.

FIGS. 36 and 37 are side view and a bottom view, respectively, illustrating a structural band 2264 of pericardial tissue with leaflet pockets 2261 sewn into the structural band 2264, before assembly into a cylindrical leaflet component and before mounting on and/or into the inner frame 2252 to form the collapsible (foldable, compressible) flow control component 2250.

Figure 38:
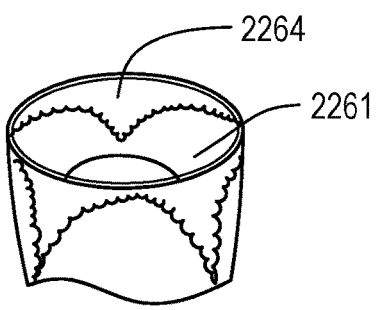
FIG. 38 is an illustration of a side perspective view of the leaflet band of FIGS. 36 and 37, and shown in a cylindrical configuration suitable for coupling to the inner frame of FIG. 35.

FIG. 38 is an illustration of a side perspective view of the structural band 2264 formed of pericardial tissue with the leaflet pockets 2261 sewn into the structural band 2264, after assembly into the cylindrical leaflet configuration, the leaflet pockets 2261 being disposed on an inner surface of the structural band 2264.

Figure 39:
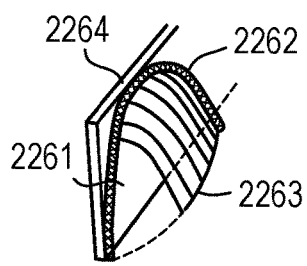
FIG. 39 is an illustration of a side perspective view of a portion of the leaflet band of FIG. 36 showing a single leaflet pocket sewn into the structural band.

FIG. 39 is an illustration of a side perspective view of part of the structural band 2264 of pericardial tissue showing a single leaflet pocket 2261 sewn into the structural band 2264. The leaflet pocket 2261 is shown with partial coaptation of the leaflet pocket 2261 to the structural band 2264 such that an open edge 2263 extends outward and a sewn edge 2262 forms a closed top parabolic edge providing attachment.

Figure 40:
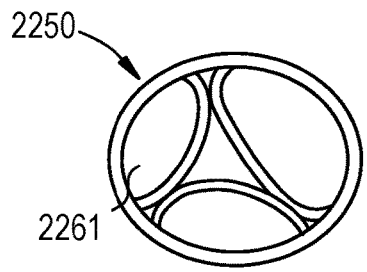
FIG. 40 is an illustration of a bottom view of the leaflet band of FIGS. 36-39 in the cylindrical configuration and showing partial coaptation of the leaflets to form a partially closed fluid-seal.

FIG. 40 is an illustration of a bottom view of the flow control component 2250. The cylindrical structural band 2264 and leaflet components 2261 are shown with partial coaptation towards forming a closed fluid-seal.

FIGS. 41A-41D illustrate various views showing a process of transitioning a side-deliverable transcatheter prosthetic heart valve and/or an outer frame thereof to a compressed configuration for delivery, according to an embodiment.

Figure 41A:
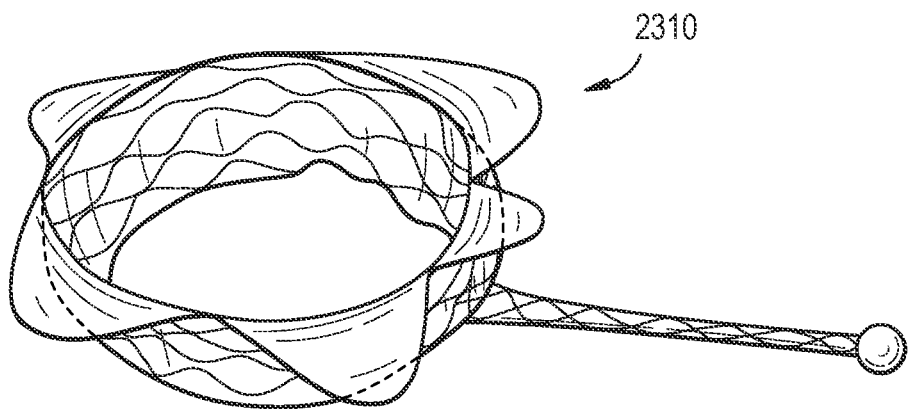
FIGS. 41A-41D illustrate various views showing a process of transitioning a side-deliverable transcatheter prosthetic heart valve to a compressed configuration for delivery, according to an embodiment.

FIG. 41A is an illustration of a top perspective view of an outer frame 2310 of the valve 2302 in a cylinder configuration, shown at the beginning of a process of folding and compression of the outer frame 2310. Although not shown in FIG. 41A, in some implementations, the outer frame 2310 can receive a flow control component 2350 within a central channel of the outer frame 2310 prior to the folding and compression (e.g., the outer frame 2310 and the flow control component are folded, compressed, and delivered together. In other implementations, the outer frame 2310 can be delivered independent of the flow control component. In such implementations, the flow control component can undergo a similar process of folding and compression and can be mounted in the outer frame 2310 after delivery (e.g., in the atrium of the heart).

Figure 41B:
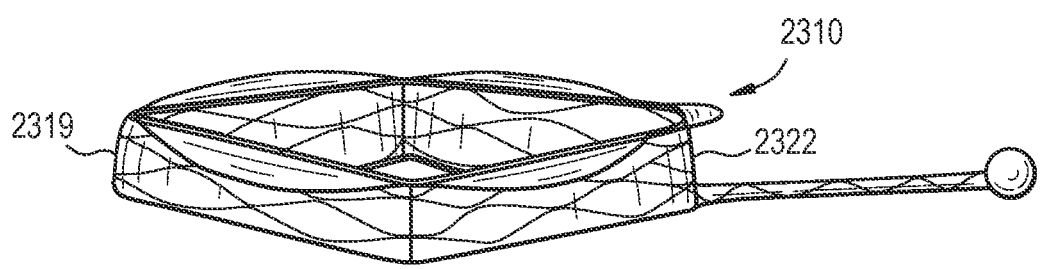
Figure 41C:
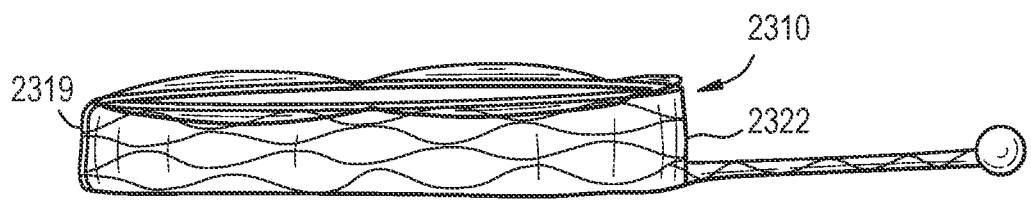
Figure 41D:
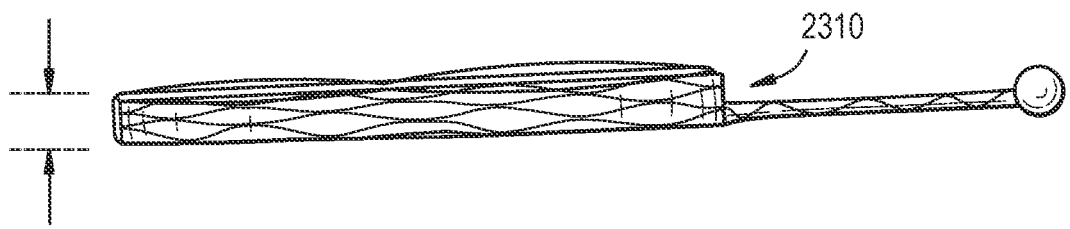

FIG. 41B is a top perspective view of the outer frame 2310 in a partially folded configuration with sidewalls of the outer frame 2310 rotating or hinging at lateral connection points or hinge points 2319 and 2322. FIG. 41C is a side view of the outer frame 2310 in a completely folded flat configuration with the frame sidewalls rotated or hinged at their lateral connection points or hinge portion 2319 and 2322. FIG. 41D is a side view of the outer frame 2310 in a folded and vertically compressed configuration with the frame sidewalls vertically compressed in a pleated or accordion configuration. In some implementations, the outer frame 2310 in the folded and compressed configuration can have a size that allows the outer frame 2310 to be delivered via a delivery catheter.

Figure 42A:
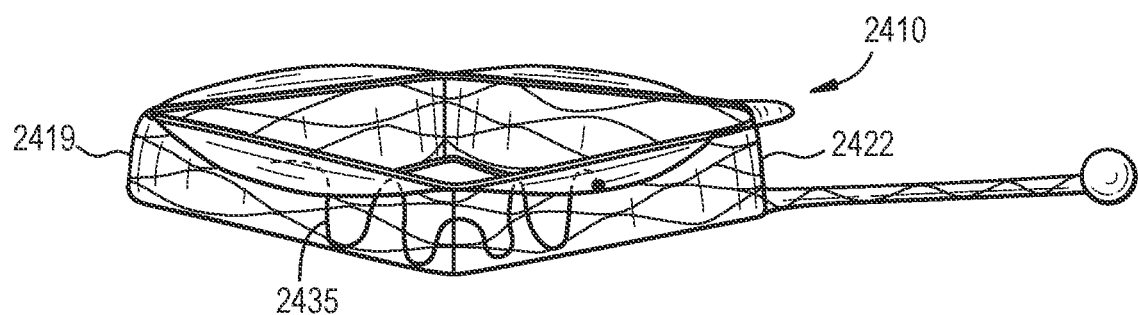
FIGS. 42A-42C illustrate various views showing a process of transitioning a side-deliverable transcatheter prosthetic heart valve to a compressed configuration for delivery, according to an embodiment.
Figure 42B:
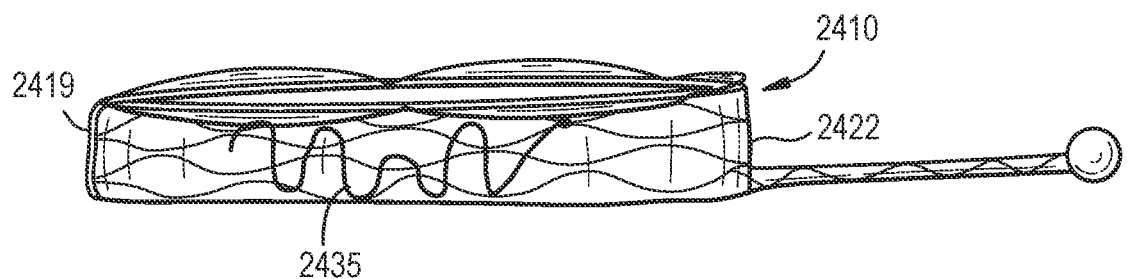
Figure 42C:
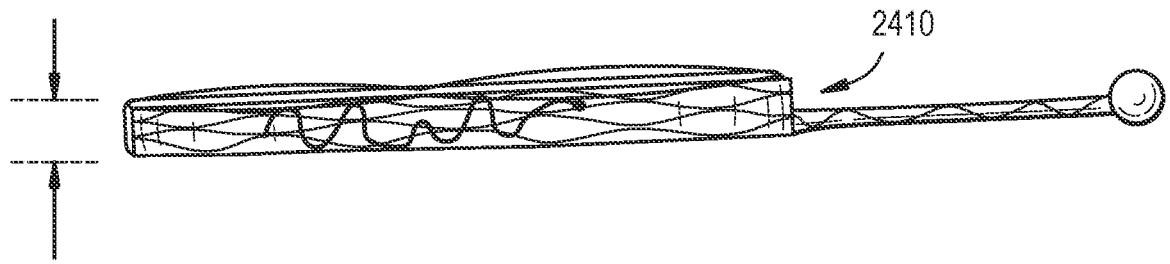

FIGS. 42A-42C illustrate various views showing a process of transitioning a side-deliverable transcatheter prosthetic heart valve and/or an outer frame thereof to a compressed configuration for delivery, according to an embodiment. FIG. 42A is a top perspective view of an outer frame 2410 of a valve in a partially folded configuration with sidewalls of the outer frame 2410 rotating or hinging at lateral connection points or hinge points 2419 and 2422. The outer frame 2410 includes at least an anterior anchoring element 2435 that can be configured to flex or bend as the outer frame 2410 is transitioned to the folded and compressed configuration. FIG. 42B is a side view of the outer frame 2410 in a completely folded flat configuration with the frame sidewalls rotated or hinged at their lateral connection points or hinge portion 2419 and 2422. FIG. 42C is a side view of the outer frame 2410 in a folded and vertically compressed configuration with the frame sidewalls vertically compressed in a pleated or accordion configuration. The anterior anchoring element 2435 is similarly vertically compressed when the outer frame 2410 is compressed. In some implementations, the outer frame 2410 in the folded and compressed configuration can have a size that allows the outer frame 2410 to be delivered via a delivery catheter.

Figure 43A:
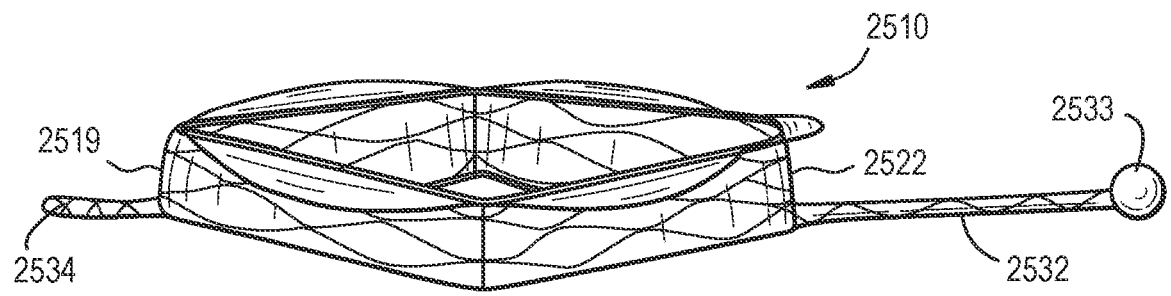
FIGS. 43A-43C illustrate various views showing a process of transitioning a side-deliverable transcatheter prosthetic heart valve to a compressed configuration for delivery, according to an embodiment.
Figure 43B:
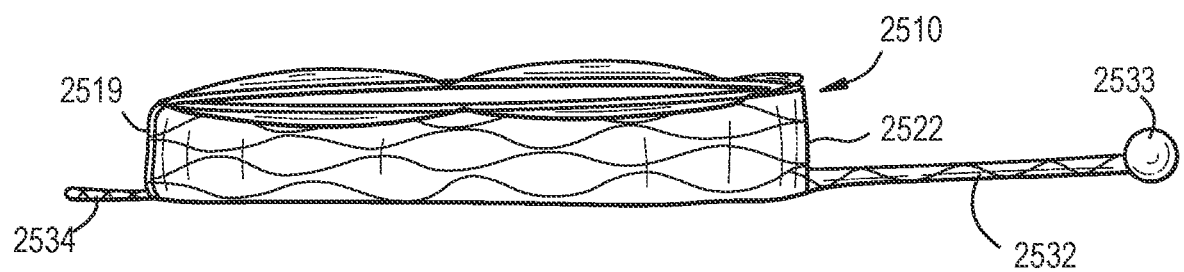
Figure 43C:
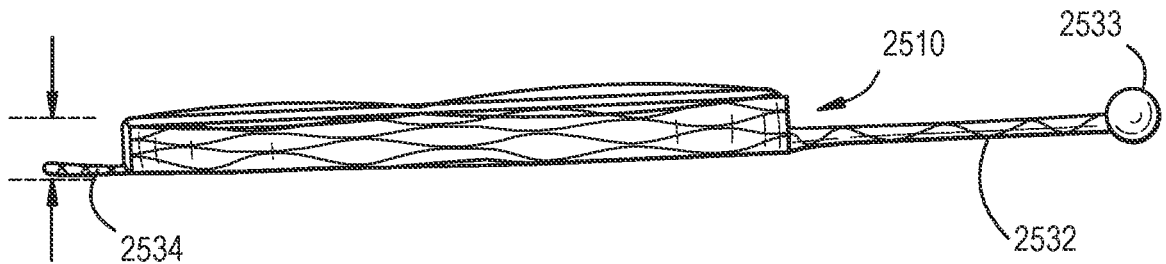

FIGS. 43A-43C illustrate various views showing a process of transitioning a side-deliverable transcatheter prosthetic heart valve and/or an outer frame thereof to a compressed configuration for delivery, according to an embodiment. FIG. 43A is a top perspective view of an outer frame 2510 of a valve in a partially folded configuration with sidewalls of the outer frame 2510 rotating or hinging at lateral connection points or hinge points 2519 and 2522. The outer frame 2510 includes at least a distal anchoring element 2532 and a proximal anchoring element 2534. The distal anchoring element 2532 includes a guide wire coupler 2533 that can receive and/or that can be disposed about a portion of a guide wire (not shown) to allow the outer frame 2510 to be advanced to a desired location in the body. FIG. 43B is a side view of the outer frame 2510 in a completely folded flat configuration with the frame sidewalls rotated or hinged at their lateral connection points or hinge portion 2519 and 2522. FIG. 43C is a side view of the outer frame 2510 in a folded and vertically compressed configuration with the frame sidewalls vertically compressed in a pleated or accordion configuration. In some implementations, the outer frame 2510 in the folded and compressed configuration can have a size that allows the outer frame 2510 to be delivered via a delivery catheter. The arrangement of the distal anchoring element 2532 and the proximal anchoring element 2534 can be such that the anchoring elements 2532 and 2534 extend substantially in a longitudinal direction (e.g., along the x-axis) and thus, can remain unfolded and/or uncompressed during delivery.

Figure 44A:
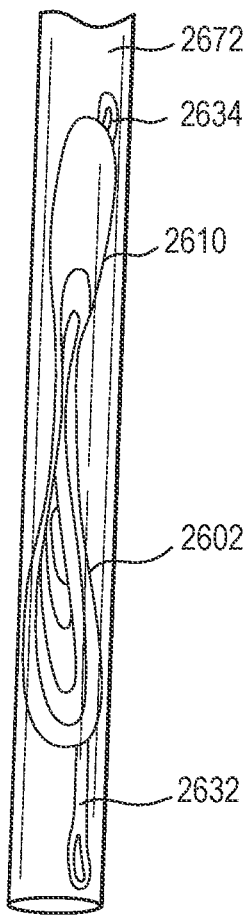
FIG. 44A is an illustration of a top view of a side deliverable transcatheter prosthetic heart valve in a compressed configured and disposed within a delivery catheter, according to an embodiment.
Figure 44B:
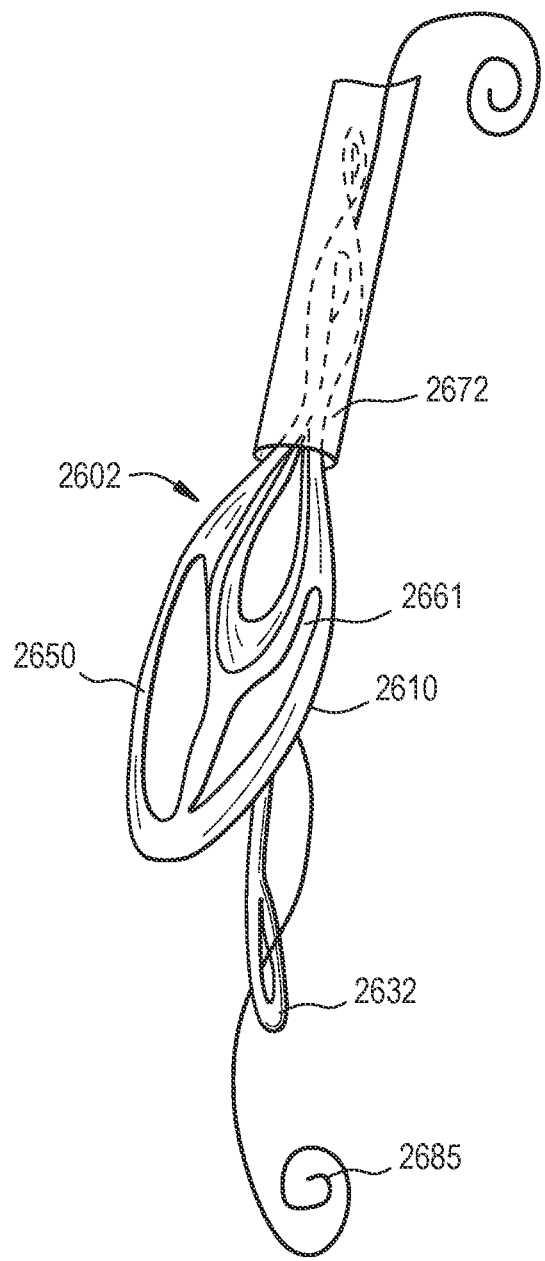
FIG. 44B is an illustration of a top perspective of the prosthetic heart valve of FIG. 44A partially released from the delivery catheter.

FIGS. 44A and 44B illustrate a valve 2602 according to an embodiment. FIG. 44A is an illustration of a top view of the valve 2602 shown in a compressed configuration and disposed (e.g., orthogonally loaded) within a delivery catheter 2672. The valve 2602 includes an outer frame 2610 having a distal anchoring element 2632 extending forward along an x-axis and a proximal anchoring element 2634 extending backwards or trailing along the x-axis. A flow control component 2650 is shown disposed within the outer frame 2610. FIG. 44B is an illustration of a top view of the valve 2602 partially released from the delivery catheter 2672. The distal anchoring element 2632 is shown leading the valve 2602 (along a guide wire 2685 to a deployment location. The flow control component 2650 is shown beginning to open and showing two of three leaflets 2661 opening from a folded, lie-flat configuration with the third leaflet opening from a folded configuration where it is folded back on itself when in the delivery catheter 2672.

Figure 45:
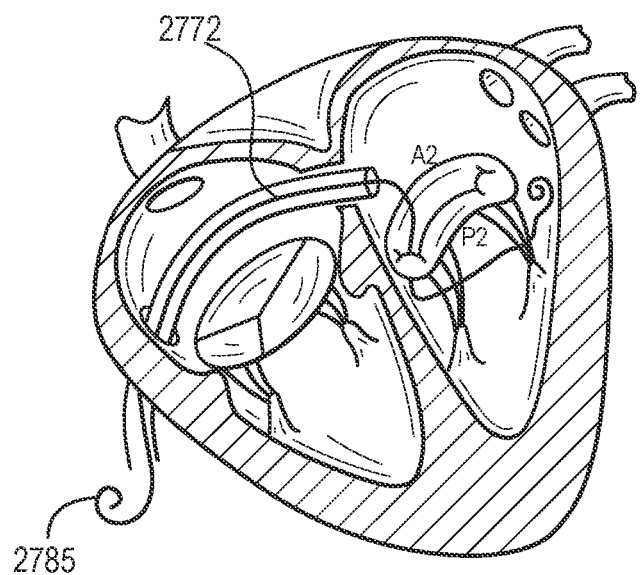
FIG. 45 is an illustration of a cut-away side view of a human heart with a trans-septal delivery catheter crossing from the right atrium to the left atrium for access to the mitral valve, according to an embodiment.
Figure 46:
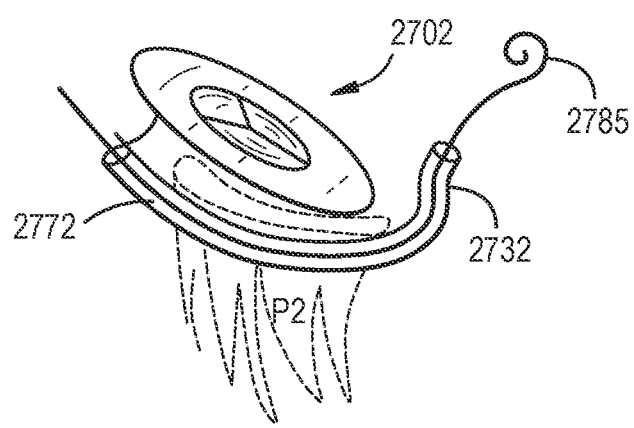
FIG. 46 is an illustration showing a process of using a distal anchoring element of a side deliverable transcatheter prosthetic heart valve to capture native tissue, according to an embodiment.

FIGS. 45 and 46 are illustrations showing a process of using a distal anchoring element of a side deliverable transcatheter prosthetic valve 2702 to capture native tissue, according to an embodiment. In some instances, the process can include the steps of (1) providing the foldable, compressible orthogonal prosthetic mitral valve 2702 (FIG. 26), (2) loading the valve 2702 sideways into a delivery catheter 2772, (3) and advancing the valve 2702 to the heart via the IVC or SVC over a pre-placed guide wire 2785 that is threaded onto a distal anchoring element 2732. The process then continues with (4) partially expelling a straightened end portion of the distal anchoring element 2732 of the valve 2702 from the delivery catheter 2772, (5) capturing, for example, a P2 leaflet and/or chordae by partially withdrawing the guide wire 2785 to contract or to allow the distal anchoring element 2732 to contract into a pre-curved, biased, or original configuration (FIG. 46), (6) partially expelling the valve 2702 to allow a set of prosthetic leaflets to begin functioning and check for perivalvular leaks (PVLs), (7) positioning valve 2702 in the annulus of the native valve, and (8) completing deployment of the valve 2702 into the native annulus.

Figure 47:
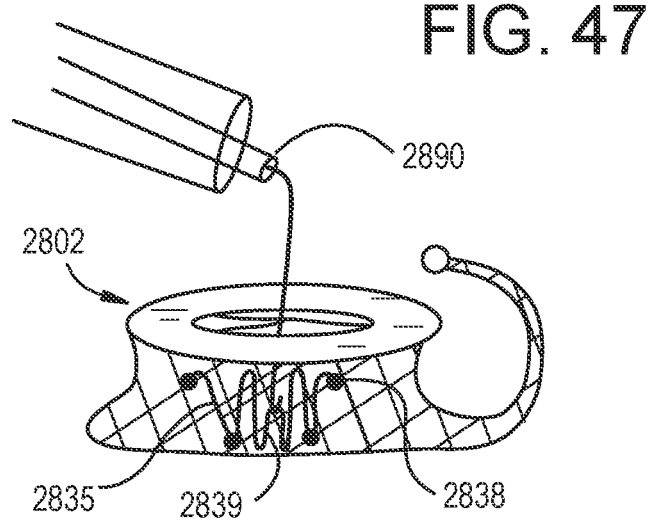
FIGS. 47-49 illustrate a side perspective views of a process of deploying a side deliverable transcatheter prosthetic heart valve, according to an embodiment.
Figure 48:
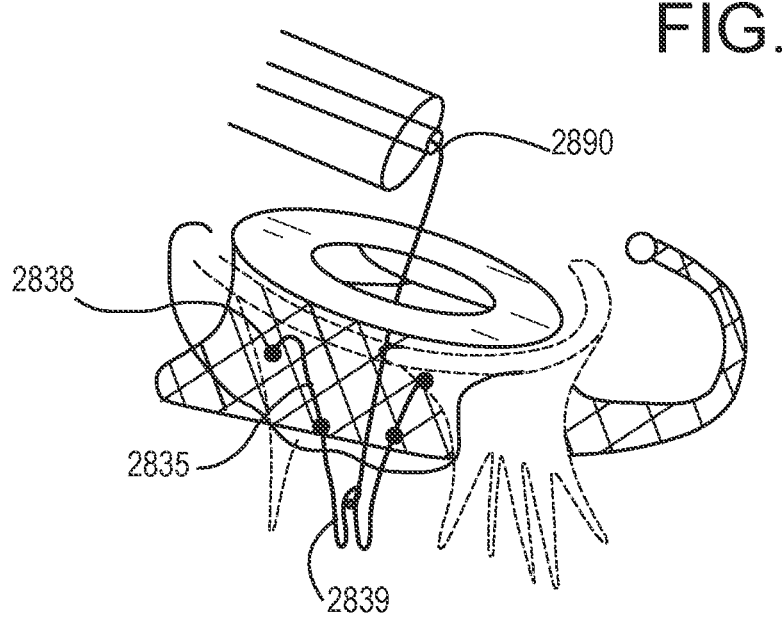
Figure 49:
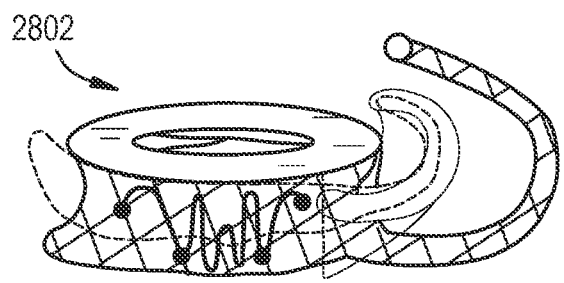

FIGS. 47-49 are side perspective views of a side deliverable transcatheter prosthetic heart valve 2802, according to an embodiment, and illustrating a process of deployment. FIG. 47 shows the valve 2802 having an anterior anchoring element 2835 in a folded, compressed, and/or unactuated position. The anterior anchoring element 2835 is mounted to an anterior side of the valve 2802 (or an outer frame thereof) via any number of attachment points 2838. A positioning tool 2890 (e.g., a steerable catheter/guidewire) is shown deploying an engagement portion 2939 of the anterior anchoring element 2835.

FIG. 48 shows the positioning tool 2890 placing the engagement portion 2839 of the anterior anchoring element 2835 into an extended position to engage and/or capture leaflet tissue. The attachment points 2838 secure a portion of the anterior anchoring element 2835 so that when the engagement portion 2839 is extended, it generates a spring-back force to capture the tissue caught between the engagement portion 2839 and a portion of an outer frame of the valve 2802. FIG. 49 shows the anterior anchoring element 2835 returned to the folded and/or compressed configuration with a portion of anterior leaflet tissue and/or chordae disposed between the engagement portion 2839 and the outer frame.

Figure 50A:
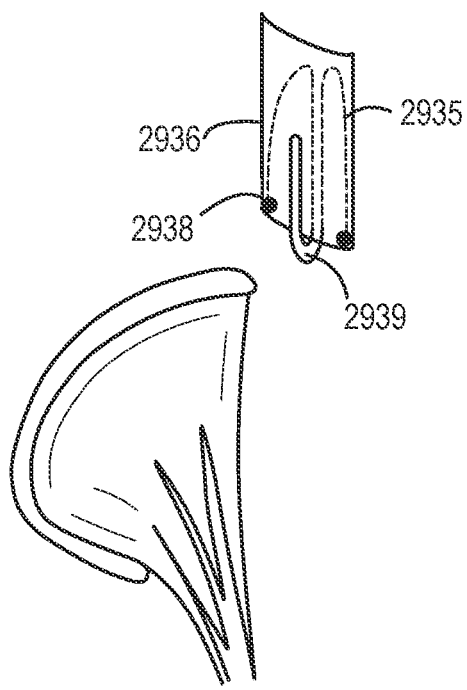
FIGS. 50A-50D illustrate various views of an anterior anchor element included in a side deliverable transcatheter prosthetic heart valve according to an embodiment, and shown in a first configuration, a second configuration, a third configuration, and a fourth configuration, respectively.
Figure 50B:
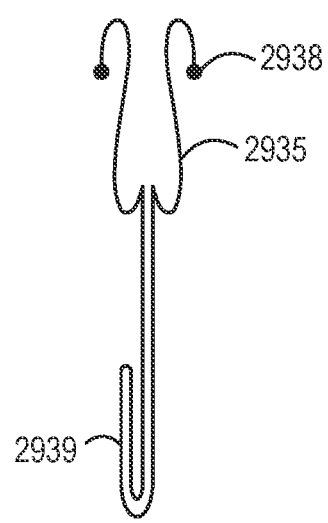
Figure 50C:
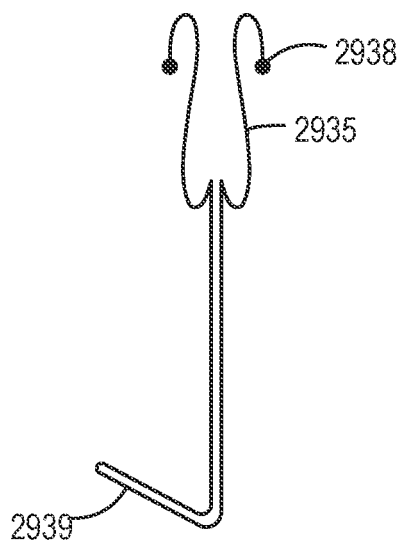
Figure 50D:
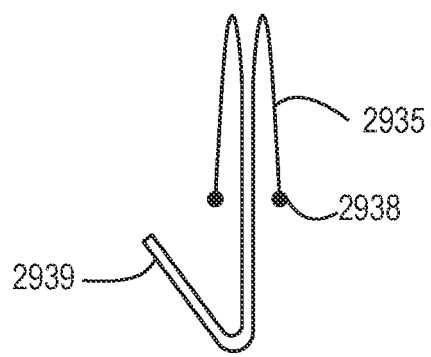

FIGS. 50A-50D illustrate various views of an anterior anchor element 2935 included in a side deliverable transcatheter prosthetic heart valve according to an embodiment, and shown in a first configuration, a second configuration, a third configuration, and a fourth configuration, respectively. FIG. 50A shows the anterior anchoring element 2935 having an engagement portion 2939, and being at least partially stowed in a sleeve 2936 before deployment. Attachment points 2938 are shown adjacent the engagement portion 2939 and are configured to mount the anterior anchoring element 2935 to an outer frame of the valve and/or to the sleeve 2936, which in turn is mounted to the outer frame. FIG. 50B shows the anterior anchoring element 2935 extended in a ventricular direction along the central (y) axis. The attachment points 2938 are positioned above the engagement portion 2939 of the anterior anchoring element 2935. The engagement portion 2939 is shown folded and/or non-extended in a subannular position. FIG. 50C shows the anterior anchoring element 2935 completely unfolded for capturing anterior tissue. The attachment point 2938 are positioned above the engagement portion 2939 of the anterior anchoring element 2935. The engagement portion 2939 is shown unfolded and extended in a subannular position to capture native tissue. FIG. 50D shows the anterior anchoring element 2935 in a folded and/or retracted position after capture of tissue where the tissue (not shown) is pinned against a perimeter wall of the outer frame. In the retracted position, the attachment points 2938 are positioned relatively adjacent the engagement portion 2939 of the anterior anchoring element 2935. The engagement portion 2939 is shown in a partially unfolded and/or partially extended configuration (e.g., a capturing configuration).

Figure 51A:
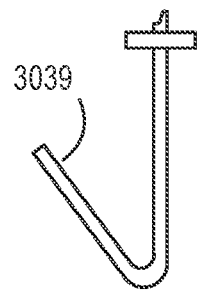
FIGS. 51A-51G illustrate side perspective views of various anchors for anchoring a portion of a side deliverable transcatheter prosthetic heart valve to native tissue, each according to a different embodiment.
Figure 51B:
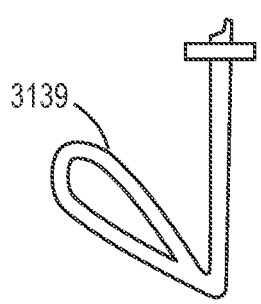
Figure 51C:
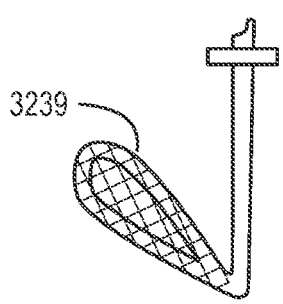
Figure 51D:
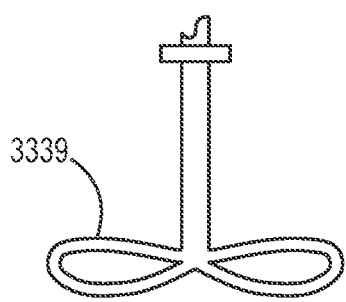
Figure 51E:
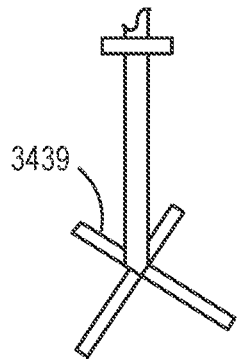
Figure 51F:
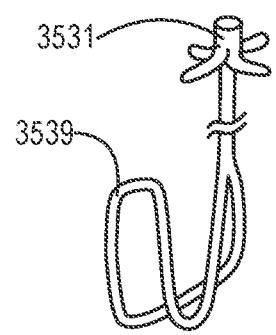
Figure 51G:
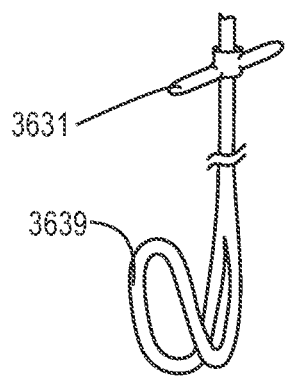

FIGS. 51A-51G illustrate side perspective views of various anchors and/or anchor loop configurations for anchoring a portion of a side deliverable transcatheter prosthetic heart valve to native tissue, each according to a different embodiment. The anchors and/or anchor loop configurations can be included in, for example, an anterior anchoring element and/or any other suitable anchoring element of a prosthetic valve. For example, FIG. 51A shows a post-type hook 3039; FIG. 51B shows a loop-type hook 3139; FIG. 51C shows a paddle-type hook 3239; FIG. 51D shows a double loop-type hook 3339; FIG. 51E shows a footer-type hook 3439; FIG. 51F shows a bent loop-type hook 3539 with an optional locking nut 3531; and FIG. 51G shows a bent loop-type hook 3639 with an optional locking nut 3631.

Figure 52:
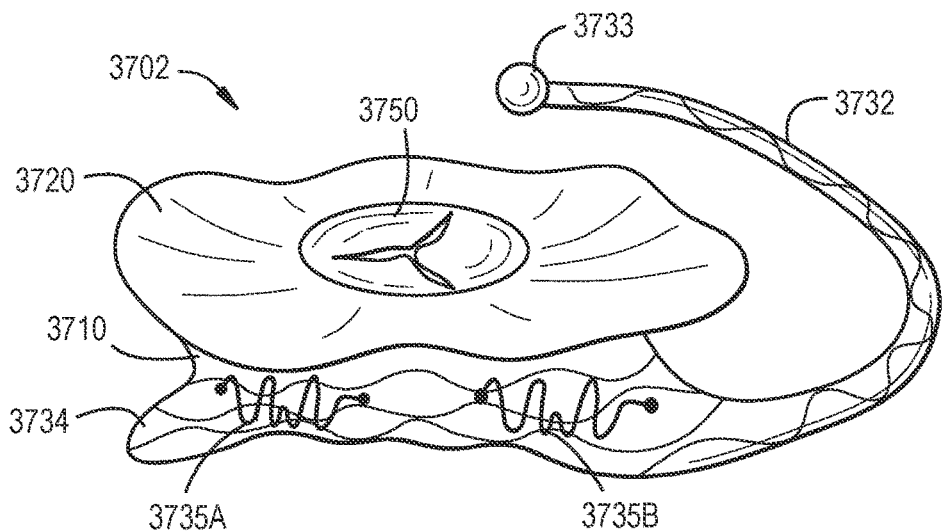
FIG. 52 is an illustration of a side perspective view of a side deliverable transcatheter prosthetic heart valve having multiple anterior anchor elements, according to an embodiment.
Figure 53:
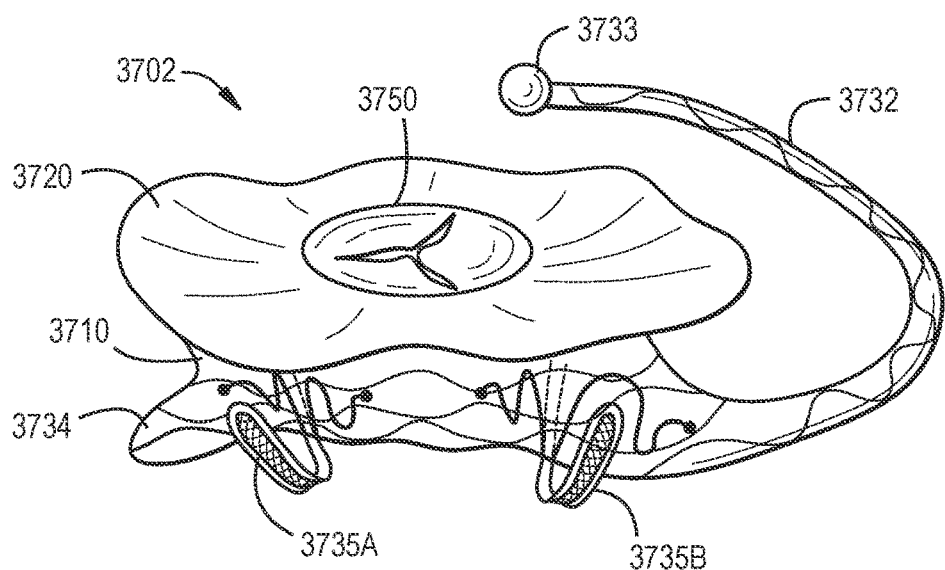
FIG. 53 is an illustration of a side perspective view of a side deliverable transcatheter prosthetic heart valve having multiple anterior anchor elements, according to an embodiment.

FIGS. 52 and 53 are side perspective views of a side deliverable transcatheter prosthetic heart valve 3702 having a distal anchoring element 3732, a proximal anchoring element 3732, and multiple anterior anchor elements 3735A and 3735B, according to an embodiment. The valve 3702 has an outer frame 3710 with an atrial collar 3720 and a flow control component 3750 mounted within a central channel of the outer frame 3710. The distal anchoring element 3732 extends from a distal side of the outer frame 3710 and includes a guide wire coupler 3733 that can receive and/or can be threaded on a guide wire for delivering the valve 3702 to a desired location. The distal anchoring element 3732 can provide subannular anchoring on a distal side of the annulus and can, in some implementations, wrap around the posterior aspect or portion of the native valve. The proximal anchoring element 3734 extends from a proximal side of the outer frame 3710 and provides subannular anchoring on a proximal side of the annulus. The valve 3702 includes two anterior anchoring elements 3735A and 3735B mounted to an anterior side of the outer frame 3710. FIG. 52 shows the two anterior anchoring element 3735A and 3735B in a folded, non-extended, and/or non-actuated configuration. FIG. 53 shows the two anterior anchoring elements 3735A and 3735B in an extended configuration to engage and/or capture anterior native tissue and/or chordae. The anterior anchoring elements 3735A and 3735B can be retracted from the extended configuration to secure and/or pin the native tissue and/or chordae against the outer frame 3710.

Figure 54:
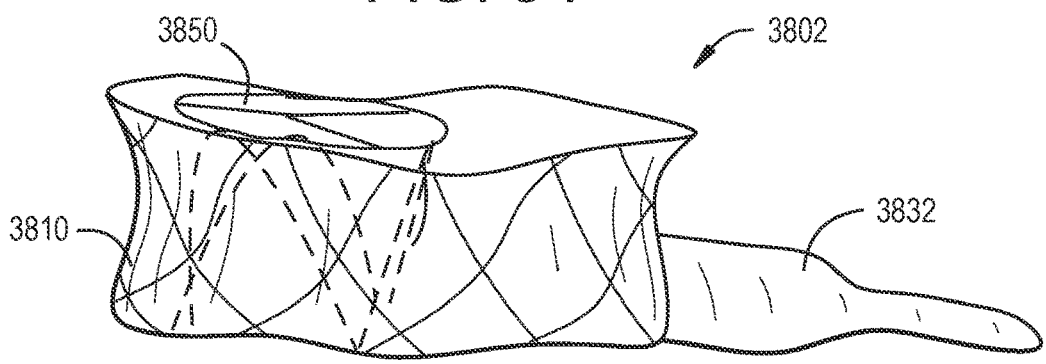
FIG. 54 is an illustration of a side perspective view of a side deliverable transcatheter prosthetic heart valve having a distal anchoring element with a graduated stiffness, according to an embodiment.

FIG. 54 is a side view of a side deliverable transcatheter prosthetic heart valve 3802, according to an embodiment. The valve 3802 includes, for example, a graduated stiffness distal anchoring element 3832 having a softer rigidity in a position or section near or adjacent an outer frame 3810 of the valve 3802, and a stiffer rigidity in a portion or section away from the outer frame 3810. The valve 3802 is shown with an offset flow control component 3850. While the valve 3802 is shown with a distal anchoring element 3832 having the graduated stiffness, in other embodiments, a valve 3802 can include the distal anchoring element 3832 having the graduated stiffness and/or a proximal anchoring element having a similar or different graduated stiffness.

Figure 55A:
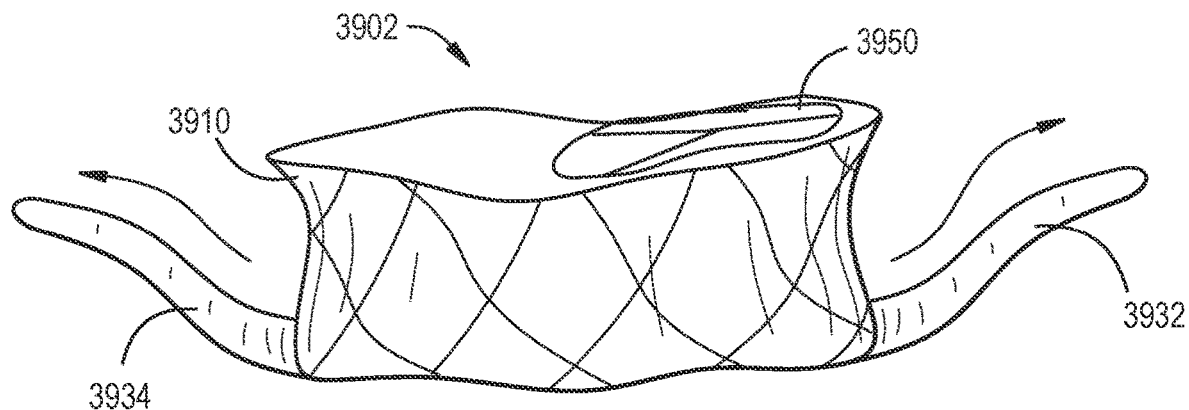
FIG. 55A is an illustration of a side perspective view of a side deliverable transcatheter prosthetic heart valve having a distal anchoring element and a proximal anchoring element, according to an embodiment.
Figure 55B:
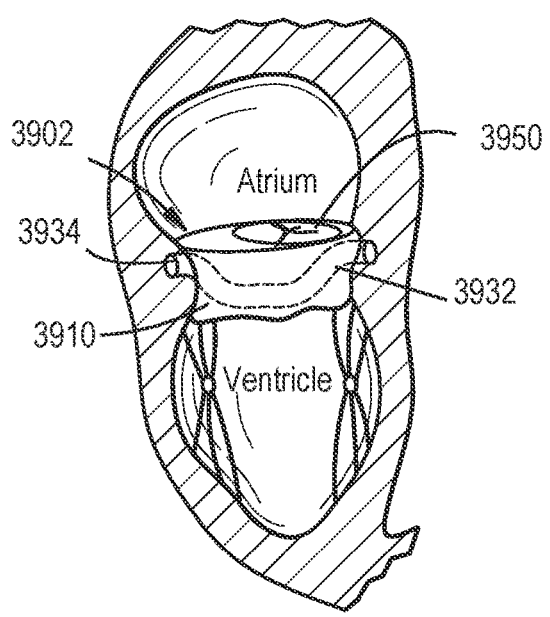
FIG. 55B is an illustration of a side perspective view of the prosthetic heart valve of FIG. 55A deployed in an annulus of a native valve.

FIG. 55A is a side view of a side deliverable transcatheter prosthetic heart valve 3802, according to an embodiment. The valve 3902 includes an outer frame 3910 having a distal anchoring element 3932 extending from a distal side of the outer frame 3910 and a proximal anchoring element 3934 extending from a proximal side of the outer frame 3910. A flow control component 3950 is shown mounted in an offset position within a central channel of the outer frame 3910. The anchoring elements 3932 and 3934 are, for example, a single-piece structure that wraps around the outer frame 3910 of the valve 3902. FIG. 55B is a cut-away side view of a heart showing the valve 3902 deployed in an annulus of a native valve. The anchoring elements 3932 and 3934 act in concert to provide, for example, an anchoring force on the valve 3902 in a downward direction.

Figure 56A:
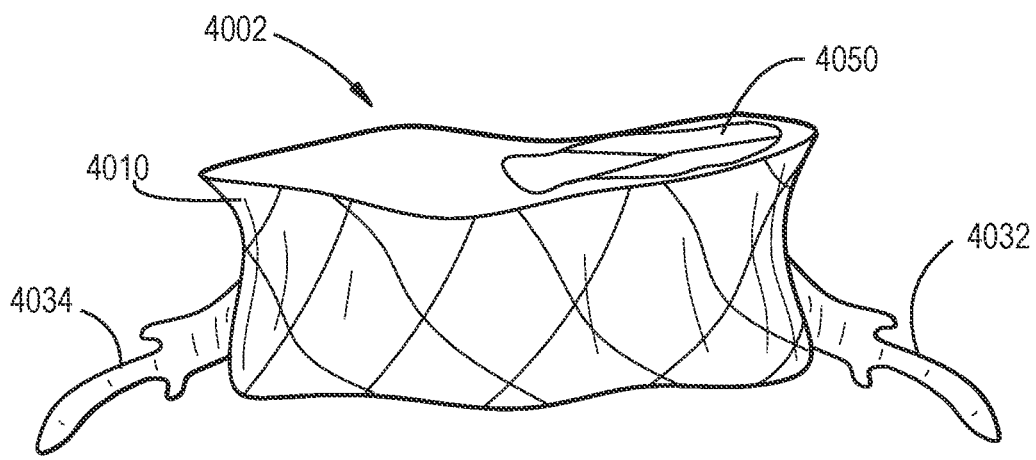
FIG. 56A is an illustration of a side perspective view of a side deliverable transcatheter prosthetic heart valve having a distal anchoring element and a proximal anchoring element, according to an embodiment.
Figure 56B:
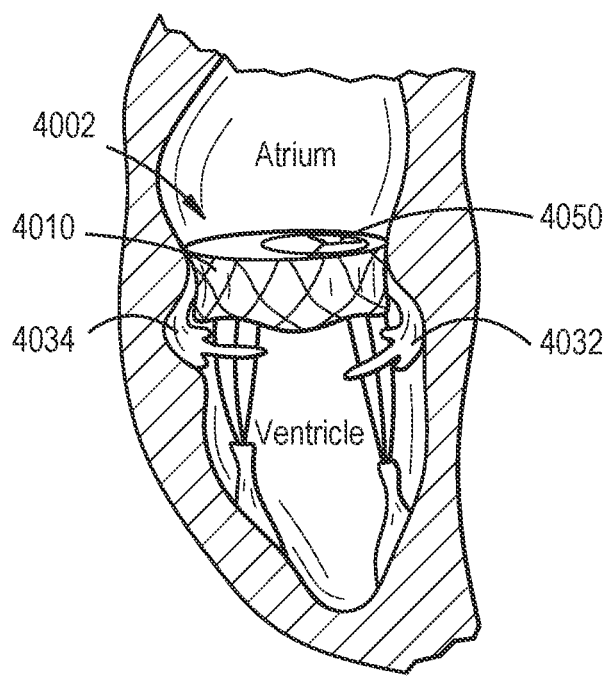
FIG. 56B is an illustration of a side perspective view of the prosthetic heart valve of FIG. 56A deployed in an annulus of a native valve.

FIG. 56A is a side view of a side deliverable transcatheter prosthetic heart valve 3802, according to an embodiment. The valve 4002 includes an outer frame 4010 having a distal anchoring element 4032 extending from a distal side of the outer frame 4010 and a proximal anchoring element 4034 extending from a proximal side of the outer frame 4010. A flow control component 4050 is shown mounted in an offset position within a central channel of the outer frame 4010. The anchoring elements 4032 and 4034 are, for example, independent elements that each wrap around a portion of the outer frame 4010 and include portions or fingers that can engage native tissue. FIG. 56B is a cut-away side view of a heart showing the valve 4002 deployed in an annulus of a native valve. The anchoring elements 4032 and 4034 are shown having portions or fingers that wrap around native tissue such as, for example, the chordae. In some implementations, the anchoring elements 4032 and 4034 can become entangled in the native chordae to promote in-growth and secure anchoring.

Figure 57A:
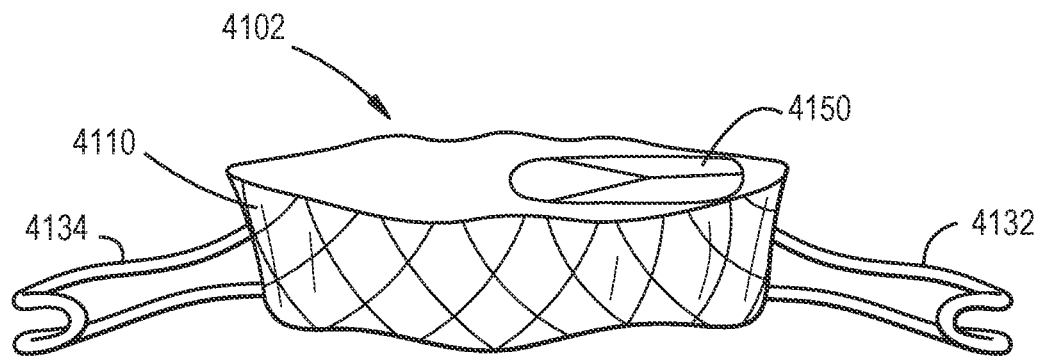
FIG. 57A is an illustration of a side perspective view of a side deliverable transcatheter prosthetic heart valve having a distal anchoring element and a proximal anchoring element, according to an embodiment.
Figure 57B:
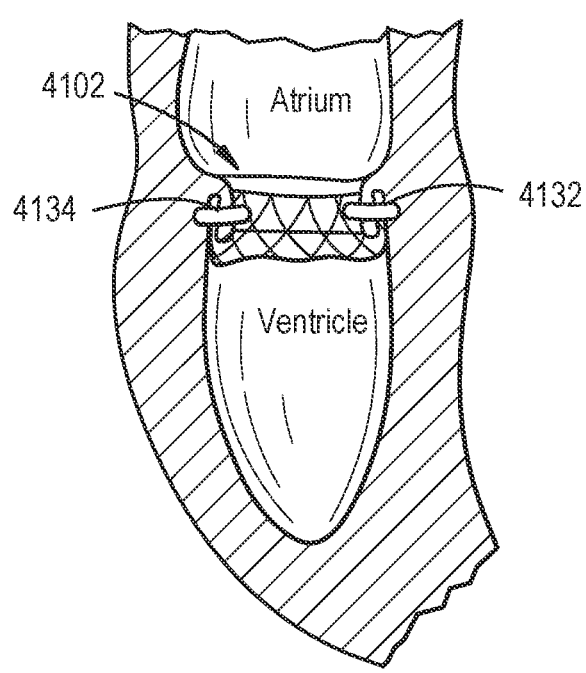
FIG. 57B is an illustration of a side perspective view of the prosthetic heart valve of FIG. 57A deployed in an annulus of a native valve.

FIG. 57A is a side view of a side deliverable transcatheter prosthetic heart valve 3802, according to an embodiment. The valve 4102 includes an outer frame 4110 having a distal anchoring element 4132 extending from a distal side of the outer frame 4110 and a proximal anchoring element 4134 extending from a proximal side of the outer frame 4110. A flow control component 4150 is shown mounted in an offset position within a central channel of the outer frame 4110. The anchoring elements 4132 and 4134 are, for example, independent elements that each wrap around a portion of the outer frame 4110 and include curved-loop portions and/or ends that can engage native tissue. FIG. 57B is a cut-away side view of a heart showing the valve 4102 deployed in an annulus of a native valve. The anchoring elements 4132 and 4134 are shown having the curved-loop portions or ends wrap around native tissue such as, for example, the chordae to promote in-growth and secure anchoring.

Figure 58A:
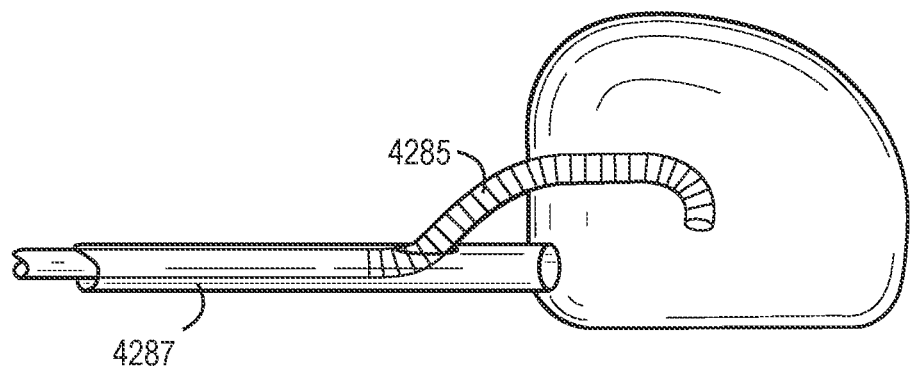
FIG. 58A is an illustration of a guide wire delivery catheter providing access to, for example, an A1-P1 target area of a native valve, according to an embodiment.
Figure 58B:
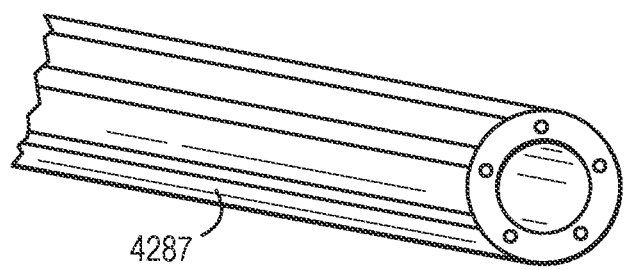
FIG. 58B is an illustration of an enlarged view of a portion of the guide wire delivery catheter of FIG. 58A.

FIG. 58A is an illustration of a guide wire delivery catheter 4287 providing access to, for example, an A1-P1 target area of a native valve, according to an embodiment. A guide wire 4285 can extend out of a side port of the guide wire delivery catheter 4287 and can provide a path for positioning a valve in a desired location (e.g., the A1-P1 target location). FIG. 58B is an illustration of an enlarged view of a portion of the guide wire delivery catheter 4287.

Figure 59:
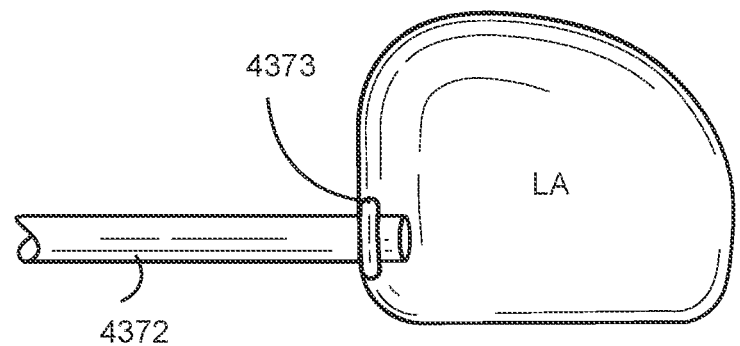
FIG. 59 is an illustration of a circumferential balloon disposed around an end portion of a delivery catheter, according to an embodiment.

FIG. 59 is an illustration of a delivery catheter 4372 providing access to, for example, an atrium of a heart, according to an embodiment. The delivery catheter 4372 can be, for example, a 28 Fr delivery catheter with an end portion (e.g., an atrially exposed end portion) disposed in the atrium. A circumferential balloon 4373 is shown inflated around the atrial exposed end portion of the delivery catheter 4372 to temporarily secure the delivery catheter 4372 to the atrial wall.

Figure 60:
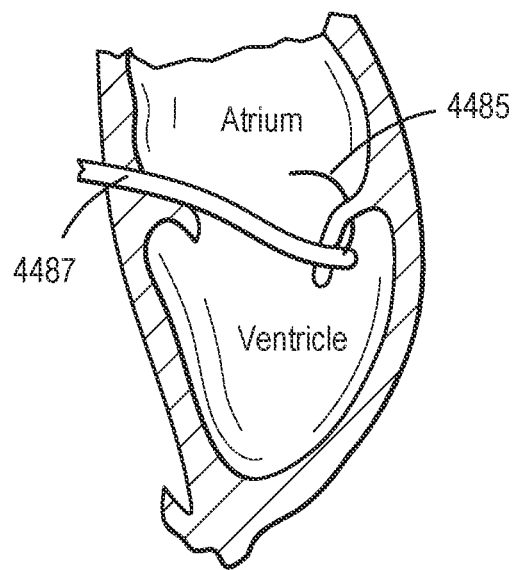
FIG. 60 is an illustration of a side view of a distal end portion of a sheath included in a delivery system and having a side port for delivering a guide wire to, for example, an A1-P1 target area of a native valve, according to an embodiment.
Figure 61:
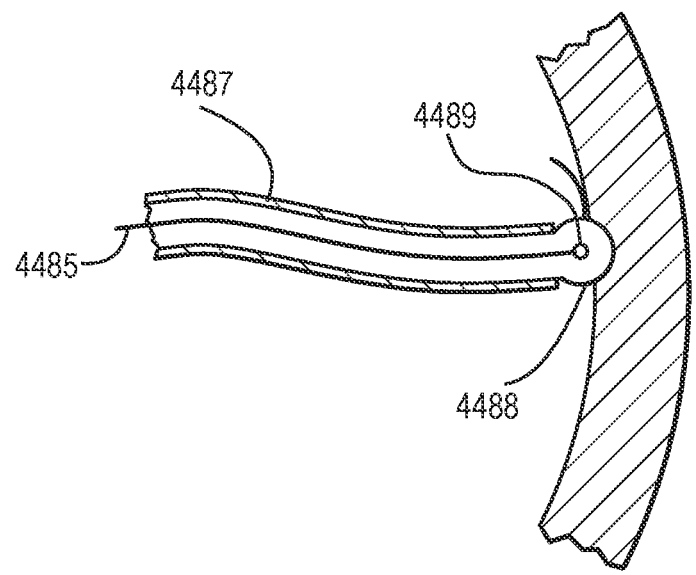
FIG. 61 is an illustration of a cross-sectional view of the sheath of FIG. 60 engaging native tissue and allowing the side port to deliver the guide wire.

FIG. 60 is a cut-away side view of a portion of a heart showing a guide wire delivery catheter 4487 extending into a volume of the heart, according to an embodiment. The guide wire delivery catheter 4487 is shown extending through the native annulus and into the left ventricle. A guide wire 4485 is shown extending from the guide wire delivery catheter 4487 to a target A1-P1 area. FIG. 61 is an enlarged cross-sectional view of the guide wire delivery catheter 4487. The guide wire delivery catheter 4487 is shown with an atraumatic closed end 448 that defines and/or includes a side port 4489 to allow the guide wire 4485 to extend out of a distal end portion of the guide wire delivery catheter 4487 without causing trauma to the native tissue.

Figure 62:
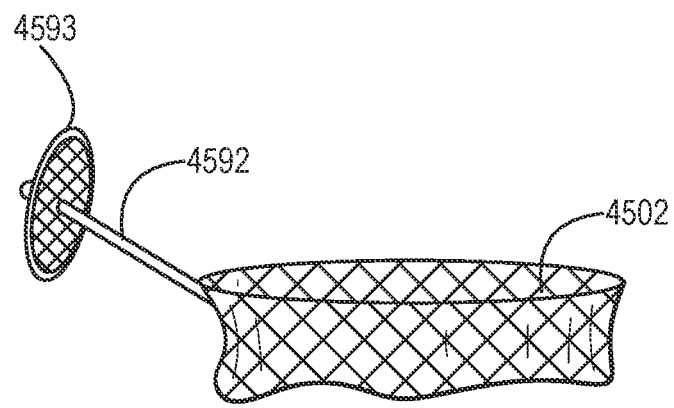
FIG. 62 is an illustration of a side perspective view of a side deliverable transcatheter prosthetic heart valve having a septal tether configured to secure the prosthetic heart valve in an annulus of a native valve, according to an embodiment.
Figure 63:
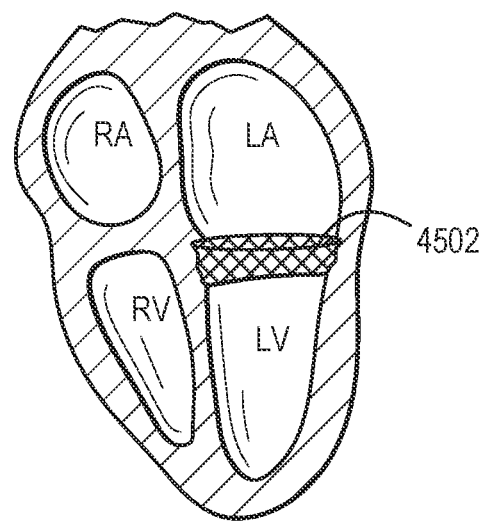
FIG. 63 is an illustration of a cross-sectional view of a side deliverable transcatheter prosthetic heart valve and secured in an annulus of a native valve, according to an embodiment.

FIG. 62 is a perspective side view of a side deliverable transcatheter prosthetic heart valve 4502, according to an embodiment. The valve 4502 is shown having a septal tether that includes a relatively rigid elongate member 4592 attached at an end portion thereof to an anchor 4593 (e.g., a paddle-type anchor or the like). The septal tether can be used to maintain a position of the deployed valve 4502 in, for example, an annulus of a native mitral valve by placing the anchor 4593 in a trans-septal puncture used for trans-septal delivery from the IVC to the left atrium. FIG. 63 is cut-away view of a heart showing the location of the deployed valve 4502 in the annulus of the native mitral valve.

Figure 64:
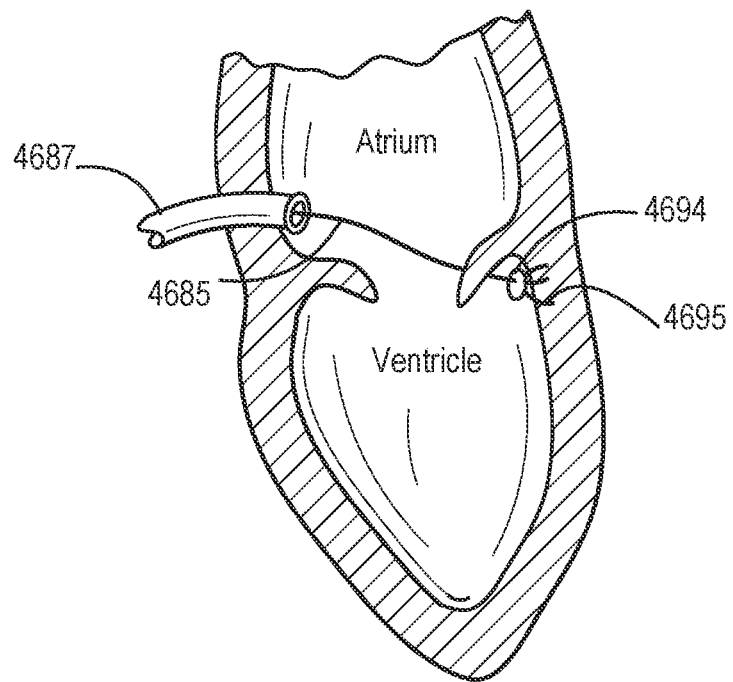
FIG. 64 is an illustration of a side view of a portion of a delivery system having a docking receptacle with a keyed feature and/or tissue grabbing features for anchoring to a free wall of native tissue, according to an embodiment.
Figure 65:
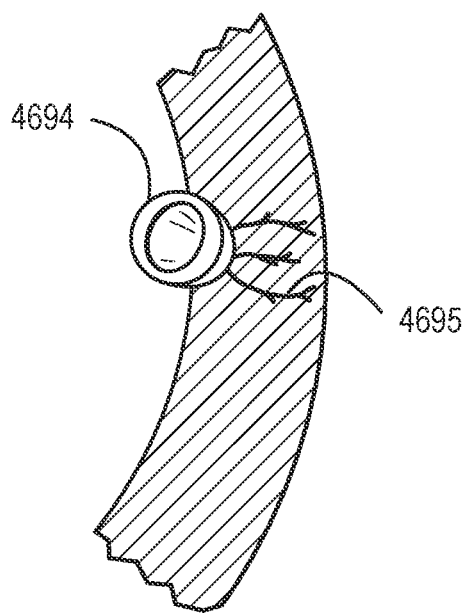
FIG. 65 is an illustration of an enlarged view of at least a portion of the tissue-grabbing features of FIG. 64 shown anchored to the free wall.

FIG. 64 is cut-away view of a heart showing a guide wire delivery catheter 4687 (or positioning tool) inserted into a left atrium of a heart, according to an embodiment. A guide wire 4685 is shown extending from the guide wire delivery catheter 4687. A distal end portion of the guide wire 4685 is shown with a docking receptacle 4694 with a keyed-tissue grabbing feature 4695 for anchoring to the free wall of the left ventricle. FIG. 65 is an enlarged cut-away view of the heart showing the docking receptacle 4694 anchored to the free wall of the left ventricle.

FIG. 66 is a flowchart illustrating a method 10 of deploying a side deliverable transcatheter prosthetic heart valve in an annulus of a native valve, according to an embodiment. The prosthetic valve can be any of the valves disclosed herein. For example, the valve can have (i) an outer frame with one or more of a distal anchoring element, a proximal anchoring element, and/or an anterior anchoring element(s) and (ii) a flow control component mounted within the outer frame configured to permit blood flow in a single direction through an inflow end of the valve and to block blood flow in an opposite direction through an outflow end of the valve. The valve can be delivered via, for example, side or orthogonal delivery. For example, the valve can be delivered via any of the processes and/or methods described in detail herein and/or in the '957 PCT.

The method 10 includes advancing a guide wire to an atrium, through a plane defined by the annulus of the native valve, and behind a native leaflet of the native valve, at 11. In some implementations, the native valve can be a native tricuspid valve or a native mitral valve. The prosthetic valve is advanced in an orthogonally compressed configuration through a lumen of a delivery catheter and along the guide wire and into the atrium, at 12. For example, in some embodiments, the prosthetic valve can include a distal anchoring element that has, for example, a guide wire coupler that can engage and/or can be disposed on or about the guide wire. In some embodiments, the guide wire coupler can be an atraumatic ball disposed at an end of the distal anchoring element that defines an opening configured to receive the guide wire.

The prosthetic valve is released from the delivery catheter to allow at least a portion of the prosthetic valve to transition to an expanded configuration with the distal anchoring element of the prosthetic valve in an extended configuration, at 13. In some embodiments, for example, the distal anchoring element can be a reconfigurable anchoring element that can be in an extended configuration during delivery and/or deployment and configured to transition to a compressed or folded configuration to secure the prosthetic valve in the annulus of the native valve.

The prosthetic valve is advanced along the guide wire to place the distal anchoring element in a position behind the native leaflet and to seat the prosthetic valve in the annulus of the native valve, at 14. For example, the native valve can be a native tricuspid valve and the native leaflet can be a posterior (e.g., P2) leaflet. The guide wire is withdrawn to release the distal anchoring element from the extended position to the folded position allowing the distal anchoring element to capture at least one of native leaflet or chordae and to secure the native leaflet or chordae between the distal anchoring element and a perimeter wall of the prosthetic valve, at 15. For example, in some embodiments, the distal anchoring element can be a biased, self-folding, and/or self-contracting anchoring element that can return to the folded position when the guide wire is withdrawn. In some embodiments, the distal anchoring element can have a length that is sufficient to capture a desired amount of native tissue and/or chordae, thereby securing at least a distal end portion of the prosthetic valve in the native annulus.

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations.

The embodiments described herein can include various combinations and/or sub-combinations of the functions, components, and/or features of the different embodiments described. Various of the above-disclosed and other features and functions, or alternatives thereof, may be combined into many other different systems or applications. Various presently unforeseen or unanticipated alternatives, modifications, variations, or improvements therein may be subsequently made by those skilled in the art, each of which is also intended to be encompassed by the disclosed embodiments.

What is claimed:

1. A side-deliverable prosthetic heart valve, the prosthetic valve comprising:
   an outer frame having a perimeter wall that circumscribes a central channel extending along a central axis of the outer frame;
   a flow control component mounted within the central channel of the outer frame, the flow control component having an inner frame and a set of leaflets coupled to the inner frame,
   the prosthetic valve configured to be folded along a longitudinal axis and compressed along the central axis to place the prosthetic valve in a compressed configuration for delivery via a delivery catheter, the longitudinal axis being substantially parallel to a lengthwise axis of the delivery catheter when the prosthetic valve is disposed therein, the prosthetic valve configured to transition to an expanded configuration when the prosthetic valve is released from the delivery catheter; and
   a distal anchoring element having a first end portion coupled to a distal side of the perimeter wall of the outer frame and a second end portion opposite the first end portion, the second end portion includes a guide wire coupler, the guide wire coupler configured to be threaded over a guide wire to allow the distal anchoring element to selectively engage the guide wire and to be advanced along the guide wire during deployment of the prosthetic valve, the distal anchoring element being in an extended configuration during deployment such that the distal anchoring element can capture at least one of native leaflet or chordae and, in response to the guide wire being disengaged from the second end portion, the distal anchoring element transitions to a folded configuration in which at least one of the native leaflet or the chordae can be secured between the distal anchoring element and the distal side of the perimeter wall.

2. The prosthetic valve of claim 1, further comprising:
   a proximal anchoring element coupled to a proximal side of the perimeter wall, the proximal anchoring element configured to secure a proximal portion of the prosthetic valve to proximal subannular tissue when the prosthetic valve is disposed in the annulus of the native valve.

3. The prosthetic valve of claim 1, further comprising:
   an anterior anchoring element coupled to an anterior side of the perimeter wall, the anterior anchoring element including an engagement portion configured to transition between a first configuration in which the engagement portion extends in a direction of the central axis to allow the engagement portion to engage at least one of an anterior native leaflet or anterior chordae, and a second configuration in which the engagement portion is at least partially retracted to allow the engagement portion to capture and secure the anterior native leaflet or the anterior chordae between the anterior anchoring element and the anterior side of the perimeter wall.

4. The prosthetic valve of claim 3, wherein the anterior anchoring element includes a sleeve, the engagement portion is at least partially disposed in the sleeve and extends from the sleeve when in the first configuration, the engagement portion is at least partially retracted into the sleeve when in the second configuration to capture secure the anterior native leaflet or the anterior chordae between the anterior anchoring element and the anterior side of the perimeter wall.

5. The prosthetic valve of claim 3, wherein the engagement portion of the anterior anchoring element is a clip.

6. The prosthetic valve of claim 3, wherein the anterior anchoring element is a wire, the engagement portion of the anterior anchoring element being a reconfigurable portion of the wire.

7. The prosthetic valve of claim 1, further comprising:
   a first anterior anchoring element coupled to an anterior side of the perimeter wall, the first anterior anchoring element including a first engagement portion configured to transition between a first configuration and a second configuration; and
   a second anterior anchoring element coupled to the anterior side of the perimeter wall, the second anterior anchoring element include a second engagement portion configured to transition between a first configuration and a second configuration,
   in the first configuration, the first engagement portion and the second engagement portion extending in a subannular direction to allow the first engagement portion and the second engagement portion to engage at least one of an anterior native leaflet or anterior chordae, and
   in the second configuration, the first engagement portion and the second engagement portion are at least partially retracted to allow the first engagement portion and the second engagement portion to capture and secure the anterior native leaflet or the anterior chordae between the anterior side of the perimeter wall and the first and second engagement portions.

8. The prosthetic valve of claim 1, further comprising:
an atrial collar coupled to an atrial edge portion of the perimeter wall of the outer frame, the atrial collar configured to contact supra-annular tissue when the prosthetic valve is disposed in the annulus of the native valve.

9. A side-deliverable prosthetic heart valve, the prosthetic valve comprising:
an outer frame having a perimeter wall that circumscribes central channel extending along a central axis of the outer frame;
a flow control component mounted within the central channel of the outer frame, the flow control component having an inner frame and a set of leaflets coupled to the inner frame,
the prosthetic valve configured to be folded along a longitudinal axis and compressed along the central axis to place the prosthetic valve in a compressed configuration for delivery via a delivery catheter, the longitudinal axis being substantially parallel to a lengthwise axis of the delivery catheter when the prosthetic valve is disposed therein, the prosthetic valve configured to transition to an expanded configuration when the prosthetic valve is released from the delivery catheter;
a distal anchoring element coupled to a distal side of the perimeter wall of the outer frame, the distal anchoring element releasably coupled to a guide wire, the distal anchoring element configured to be advanced along the guide wire when in an extended configuration to capture at least one of a distal native leaflet or distal chordae, the distal anchoring element transitioning to a folded configuration when released from the guide wire to allow the distal anchoring element to secure the distal native leaflet or the distal chordae between the distal anchoring element and the distal side of the perimeter wall; and
an anterior anchoring element coupled to an anterior side of the perimeter wall, the anterior anchoring element including an engagement portion, the anterior anchoring element being a wire and the engagement portion being a reconfigurable portion of the wire configured to transition between a first configuration in which the engagement portion extends in a direction of the central axis to allow the engagement portion to engage at least one of an anterior native leaflet or anterior chordae, and a second configuration in which the engagement portion is at least partially retracted to allow the engagement portion to capture and secure the anterior native leaflet or the anterior chordae between the anterior anchoring element and the anterior side of the perimeter wall.

10. The prosthetic valve of claim 9, wherein the distal anchoring element includes a guide wire coupler disposed at a distal end portion of the distal anchoring element, the guide wire coupler configured to be threaded over the guide wire such that the distal anchoring element can be advanced along the guide wire during deployment of the prosthetic valve.

11. The prosthetic valve of claim 9, wherein anterior anchoring element is temporarily coupled to the guide wire, the anterior anchoring element configured to transition from the first configuration to the second configuration in response to being released from the guide wire.

12. The prosthetic valve of claim 11, wherein releasing the guide wire includes withdrawing the guide wire from the guide wire coupler and the anterior anchoring element.

13. The prosthetic valve of claim 9, further comprising:
a proximal anchoring element coupled to a proximal side of the perimeter wall, the proximal anchoring element configured to secure a proximal portion of the prosthetic valve to proximal subannular tissue when the prosthetic valve is disposed in the annulus of the native valve.

14. The prosthetic valve of claim 9, wherein the anterior anchoring element includes a sleeve, the engagement portion is at least partially disposed in the sleeve and extends from the sleeve when in the first configuration, the engagement portion is at least partially retracted into the sleeve when in the second configuration to capture secure the anterior native leaflet or the anterior chordae between the anterior anchoring element and the anterior side of the perimeter wall.

15. The prosthetic valve of claim 14, wherein the engagement portion of the anterior anchoring element is a clip.

16. The prosthetic valve of claim 9, wherein the anterior anchoring element is a first anterior anchoring element and the engagement portion is a first engagement portion, the prosthetic valve further comprising:
a second anterior anchoring element coupled to the anterior side of the perimeter wall, the second anterior anchoring element including a second engagement portion configured to transition between a first configuration in which the second engagement portion extends in a direction of the central axis to allow the second engagement portion to engage at least one of the anterior native leaflet or anterior chordae, and a second configuration in which the second engagement portion is at least partially retracted to allow the second engagement portion to capture and secure the anterior native leaflet or the anterior chordae between the second anterior anchoring element and the anterior side of the perimeter wall.

17. The prosthetic valve of claim 9, further comprising:
an atrial collar coupled to an atrial edge portion of the perimeter wall of the outer frame, the atrial collar configured to contact supra-annular tissue when the prosthetic valve is disposed in the annulus of the native valve.

18. A method for deploying a side-deliverable prosthetic heart valve to a patient, the method comprising:
advancing a guide wire to an atrium, through a plane defined by an annulus of a native valve, and behind a native leaflet of the native valve;
advancing the prosthetic valve in an orthogonally compressed configuration through a lumen of a delivery catheter and into the atrium, the prosthetic valve including a distal anchoring element releasably coupled to the guide wire such that the prosthetic valve is advanced along a portion of the guide wire;
releasing the prosthetic valve from the delivery catheter to allow at least a portion of the prosthetic valve to transition to an expanded configuration, the distal anchoring element being in an extended configuration after the releasing;
advancing the prosthetic valve along the guide wire to place the distal anchoring element in a position behind the native leaflet and to seat the prosthetic valve in the annulus of the native valve; and
withdrawing the guide wire to release the distal anchoring element to a folded position allowing the distal anchoring element to capture at least one of native leaflet or chordae and to secure the native leaflet or chordae between the distal anchoring element and a perimeter wall of the prosthetic valve.

19. The method of claim 18, wherein the native leaflet is a posterior leaflet, the prosthetic valve includes an anterior anchoring element releasably coupled to the guide wire, the method further comprising:
withdrawing the guide wire to release the anterior anchoring element to a folded position allowing an engagement portion of the anterior anchoring element to capture at least one of an anterior native leaflet or anterior chordae and to secure the anterior native leaflet or anterior chordae between the anterior anchoring element and the perimeter wall.

20. The method of claim 18, wherein the distal anchoring element includes a guide wire coupler disposed at a distal end portion of the distal anchoring element, the guide wire coupler configured to be threaded over the guide wire.

21. The method of claim 18, further comprising:
seating the prosthetic valve in the annulus of the native valve; and
positioning a proximal anchoring element of the prosthetic valve in an anchoring position in which the proximal anchoring element engages subannular tissue on a proximal side of the annulus.

22. The method of claim 18, wherein the native leaflet is a posterior leaflet of a native mitral valve.

23. The method of claim 18, wherein the distal anchoring element extends from a distal side of a transannular section of the prosthetic valve, the releasing the prosthetic valve from the delivery catheter includes releasing the distal anchoring element prior to releasing the transannular section of the prosthetic valve.

24. The method of claim 18, wherein the distal anchoring element extends from a transannular section of the prosthetic valve, the prosthetic valve including an atrial collar coupled to an atrial edge portion of the transannular section of the prosthetic valve, the releasing the prosthetic valve from the delivery catheter includes releasing the distal anchoring element and at least a portion of the atrial collar prior to releasing the transannular section of the prosthetic valve.

* * * * *